(12) United States Patent
Parang et al.

(10) Patent No.: US 7,799,753 B2
(45) Date of Patent: Sep. 21, 2010

(54) BISUBSTRATE INHIBITORS OF PROTEIN TYROSINE KINASES AS THERAPEUTIC AGENTS

(75) Inventors: Keykavous Parang, Saunders Town, RI (US); Gongqin Sun, Wakefield, RI (US); Anil Kumar, Pilani (IN); Nguyen H. Nam, Hanoi (VN); Yue-Hao Wang, Houston, TX (US); Guofeng Ye, Quincy, MA (US)

(73) Assignees: Board of Governers for Higher Education, Providence, RI (US); State of Rhode Island and Providence Plantations, Providence, RI (US)

(*) Notice: Subject to any disclaimer, the term of this patent is extended or adjusted under 35 U.S.C. 154(b) by 425 days.

(21) Appl. No.: 11/565,914

(22) Filed: Dec. 1, 2006

(65) Prior Publication Data

US 2007/0173437 A1    Jul. 26, 2007

Related U.S. Application Data

(63) Continuation of application No. PCT/US2005/019846, filed on Jun. 6, 2005.

(60) Provisional application No. 60/577,133, filed on Jun. 4, 2004.

(51) Int. Cl.
*A61K 38/00* (2006.01)
(52) U.S. Cl. ........................................................ 514/2
(58) Field of Classification Search ........................ None
See application file for complete search history.

(56) References Cited

U.S. PATENT DOCUMENTS

2002/0031820 A1    3/2002    Cole et al.

FOREIGN PATENT DOCUMENTS

| WO | WO0042042 | * | 7/2000 |
| WO | WO0119829 | * | 3/2001 |

OTHER PUBLICATIONS

Parang et al. "Designing bisubstrate analog inhibitors for protein kinases," Pharmacology & Therapeutics, 2002, 93, 145-157.*
Kamath et. al. "Development and characterization of potent and specific peptide inhibitors of p60c-src protein tyrosine kinase using pseudosubstrate-based inhibitor design approach," J. Peptide Res., 2003, 62, 260-268.*

* cited by examiner

Primary Examiner—Cecilia Tsang
Assistant Examiner—Christina Bradley
(74) Attorney, Agent, or Firm—Gauthier & Connors LLP

(57) ABSTRACT

A bisubstrate inhibitor of Src kinases, having a nucleotide or N-heteroaromatic moiety; and a peptide/phosphopeptide, peptidomimetic, or phosphopeptide mimic moiety. The moieties are linked by a rigid or a flexible linker. The nucleotide or N-heteroaromatic moiety is ATP, ATP-mimics, N-heteroaromatics including purine-based derivatives, pyrimidine-based derivatives such as 2,4-diamino-5-substituted pyrimidine derivatives, pyrazole[3,4-d]pyrimidine derivatives, pyrrolo[2,3-d]pyrimidine derivatives, pyrido[2,3-d]pyrimidine derivatives, amino-substituted dihydropyrimido[4,5-d]pyrimidinone derivatives, thieno- and furo-substituted derivatives, quinazoline derivatives, and quinoline derivatives, and several natural products such as aminogenistein. The phosphopeptide mimics comprise phosphonate-based phosphotyrosine mimetics such as phosphonomethylphenylalanine (Pmp) and its analogues, carboxylic acid-based phosphotyrosine mimetics such as malonyltyrosine or phenylalanine analogues and their derivatives such as carboxymethyl phenylalanine, uncharged pTyr mimetics, and conformationally constrained peptides. The phosphopeptide or phosphopeptide mimics inhibits the Src kinases SH2 domain.

24 Claims, 47 Drawing Sheets

12-17

48
IC$_{50}$ = 64 μM

50
IC$_{50}$ = 39 μM

52
IC$_{50}$ = 18.0 μM

49
$IC_{50} = 0.59 \mu M$

51
$IC_{50} = 2.1 \mu M$

53
$IC_{50} = 30 \mu M$

X= -OH,, halogens, -N₃, -N=C=S, -COOH, -Me, R-NHCOO-, NO₂⁻, alkyls, aryls

94

95

96

97

98

99

BISUBSTRATE INHIBITORS OF PROTEIN TYROSINE KINASES AS THERAPEUTIC AGENTS

PRIORITY INFORMATION

This application claims the benefit of International Patent Application Serial No. PCT/US05/019846 filed on Jun. 6, 2005 and claims priority to U.S. Provisional Patent Application 60/577,133 filed on Jun. 4, 2004, all of which are incorporated herein by reference in their entirety.

BACKGROUND OF THE INVENTION

Protein Tyrosine Kinases and their Importance in Human Diseases

Protein tyrosine kinases (PTKs) are enzymes that catalyze phosphorylation of tyrosine in many proteins by the transfer of the γ-phosphoryl group from ATP. PTKs can be transiently activated following signals for cell growth or differentiation. The Src family of protein tyrosine kinases, Src, Yes, Lck, Fyn, Lyn, Fgr, Hck, Blk, and Yrk, are non-receptor tyrosine kinases. Enhanced Src tyrosine kinases activity has been directly linked to T-cell activation, mitogenesis, differentiation, cell transformation, and oncogenesis. For example, Src has been implicated in the development of several different cancers including colon and breast cancers for which transformed phenotypes have been correlated with Src mutations and/or overexpression. The design and evaluation of new compounds against Src tyrosine kinases are important due to the association of Src tyrosine kinases activity with several diseases related to cell signaling, such as cancer.

The initiation and progression of human colon cancer and resultant metastases is correlated with Src kinase activity. Src has also been implicated in breast cancer. In general, the elevated Src activity has been shown in at least 90% of the cases of breast, colon, pancreatic, and liver tumors. Src kinase activity is usually 4-20 fold higher in mammary carcinomas compared to normal tissues.

c-Src has been implicated in bone remodeling (resorption and formation) and several bone related diseases, such as osteoporosis, inflammation-mediated bone loss, rheumatoid arthritis, periodontal disease, Paget's disease, hypercalcaemia of malignancy and metastasis of certain cancers to bone.

Cellular signal transduction by Src is believed to play a key role in increased vascular permeability (VP). Src kinases mediate signaling activity in response to various growth factors, including VEGF. The ability to control increased VP by suppression of a signaling pathway would be useful for the treatment of patients suffering from a number of diseases and conditions, such as acute myocardial infarction. Src inhibitors may also be useful to prevent the second injury that results from a VEGF-mediated increase in VP such as that seen following stroke.

General Structural Features of Src Tyrosine Kinases.

Src family kinases (SFKs) share common structural motifs that determine their cellular and catalytic activity. The homologous domains include: (i) the fatty acid acylation domain, which targets the kinases to the plasma membrane, (ii) the Src homology 3 (SH3) and Src homology 2 (SH2) domains, which facilitate protein-protein interactions, (iii) the kinase domain (catalytic, including ATP and substrate binding sites), and (iv) the C-terminal regulatory domain. SH2 domains are modules of approximately 100 amino acids that have evolved to recognize and bind specifically to tyrosyl-phosphorylated sequences located on proteins in response to extracellular signals and mediate interactions of the PTKs with other cellular proteins.

All SFKs contain a ~260-amino acid conserved catalytic domain, which folds into two structurally dissimilar lobes, i.e., the N- and C-terminal lobes that are associated with ATP binding and peptide/protein binding, respectively. These lobes are joined by a linker peptide coil of five to six residues, called the hinge region. ATP itself, as well as most ATP binding site inhibitors, bind to kinases in a similar manner through a tridentate hydrogen bonding motif linked to the backbone of the hinge region. A significant body of data on nucleotide analogs has suggested that the principal course of affinity of nucleotides for kinases comes from the adenine group rather than the ribo-phosphate moieties.

X-ray studies of selective pyrazolopyrimidine inhibitors in Hck kinase-PP1 and Lck kinase-PP2 complexes have revealed a deep, hydrophobic binding pocket near the ATP binding site for the aryl moiety of the pyrazolopyrimidine template. The source of the differential kinase selectivity observed in heterocyclic inhibitors is suggested to be the difference in residues lining the hydrophobic pocket. In this invention, in addition to ATP, N-heteroaromatics including purine-based derivatives, pyrimidine-based derivatives such as 2,4-diamino-5-substituted pyrimidine derivatives, pyrazole[3,4-d]pyrimidine derivatives, pyrrolo[2,3-d]pyrimidine derivatives, pyrido[2,3-d]pyrimidine derivatives, amino-substituted dihydropyrimido[4,5-d]pyrimidinone derivatives, thieno- and furo-substituted derivatives, quinazoline derivatives, and quinoline derivatives are disclosed as backbone structures in synthesizing heteroaromatic-phosphopeptide and heteroaromatic-peptide conjugates.

Src Kinase Inhibitors.

Src inhibitors may be categorized into three major classes: (i) SH2 inhibitors, (ii) SH3 inhibitors, and (iii) kinase domain inhibitors (ATP and/or substrate binding site inhibitors). For potent inhibitors to be of value, they must exhibit selectivity against a specific Src kinase.

Although significant efforts have been made on the development of SH2 domain inhibitors to inhibit SH2-mediated signaling events, much less attention has been paid to the outcome of this inhibition and kinase activation. It has been shown that in vitro phosphopeptide ligands of the SH2 domain are able to increase Src kinase activity by disrupting the intramolecular interactions between the $Tyr^{527}$-phosphorylated C-terminal tail and the SH2 domain, thereby inducing a change from a closed inactive to an open active conformation of Src. In general, SH3 inhibitors have exhibited relatively weak inhibitory potency ($K_i$ in the high micromolar range) compared to the most potent ATP analogs.

Inhibitors of the kinase domain, however, block Src-dependent phosphorylation of substrate proteins. Protein kinases can be inhibited by compounds competing with ATP. These inhibitors include maleimides, pyrazolopyrimidines, pyrrolopyrimidines, quinazolines, pyridopyrimidines, isoquinoline, and several other classes of compounds. This lack of specificity highlights one disadvantage of ATP analogs as PTK inhibitors. ATP serves as a common substrate for many non-kinase enzymes and therefore any process that utilizes ATP could be a potential target. The pyrazolopyrimidine compounds (PP1 and PP2) have been described as potent inhibitors of SFKs with mark selectivity versus AZP-70, JAK2, EGFR and PKA.

While the ATP binding lobe is the predominant site targeted by protein tyrosine kinase (PTK) inhibitors, there has been a consistent effort to develop inhibitors that disrupt protein substrate binding. While the ATP binding site is ubiquitous in all protein kinases, the interactions between the protein kinase and the protein substrate are unique. Substrate competitive inhibitors are likely to be less toxic than ATP-mimics, since they bind to domains at the kinase site that are less conserved than the ATP binding site. Since protein substrates are present at much lower concentrations than cellular ATP, such protein-competitive inhibitors would seem to be superior to ATP-competitive inhibitors. This approach has its roots in the belief that protein kinases recognize protein substrates by interacting with the amino acid sequences surrounding the phosphorylation site. These efforts identified preferred peptide substrates for a number of PTKs, but the affinity between the peptides and the PTKs were weak and they displayed relatively little selectivity among PTKs. The best examples from these studies are peptides, YIYGSFK (SEQ ID NO: 1) and CIYKYY (SEQ ID NO: 2), which were reported to be inhibitors of Src.

SUMMARY OF INVENTION

The objective of this invention was to design selective and potent Src kinase inhibitors that can have potential application for drug development. The design, synthesis, and evaluation of new compounds against Src tyrosine kinases are attractive due to the association of Src tyrosine kinases activity with several diseases including cancer, osteoporosis, cardiovascular disorders, and immune system dysfunction. Src exists as an intriguing therapeutic target for anticancer drug discovery. Src is overexpressed in colon, breast, hepatic and pancreatic tumors, as well as in certain B-cell leukemia and lymphoma, for which transformed phenotypes have been correlated with Src mutations and/or over-expression of Src tyrosine kinase activities. Blocking the activated Src by specific inhibitors is expected to slow down or stop the growth of cancer cells, but have minor or no effect on normal cells, making such inhibitors effective drugs with little side effects.

Designing small-molecule inhibitors specific for Src kinase domain is challenging due to the highly homologous nature of this domain within the Src family. Several experimental compounds, such as PP1, PP2, CGP76030, SKI606, PD173955, PD180970, and SU6656, have been used for targeting the Src family of kinases. Only a few inhibitors have been tested without provoking toxicity in animal models. In fact, many of the Src kinase inhibitors published so far lack sufficient specificity desirable for clinical application or even pharmacological tools. Bicyclic N-heteroaromatics such as pyrazolopyrimidine and pyrrolopyrimidine have been described as potent inhibitors of c-Src and other PTKs. Unfortunately, attempts to improve the biological profile of the latter compounds have so far met with little success. Systemic approaches and mechanistic designed inhibitors are needed to improve the selectivity and potency of these compounds against Src kinases.

The specific purpose of this invention was to design Src kinase inhibitors that incorporate the best features of several successful inhibitor design strategies, including ATP-competitive inhibitors, phosphopeptides, peptide substrates inhibitors, and structure-guided design. The ATP binding site molecular recognition motif was exploited alone or in combination with other recognition motifs, such as the SH2 domain, and substrate binding site molecular recognition motifs, to develop selective and potent inhibitors for Src tyrosine kinases. Two classes of compounds were designed.

The first class of compounds (FIG. 1) included heteroaromatic-phosphopeptide conjugates and was designed to target ATP-binding site and the SH2 domain. In addition to ATP, several other heteroaromatic groups are disclosed in this invention. ATP mimics are N-heteroaromatics including purine-based derivatives, pyrimidine-based derivatives such as 2,4-diamino-5-substituted pyrimidine derivatives, pyrazole[3,4-d]pyrimidine derivatives, pyrrolo[2,3-d]pyrimidine derivatives, pyrido[2,3-d]pyrimidine derivatives, amino-substituted dihydropyrimido[4,5-d]pyrimidinone derivatives, thieno- and furo-substituted derivatives, quinazoline derivatives, quinoline derivatives, and several natural products such as aminogenistein. SH2 domain-directed pTy mimetics include phosphonate-based pTyr mimetics such as phosphonomethylphenylalanine (Pmp) and its analogues, carboxylic acid-based pTyr mimetics such as malonyltyrosine or phenylalanine analogues and their derivatives such as carboxymethyl phenylalanine, uncharged pTyr mimetics, and conformationally constrained peptides. These ATP mimics-phosphopeptide conjugates serve as novel templates for the designing protein tyrosine kinase inhibitors to block SH2 mediated protein-protein interactions and to counter the activation of enzyme resulted from the SH2 inhibition.

The second class of compounds (FIG. 2) included heteroaromatic-peptide conjugates and was designed to target the kinase domain. In addition to ATP, several other heteroaromatic groups are disclosed in this invention. ATP mimics are N-heteroaromatics including purine-based derivatives, pyrimidine-based derivatives such as 2,4-diamino-5-substituted pyrimidine derivatives, pyrazole[3,4-d] pyrimidine derivatives, pyrrolo[2,3-d]pyrimidine derivatives, pyrido[2,3-d]pyrimidine derivatives, amino-substituted dihydropyrimido [4,5-d]pyrimidinone derivatives, thieno- and furo-substituted derivatives, quinazoline derivatives, quinoline derivatives, and several natural products such as aminogenistein. The peptide moiety may bind to substrate binding site or other sites in the kinase domain. Peptides and peptide-like compounds include all substrate binding site inhibitors such as peptidomimetics, cyclic peptides, small molecules designed to mimic peptides, and small molecules designed to bind to activation domain, ATP binding site and substrate binding site. Peptides attached to N-heteroaromatics have several functional groups. The electrostatic, hydrophobic, or hydrogen bonding interactions of these functional groups with several amino acids in the kinase domain, such as those in the hinge region, the substrate docking site, the substrate binding site, and the surrounding exterior region of the ATP binding site, may contribute to the enhancement of potency and/or selectivity. Therefore, bicyclic N-heteroaromatic-peptide conjugates may target the ATP binding site in addition to other sites required for substrate recognition or substrate phosphorylation. Peptides may bind to several cavities that may be indirectly or directly involved in substrate recognition or binding. Atoms of the heteroaromatic core and the substituents on the heteroaromatic core such as phenyl carbons or both positions were used as attachment points. Examples of heteroaromatic are the 3-phenylpyrazolopyrimidine or 3-phenylpyrrolopyrimidines.

These conjugates may block the ATP binding site along with other potential sites. Alternatively, these potential sites may show lower homology than the ATP binding site shared between protein kinases. An attractive feature of these compounds is that the specificity provided by the peptide or phosphopeptide substrate can be integrated into the molecule, and therefore some of the chimeric compounds are expected to have a higher specificity. Several of these N-heteroaromatic-peptide conjugates exhibited higher inhibitory potency than the corresponding parent compounds, N-heteroaromatics, phosphopeptides, and peptides.

BRIEF DESCRIPTION OF THE DRAWINGS

Other objects, features and advantages of the present invention will become more apparent as the description proceeds with reference to the accompanying drawings, wherein.

DETAILED DESCRIPTION OF THE INVENTION

Different approaches have been examined for the possibility of using bisubstrate analog inhibitors against protein kinases. We have reviewed several strategies used for designing bisubstrate inhibitors of protein kinases. Bisubstrate analog inhibitors mimic two natural ligands that simultaneously associate with two binding sites. A greater selectivity is likely to result, since the combination of two substrates required by the target enzyme into a single molecule makes it less likely that both components will be recognized by other enzymes. We have designed bisubstrate inhibitors targeting the ATP binding site and substrate binding site of the insulin receptor kinase that was disclosed in WO 0170770 (2001). We have also designed several bivalent ligands targeting the Src SH2 domain and ATP binding site that was filed as a Provisional Patent No. 60/577,133 which is incorporated herein.

Two classes of compounds are disclosed against Src kinases: (1) N-Heteroaromatic-phosphopeptide conjugates and (2) N-Heteroaromatic-peptide conjugates.

The first class of compounds (See FIG. 1) includes heteroaromatic-phosphopeptide conjugates and targets ATP-binding site and the SH2 domain. In addition to ATP, several other heteroaromatic groups are disclosed in this invention. ATP mimics are N-heteroaromatics including purine-based derivatives, pyrimidine-based derivatives such as 2,4-diamino-5-substituted pyrimidine derivatives, pyrazole[3,4-d]pyrimidine derivatives, pyrrolo[2,3-d]pyrimidine derivatives, pyrido[2,3-d]pyrimidine derivatives, amino-substituted dihydropyrimido[4,5-d]pyrimidinone derivatives, thieno- and furo-substituted derivatives, quinazoline derivatives, quinoline derivatives, and several natural products such as aminogenistein. SH2 domain-directed pTy mimetics include phosphonate-based pTyr mimetics such as phosphonomethylphenylalanine (Pmp) and its analogues, carboxylic acid-based pTyr mimetics such as malonyltyrosine or phenylalanine analogues and their derivatives such as carboxymethyl phenylalanine, uncharged pTyr mimetics, and conformationally constrained peptides. These ATP mimics-phosphopeptide conjugates may serve as novel templates for the designing protein tyrosine kinase inhibitors to block SH2 mediated protein-protein interactions and to counter the activation of enzyme resulted from the SH2 inhibition.

Figure 2:
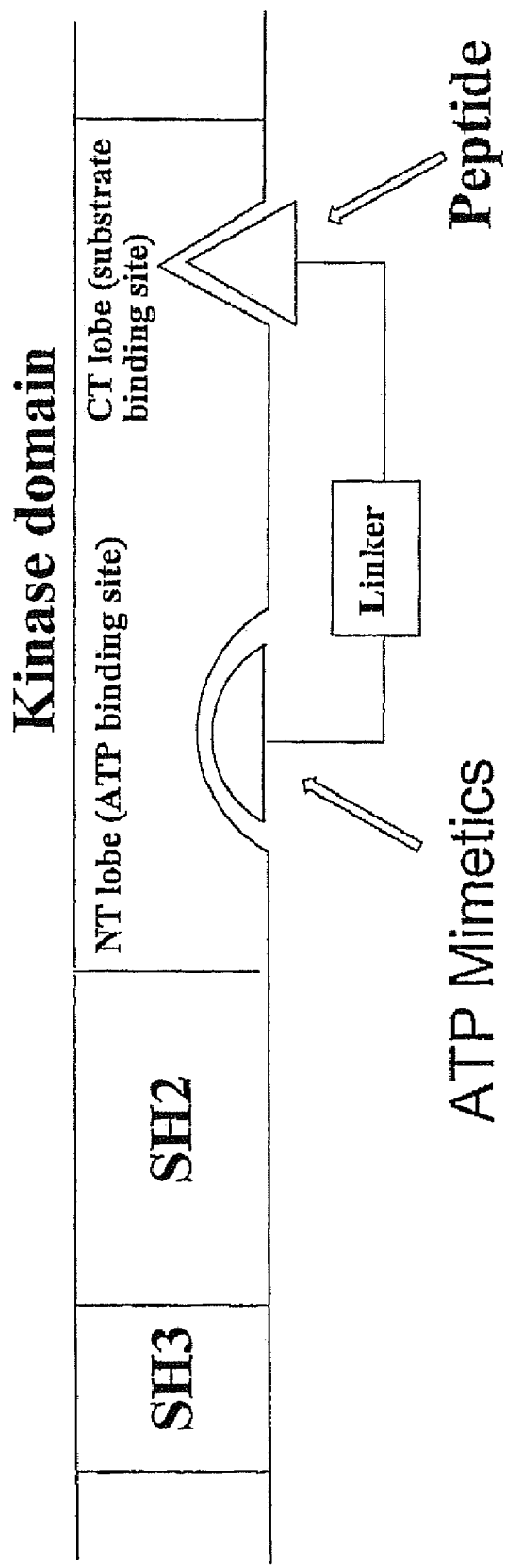
FIG. 2 shows heteroaromatic-peptide conjugates as Src kinase inhibitors targeting kinase domain.

The second class of compounds (See FIG. 2) includes heteroaromatic-peptide conjugates and targets the kinase domain. In the case of the ATP-peptide conjugates, peptides were connected to the γ-phosphate of ATP. By the attachment of the peptide to ATP, the peptide moiety is oriented directly toward the substrate binding site by the ribo-phosphate of ATP. In other words, there is a geometric boundary on the substrate alignment in the catalytic site of protein kinases. In addition to ATP, several other heteroaromatic groups are disclosed in this invention. ATP mimics are N-heteroaromatics including purine-based derivatives, pyrimidine-based derivatives such as 2,4-diamino-5-substituted pyrimidine derivatives, pyrazole[3,4-d]pyrimidine derivatives, pyrrolo[2,3-d]pyrimidine derivatives, pyrido[2,3-d]pyrimidine derivatives, amino-substituted dihydropyrimido[4,5-d]pyrimidinone derivatives, thieno- and furo-substituted derivatives, quinazoline derivatives, and quinoline derivatives. The peptide moiety may bind to substrate binding site or other sites in the kinase domain. Peptides include all substrate binding site inhibitors such as peptidomimetics, cyclic peptides, small molecules designed to mimic peptides, and small molecules designed to bind to activation domain, ATP binding site and substrate binding site. Peptides attached to N-heteroaromatics have several functional groups. The electrostatic, hydrophobic, or hydrogen bonding interactions of these functional groups with several amino acids in the kinase domain, such as those in the hinge region, the substrate docking site, the substrate binding site, and the surrounding exterior region of the ATP binding site, may contribute to the enhancement of potency and/or selectivity. Therefore, bicyclic N-heteroaromatic-peptide conjugates may target the ATP binding site in addition to other sites required for substrate recognition or substrate phosphorylation. Peptides may bind to several cavities that may be indirectly or directly involved in substrate recognition or binding. Atoms of the heteroaromatic core and the substituents on the heteroaromatic core such as phenyl carbons or both positions were used as attachment points. Examples of heteroaromatic are the 3-phenylpyrazolopyrimidine or 3-phenylpyrrolopyrimidines.

N-Heteroaromatic-Phosphopeptide Conjugates as Inhibitors of Src Tyrosine Kinases. (Bivalent Ligand Targeting the Src SH2 Domain and ATP-Binding Site)

The design of SH2 inhibitors has focused on peptidomimetic modifications of cognate peptide. SH2 domain-directed pTy mimetics include phosphonate-based pTyr mimetics such as phosphonomethylphenylalanine (Pmp) and its analogues, carboxylic acid-based pTyr mimetics such as malonyltyrosine or phenylalanine analogues and their derivatives such as carboxymethyl phenylalanine, uncharged pTyr mimetics, and conformationally constrained peptides. Although significant efforts have been made on the development of SH2 domain inhibitors to inhibit SH2 mediated signaling event, much less attention has been paid to the outcome of this inhibition and kinase activation. Tyr527 is located in the C-terminal tail of Src and, when phosphorylated by another protein kinase called C-terminal Src kinase (Csk), binds to the SH2 domain of Src, leads to the kinase inactivation, and locks the c-Src molecule in an inhibited closed conformation. C-terminal tail dephosphorylation or competitive binding of optimal SH2 domain ligands, allows the kinase domain to switch from a closed to an open conformation. The kinase reactivation by different pTyr-containing peptides related to pYEEI (SEQ ID NO: 3) known to bind the SH2 domain of Src has been demonstrated. Src is known to be activated by dual SH3/SH2 interactions with sequences in the focal adhesion kinase FAK and Sin. Designing inhibitors against Src SH2 domain-mediated protein-protein interactions has been complicated since several of these inhibitors could enhance the kinase catalytic activity by switching the closed inactive to the open active conformation by disrupting the intramolecular interactions between the $Tyr^{527}$-phosphorylated C-terminal tail and the SH2 domain. Such events might lead to side effects that would prevent SH2 inhibitors to be developed as a drug.

It has been previously shown that substitution on γ-phosphate of ATP with different moieties does not prevent or greatly reduce the ability of ATP for binding to ATP-binding site of Csk. This allowed hooking up ATP to peptide substrate to create bivalent inhibitors. Additionally, short and long chain substitution on N-terminal of tetrapeptide pYEEI (SEQ ID NO: 3) with aliphatic alkyl derivatives did not cause any significant loss in binding affinity to the Src SH2 domain.

Figure 1:
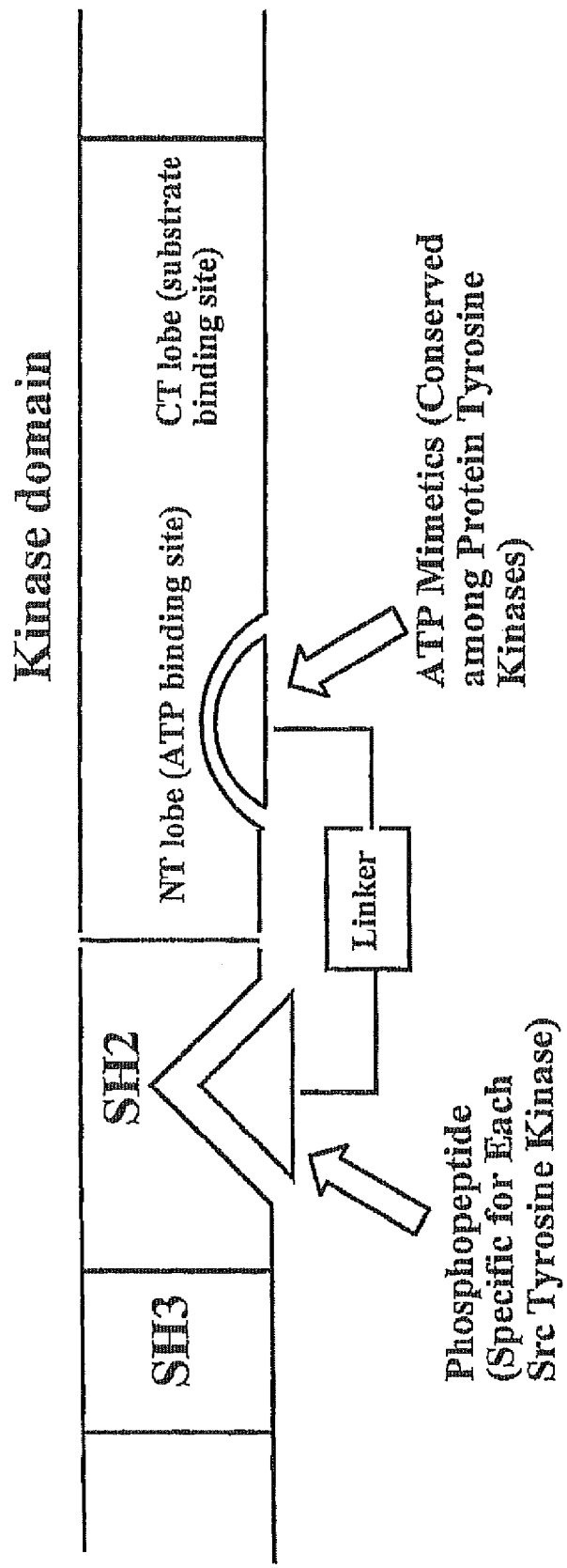
FIG. 1 shows heteroaromatic-phosphopeptide conjugates as Src kinase inhibitors targeting the Src SH2 domain and ATP-binding site.
Figure 3:
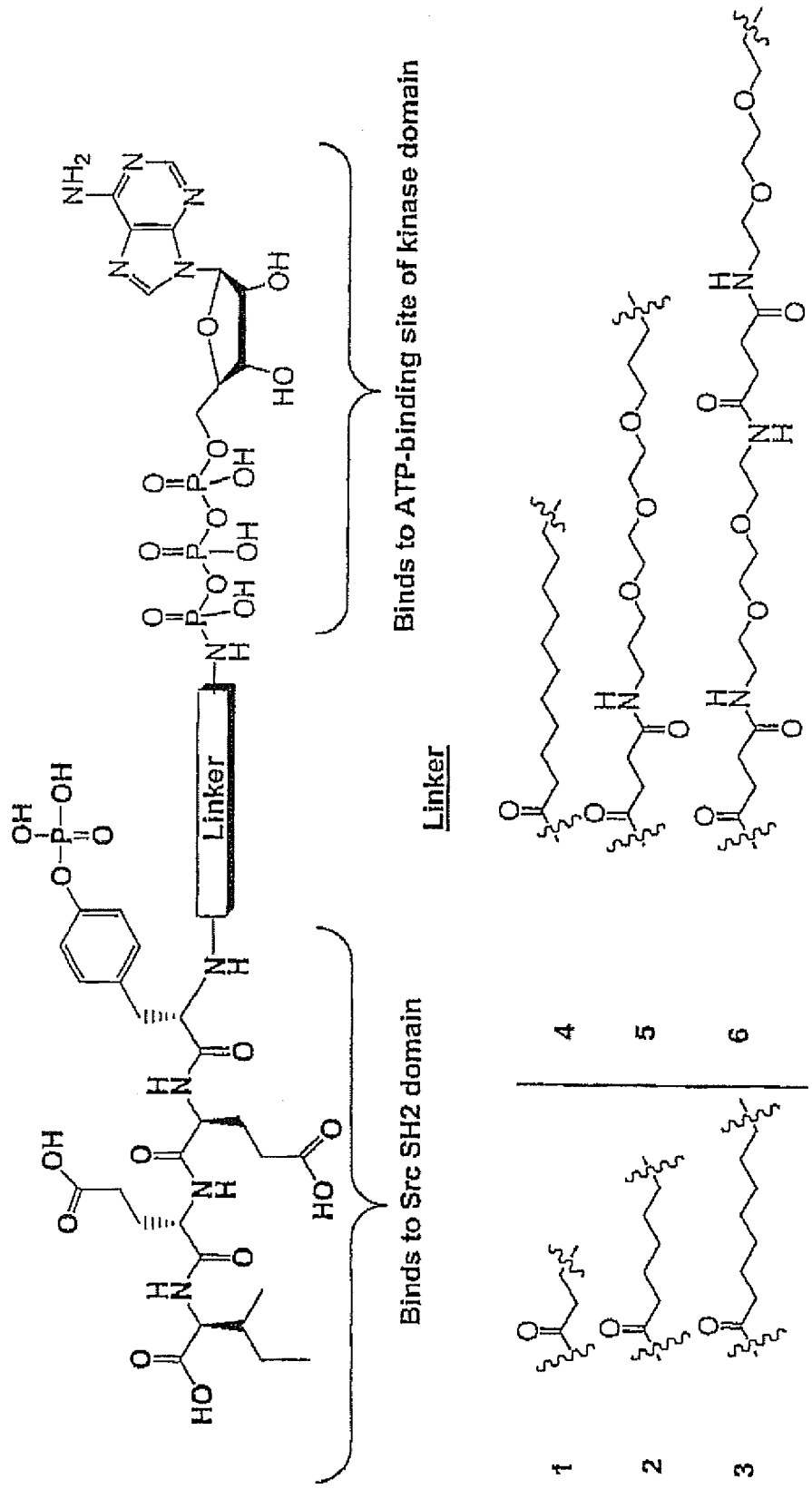
FIG. 3 shows synthesized ATP-phosphopeptide conjugates (1-7) as Src kinase inhibitors targeting the Src SH2 domain and ATP-binding site.
Figure 3:
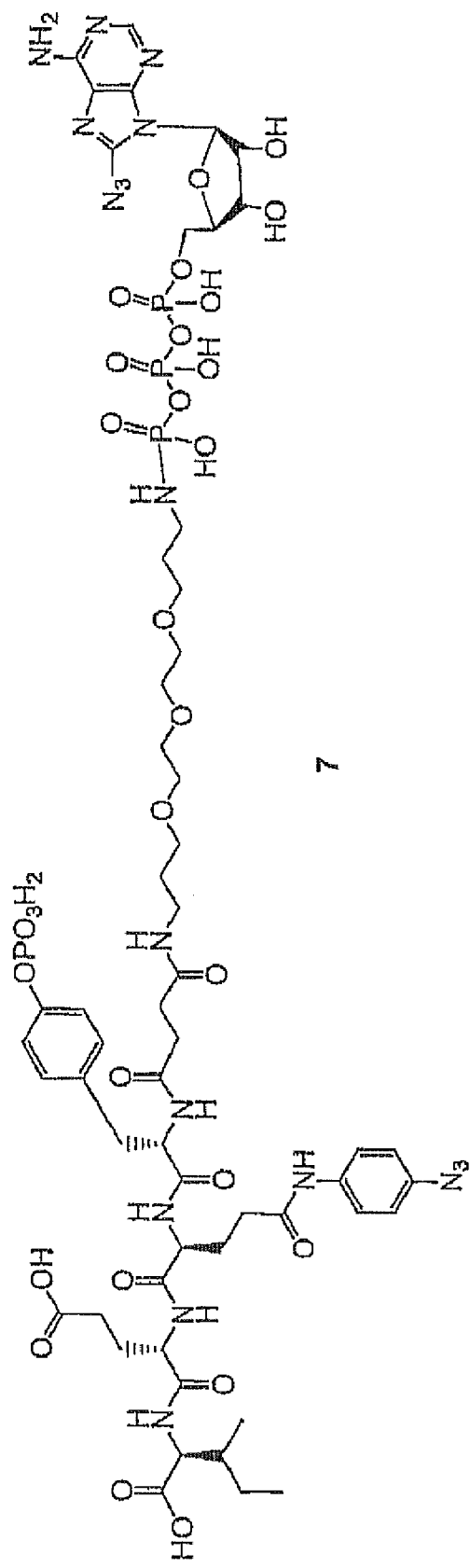

N-substituted derivatives of pYEEI (SEQ ID NO: 3) were selected for conjugation with ATP to synthesize a number of ATP-pYEEI (SEQ ID NO: 3) conjugates (1-7, FIG. 3) and to examine their inhibition pattern (potency and kinetics) against Src kinases. Several strategies used for designing bivalent inhibitors of protein kinases have been reviewed; none of these approaches target SH2 domain and ATP binding site of kinase domain. ATP was hooked up to the peptide substrate to create bivalent inhibitors against the ATP binding site and the SH2 domain of Src kinases (FIG. 1).

By linking ATP with a phosphopeptide (FIG. 3), it was possible to convert ATP substrate into a high-affinity inhibitor for Src kinases through exploiting the SH2 and ATP molecular recognition motifs and/or the kinase activation associated with SH2 inhibition was reduced. ATP-phosphopeptide conjugates were designed and synthesized as Src tyrosine kinase inhibitors based on a tetrapeptide sequence pTyr-Glu-Glu-Ile (pYEEI) (SEQ ID NO: 3) and ATP to block the SH2 domain signaling and substrate phosphorylation by ATP, respectively. To generate an effective bivalent ligand, it was necessary to connect the ATP and phosphopeptide binding modules with a linker that spans the distance between the binding sites on the active form of kinase. Alkyl chains of varying length of aminoacyl derivatives [—CO(A)NH—] were utilized as linkers to understand the relationship between linker length and inhibitory potency. Src and Lck were selected as tyrosine kinases as the target enzymes because phosphopeptide substrates (pYEEI) (SEQ ID NO: 3) for these enzymes have well characterized kinetically. This strategy can be used all Src kinases and also other protein tyrosine kinases. In general, ATP-phosphopeptide conjugates with optimal linkers such as compounds 5 and 7 ($K_i$=1.7-2.6 μM) showed higher binding affinities to the ATP-binding site relative to the other ATP-phosphopeptide conjugates having short or long linkers, 1-4 and 6, ($K_i$=10.1-16.1 μM) and ATP ($K_m$=74 μM). In general, ATP-phosphopeptide conjugates with an optimal linker size, such as compound 1 ($K_i$=1.7 µM), bind more tightly than ATP ($K_m$=74 µM) by competitively inhibiting both ATP and phosphopeptide binding.

Figure 4:
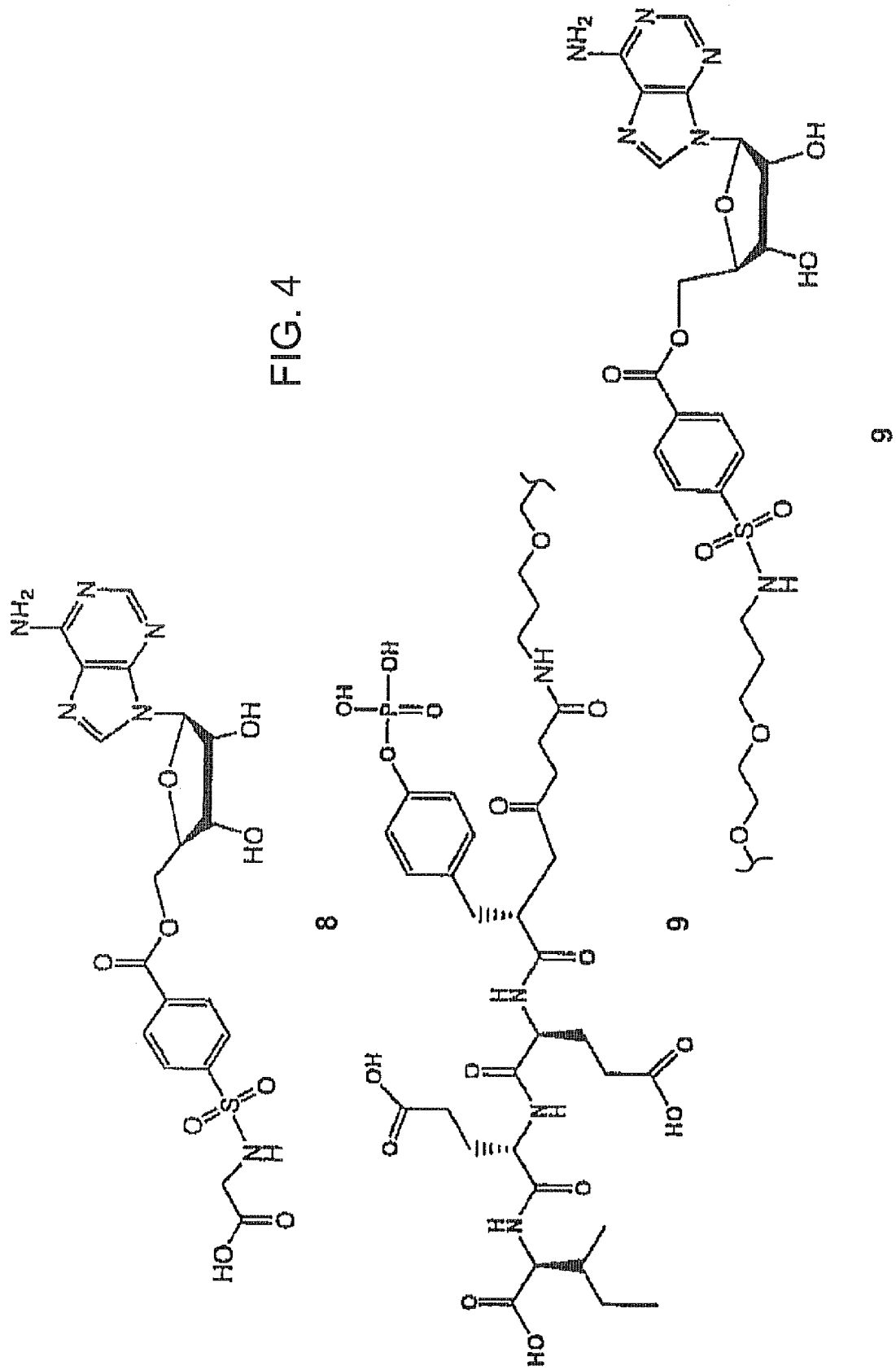
FIG. 4 shows chemical structures for 4-(carboxymethylsulfamoyl)benzoyladenosine (8) and synthesized 4-(sulfamoyl)benzoyladenosine-pYEEI (SEQ ID NO: 3) (SBA-pYEEI) (SEQ ID NO: 3) conjugate (9) as control compounds with no binding affinity to ATP-binding site.

To understand the role and importance of ATP moiety in the whole inhibition effect, an adenosine analog (8) and a control pYEEI-adenosine conjugate (SEQ ID NO: 3) (9), in which the ATP was replaced with 4-(sulfamoyl)-benzoyladenosine (SBA), an uncharged adenosine derivative, were synthesized (FIG. 4). Ac-PYEEI (SEQ ID NO: 3) and adenosine derivative 8, and control pYEEI (SEQ ID NO: 3) conjugate with SBA scaffold (9) were evaluated against Src tyrosine kinase. Ac-pYEEI (SEQ ID NO: 3) had a $K_i$ value of 141.4 µM for polyE$_4$Y phosphorylation that is almost 2 fold higher than $K_m$ for ATP (74 µM) at similar conditions suggesting that this tetrapeptide enhances the catalytic activity. Adenosine derivative (8) and SBA-pYEEI conjugate (SEQ ID NO: 3) (9) did not exhibit any binding affinity to ATP-binding site at maximum tested concentration ($IC_{50}$>300 µM), thereby they represent compounds with no binding affinity for ATP-binding site. It was found that the SBA-pYEEI (SEQ ID NO: 3) conjugates 9 enhanced the catalytic activity and phosphorylation by at least 40%, possibly by activating enzyme through releasing pTyr527 binding with the Src SH2 domain. These results are in agreement with earlier reports indicating that some of the Src SH2 domain inhibitors enhance the catalytic activity.

Chemistry

Figure 5:
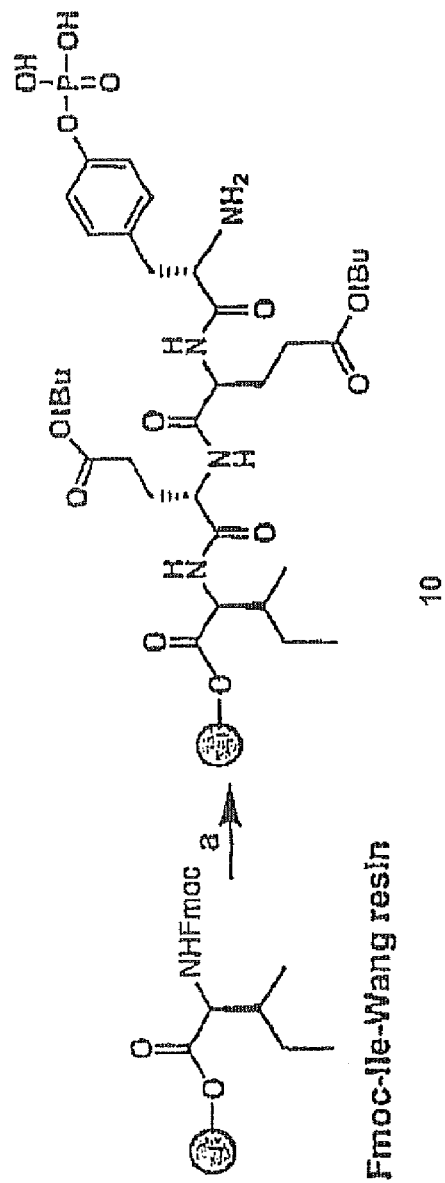
FIG. 5 shows the general synthetic strategy for the preparation of ATP-phosphopeptide conjugates (1-6)
Figure 5:
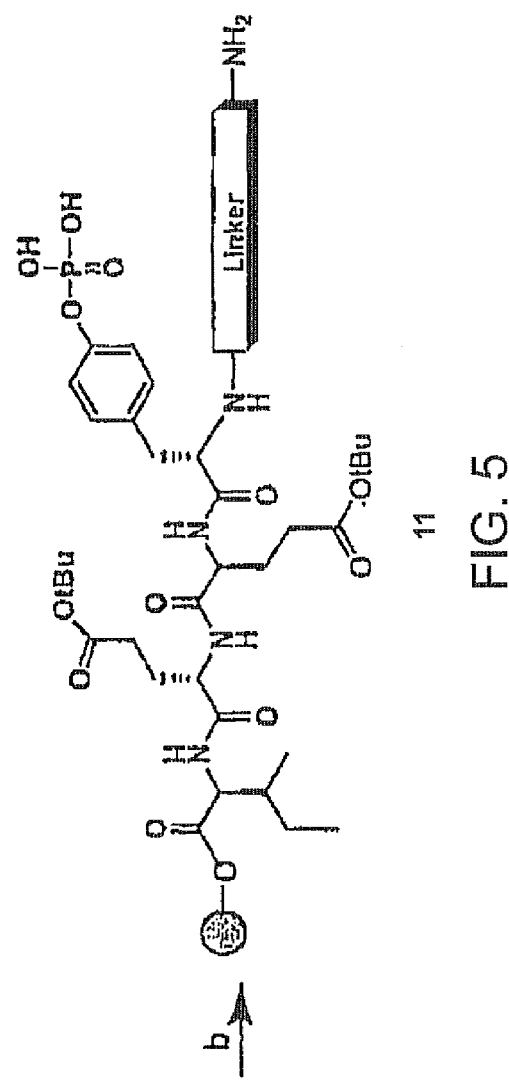
Figure 5:
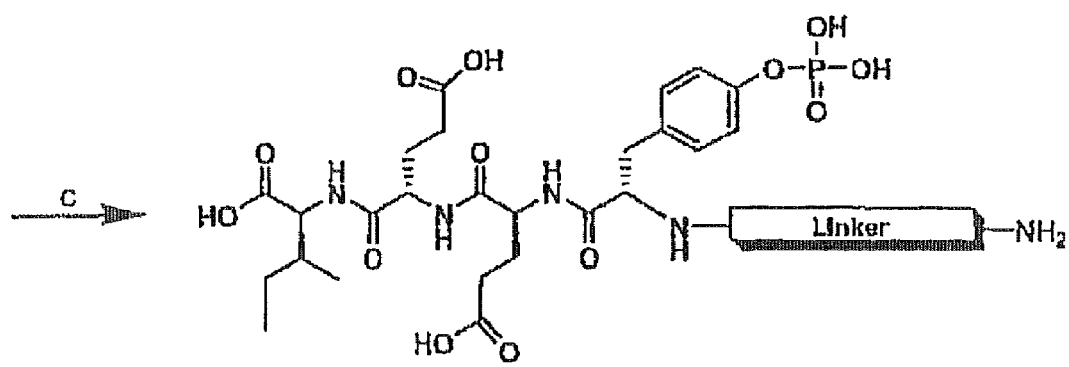
Figure 5:
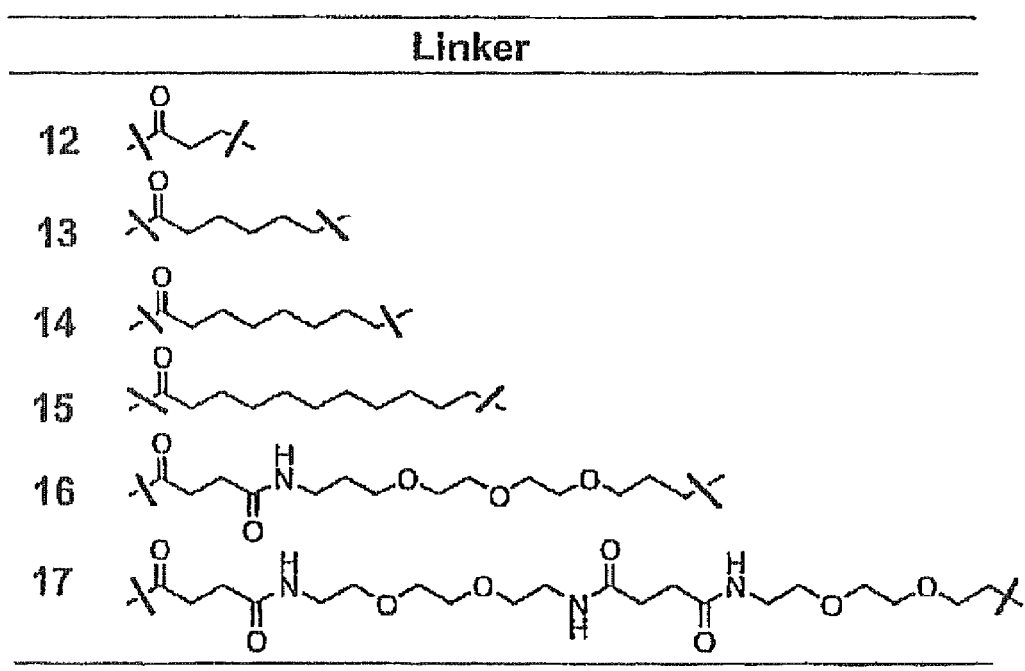
Figure 5:
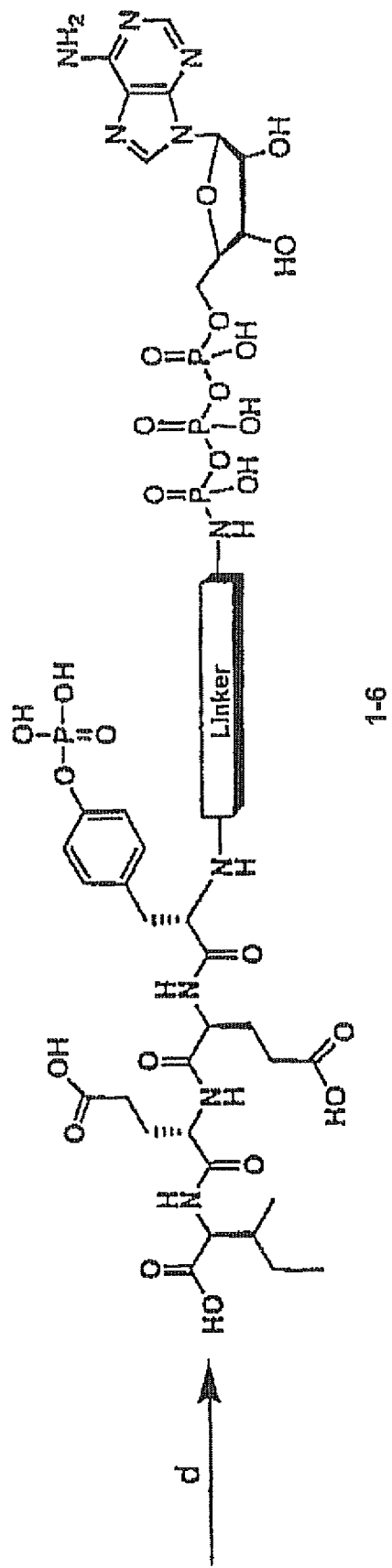

The synthesis of ATP-phosphopeptide conjugates (1-6) were carried out as shown in FIG. 5. The protected SH2-directed phosphopeptides were synthesized on Fmoc-Ile-Wang-resin, utilizing a standard Fmoc (N-(9-fluorenyl)methoxycarbonyl) solid-phase protocol in the presence of HBTU, N-methylmorpholine (NMM), and piperidine to afford 10. The phosphopeptide-attached resin 10 underwent coupling reaction with N-Fmoc protected amino acids (HOOC-(A)-NHFmoc; A=flexible alkyl groups) or succinic anhydride followed by HOOC-(A)-NHFmoc to yield 11. The phosphopeptide-attached linkers (12-17) were cleaved from the resin 11 and deblocked with trifluoroacetic acid (TFA), and then purified by preparative reversed-phase high performance liquid chromatography (HPLC) on a C18 column, utilizing a linear gradient of CH$_3$CN/H$_2$O containing 0.1% TFA. Final conjugation with adenosine 5'-triphosphate sodium salt (ATP) was carried out in the presence of N-cyclohexyl-N'-(2-morpholinoethyl)carbodiimide methyl-p-toluene sulfonate (CMD-CDI) at pH 7 to yield 1-6. High resolution electrospray mass spectrometry was used to confirm the identity of the final products.

Figure 6:
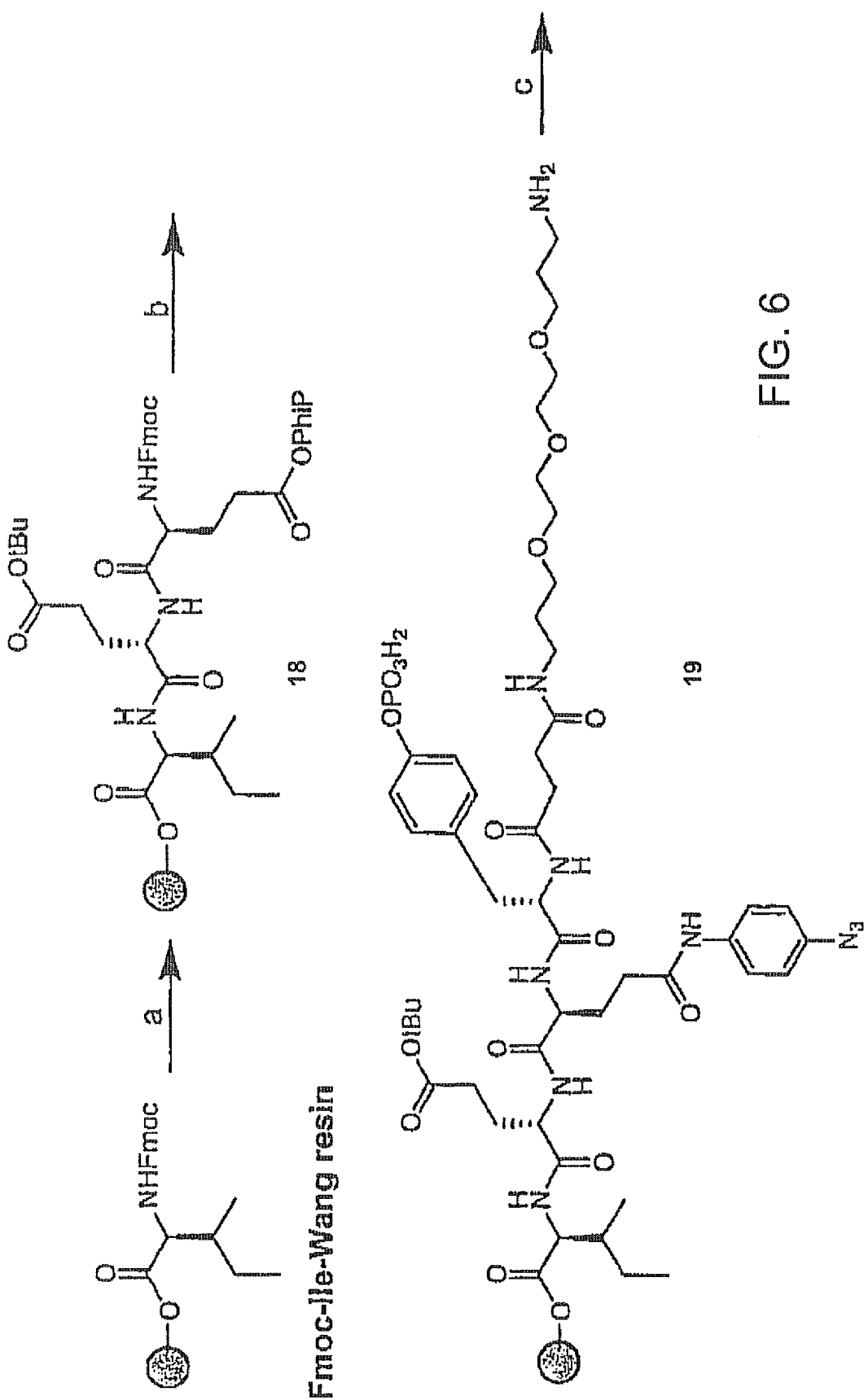
FIG. 6 shows the synthesis of diazido ATP-phosphopeptide conjugate 7.
Figure 6:
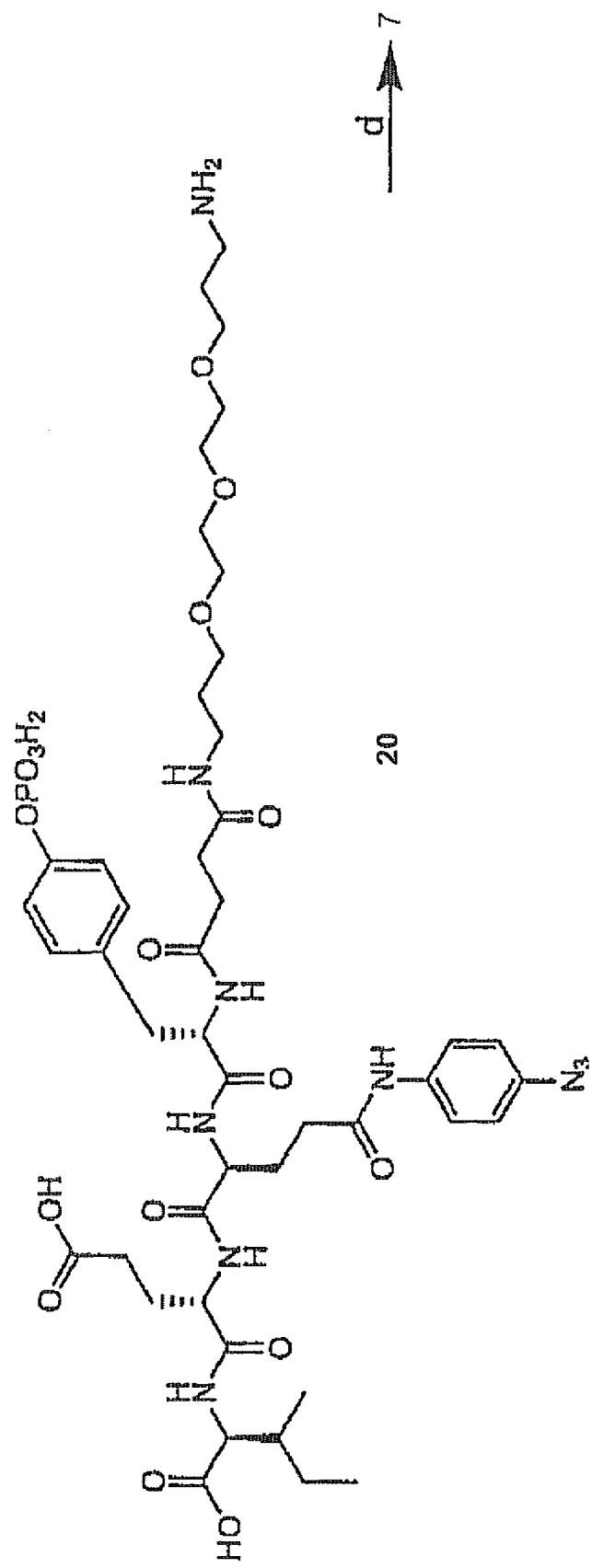

FIG. 6 displays the synthesis of the diazido ATP-phosphopeptide conjugate 7. Fmoc solid-phase peptide synthesis on Ile-Wang resin was carried out using Fmoc-Glu(tBu)-OH and Fmoc-Glu(PhiPr)-OH as protected amino acids to yield 18. The deprotection of PhiPr group on the γ-carboxylic moiety of the β-glutamic acid with TFA/DCM/TIPS followed by reaction with p-azidoaniline and NMM in dark condition, and subsequent coupling reactions with Fmoc-Tyr(PO$_3$H$_2$)— OH, succinic anhydride, and 4,7,10-trioxa-1,13-tridecanediamine, respectively, afforded 19. Cleavage of 19 using TFA furnished peptide 20 that was reacted with 8-azidoadenosine 5'-triphosphate disodium salt (8-Azido-ATP) in the presence of CMD-CDI at pH 7 to yield the diazido ATP-phosphopeptide conjugate 7.

Synthesis of Bisubstrate Analogs Containing ATP-Mimic and Phosphopeptide Mimic.

Figure 7:
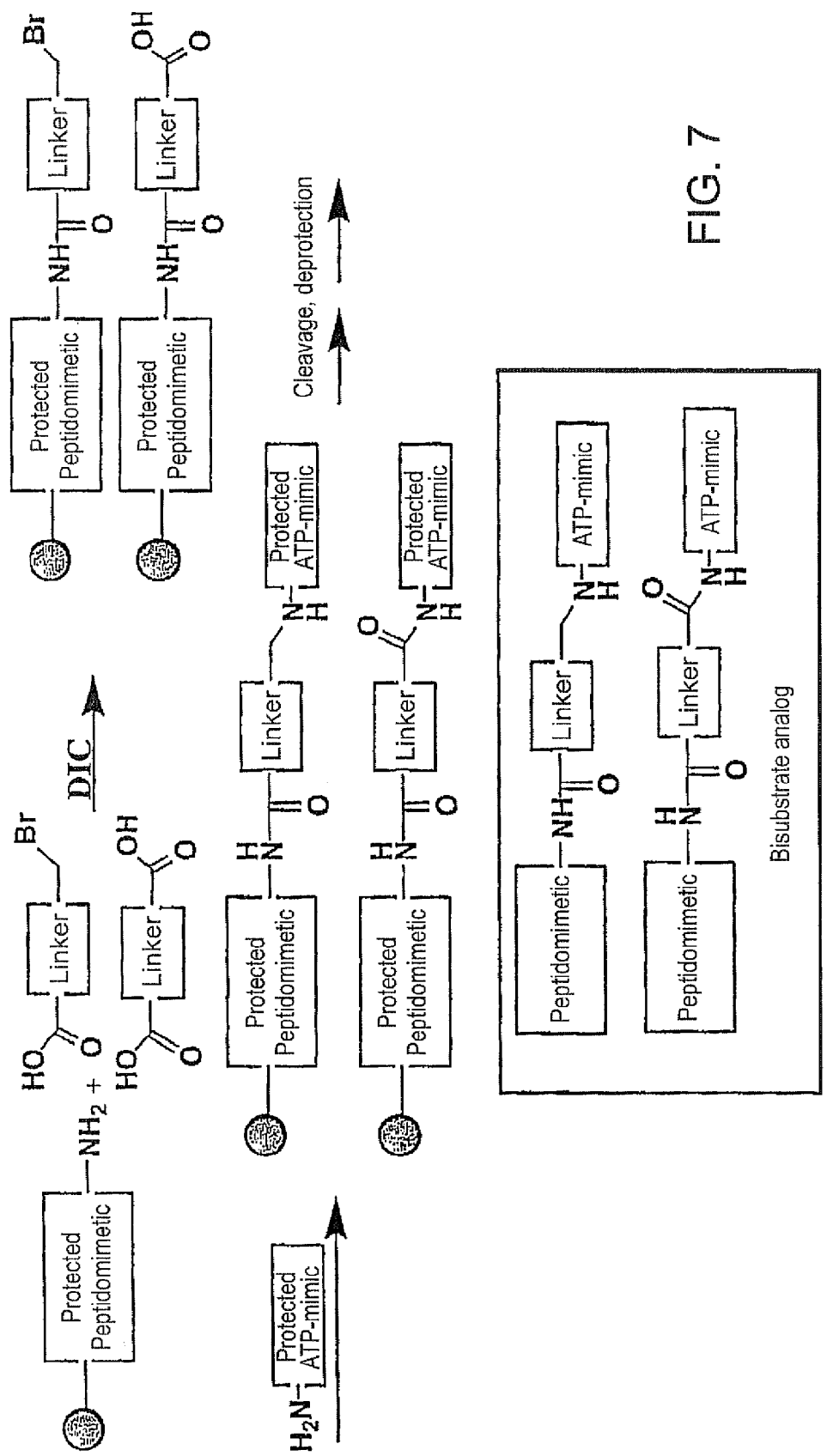
FIG. 7 shows general synthetic strategy for the synthesis of class 1 bisubstrate analogs containing peptidomimetic and ATP mimics.

The general synthetic strategy for is shown in FIG. 7. Some protected peptidomimetics were synthesized on a cleavable solid phase resin and were coupled with a variety of linkers. The synthesis was modified based on the structure of linker. After washing, appropriate protected ATP mimics were attached to the other end of linker in a nucleophilic substitution. The deprotection reaction followed by cleavage from the resin yielded the final products which were purified using preparative HPLC and their identity were confirmed with mass spectrometry and NMR analysis (see FIGS. 11 and 13 for several examples).

Discussion

In general, synthesized ATP-phosphopeptide conjugates may affect Src activity by a variety of mechanisms (A-E) (FIG. 8) including bivalent binding (A), binding to multiple binding sites (B and C), binding of two ATP-phosphopeptide conjugates (each in one binding site) (D), and/or dimer formation (E).

Figure 8:
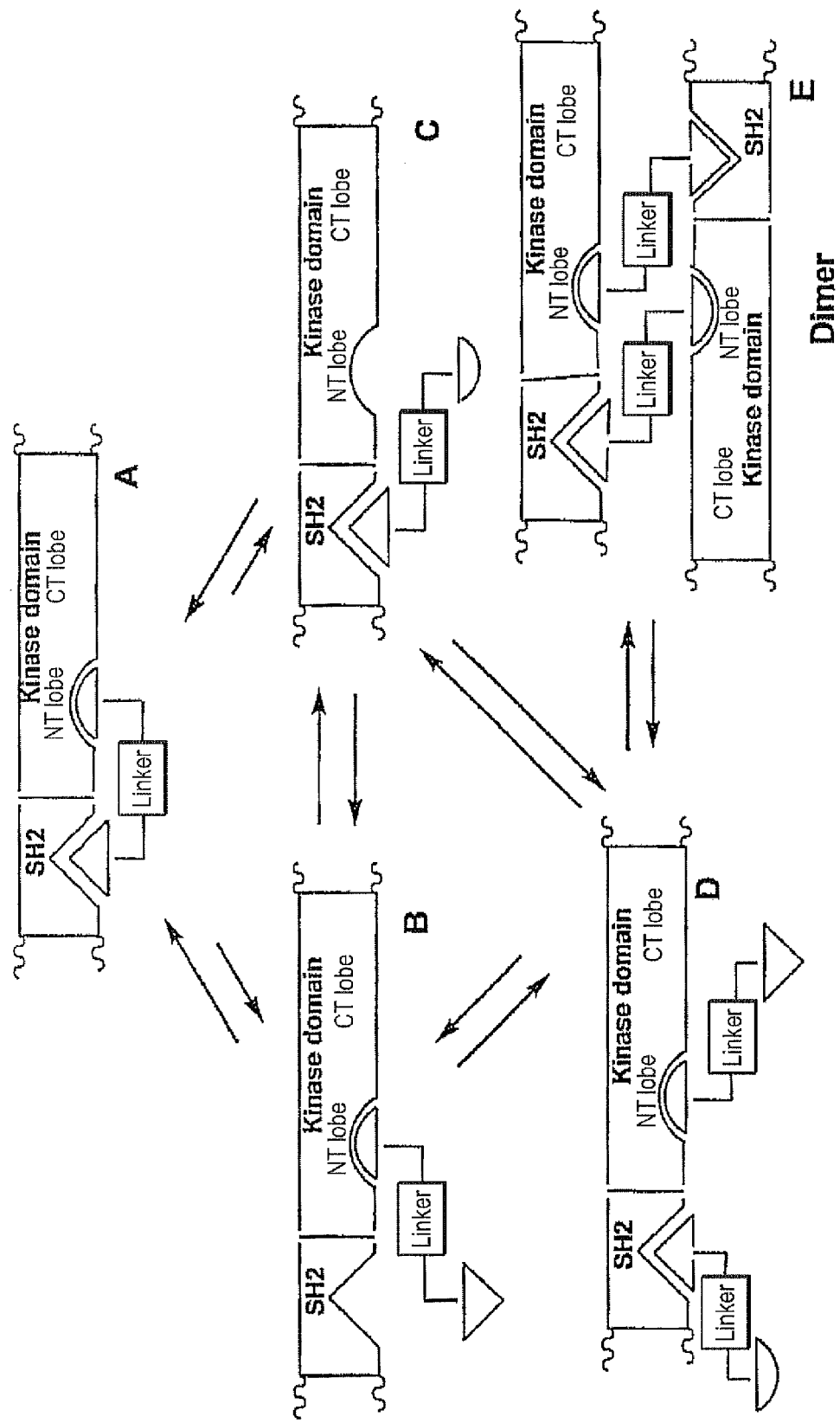
FIG. 8 shows possible mechanisms for the activity of ATP-phosphopeptide conjugates.

The binding affinities of ATP-phosphopeptide conjugates to the SH2 domain alone vs. binding to the SH2 domain in full length Src (KD-Src) for both ATP-phosphopeptide conjugates (1-7) and AcpYEEI (SEQ ID NO: 3) were determined using a fluorescence polarization binding assay. $IC_{50}$ values were assigned to individual compounds according to their competitive binding affinity vs. a high-affinity fluorescent peptide probe, fluorescein-Gly-pTyr-Glu-Glu-Ile-NH$_2$ (SEQ ID NO: 4). ATP-binding site occupation probably occurs after binding of phosphopeptide portion of ATP-phosphopeptide conjugate to the SH2 domain. In other words, only a fraction of ATP-binding site is probably occupied for cooperative binding of pYEEI (SEQ ID NO: 3) to the SH2 domain and for all ATP-phosphopeptide conjugates the mechanism C is the most likely starting point and the mechanism B does not contribute significantly in the inhibition pattern (FIG. 8). This is based on the fact that pYEEI (SEQ ID NO: 3) has higher binding affinity for binding to the SH2 domain than ATP for binding to the ATP-binding site. One could expect since the binding affinity for these conjugates to the Src SH2 domain is higher than the ATP-binding site, a larger population of these inhibitors will occupy the Src SH2 domain (mechanism C) than the ATP-binding site (mechanism B). On the other hand it is possible that two molecules of phosphopeptide-ATP conjugates bind independently from each other to two binding sites in a monovalent pattern (mechanism D) resulting in reducing the catalytic activity.

Figure 9:
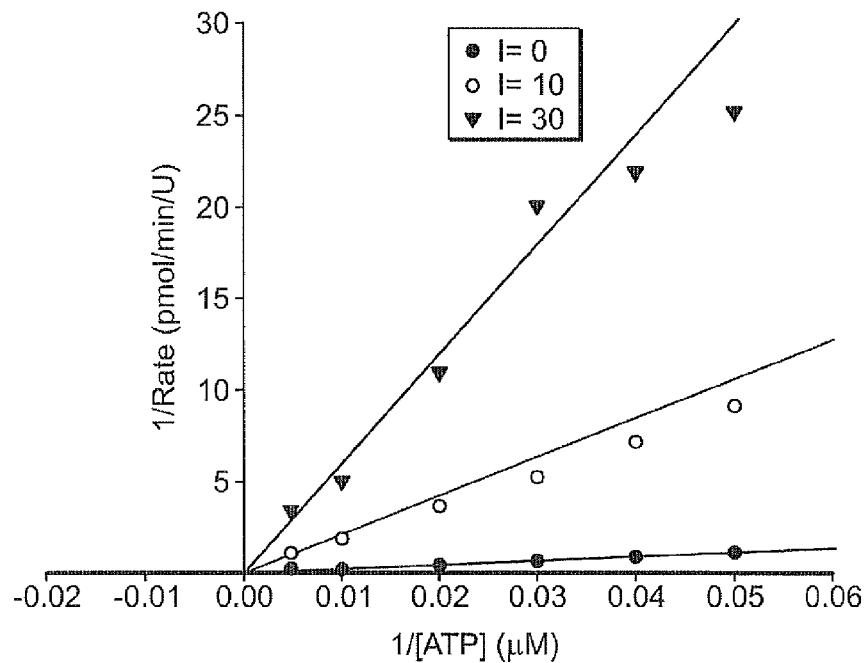
FIG. 9 shows a pattern of inhibition of Src by compound 5; Lineweaver-Burk plot of 1/V vs. 1/ATP with varying concentration of 5 shows linear competitive inhibition ($K_i$=1.7 μm)

On the other hand, two ATP-phosphopeptide conjugates, 5 and 7, exhibited tighter inhibition for ATP-binding site of Src ($K_i$=1.7-2.6). The mechanism of inhibition against ATP by ATP-phosphopeptide conjugate, 5, was determined by steady-state kinetics using a radioactive assay in presence of [γ-$^{32}$P]ATP and different concentrations of ATP. Detailed kinetic studies showed that 5 ($K_i$=1.7 $V_m$=4.1 µmol/min/U) is a competitive inhibitor against ATP [($K_{m, Src}$ (ATP)=74 µM)] (FIG. 9) as shown a linear competitive pattern of inhibition vs. the substrate ATP in double reciprocal plot suggesting that these ATP analogs bind to ATP binding site. ATP-phosphopeptide conjugate 5 was approximately 44 fold more potent than ATP alone suggesting that the binding of pYEEI (SEQ ID NO: 3) scaffold of the molecule to the SH2 domain enhances the binding of the ATP-portion of ATP-phosphopeptide conjugate to the ATP-binding site. Since compound 5 binds tighter to ATP-binding site and the Src SH2 domain, the possibility of bivalent binding (mechanism A) appears the most likely scenario for this ATP-phosphopeptide analog. Similar results were observed for compound 7 having a similar linker length. Compound 5 ($K_{i, Lck}$=25.3 µM) with optimal chain length has about 3.9 fold better binding affinity than ATP for binding to ATP-binding site of Lck.

These data indicate that the linking of the ATP and phosphopeptide binding modules could be effective for the inhibition of kinase activity. ATP-phosphopeptide conjugates with optimal linker size such as compound 5 bind to their targets more tightly than ATP by competitively inhibiting both ATP and phosphopeptide binding.

When the control compound 16 (pYEEI-attached linker (SEQ ID NO: 3), FIG. 5) used alone, the catalytic activity inhibition reduced significantly ($K_i$=608 µM) possibly due to the activation of the enzyme and enhancement of the substrate phosphorylation. Therefore, the incorporation of two substrate moieties targeting the SH2 domain and ATP-binding site in one molecule as seen in the ATP-phosphopeptide conjugate 5 probably contributes to the bivalent inhibition pattern. The distance between two binding sites in the active form of Src is unknown. The conformation of domains and distance between the SH2 domain and ATP-binding site may also change following the binding of bivalent ligands to any two binding pockets in the active form of Src. The tight inhibition and proper orientation of the first module (phosphopeptide) to the SH2 domain in compound 5 probably leads to the orientation and tight binding of the second motif (ATP) to the ATP-binding site resulting in a bivalent inhibition pattern (A). The linkers may assume a loop-like or extended conformation, so that the ATP-binding site-directed fragments associate with ATP-binding site in a structurally compatible fashion.

Cross-linking studies were used to determine whether the dimer formation (mechanism E) contributes to the activity of phosphopeptide-ATP conjugates with optimal linker size by cross-linking of the SH2 domain of one Lck molecule with the ATP-binding site of another Lck. A diazido ATP-phosphopeptide conjugate (7, FIG. 3) was synthesized using 8-azidoATP and a phosphopeptide, in which the azidophenyl group is attached to P+1 amino acid of phosphopeptide (FIG. 6). Although the azido-conjugate has lower affinity to the Src SH2 domain ($IC_{50}$=35.6 µM) probably due to the incorporation of p-azido-phenylamino moiety at P+1 position, the conjugate had a comparable activity with ATP-phosphopeptide conjugate 5 for binding to ATP-binding site ($K_{i, Src}$=2.7 µM, $K_{i, Lck}$=30.0 µM). This conjugate was incubated with whole Lck, irradiated with UV light and subjected to SDS-PAGE electrophoresis. The binding affinity of the conjugate for ATP-binding site did not change significantly after UV exposure ($K_{i, Lck}$=29.8 µM). Only Lck band was observed in all cases indicating the absence of any dimerized product. High molecular weight bands (100 kDa and above) were not observed suggesting that the dimer formation (mechanism E) did not contribute to inhibition by phosphopeptide-ATP analog 7 that had a similar linker to compound 5.

The compounds were more selective against Src than Lck. For example, compounds 5 and 7 ($K_i$=1.7-2.6 µM) showed higher binding affinities to the ATP-binding site of Src relative to Lck ($K_i$=25.3-30.0 µM).

Figure 10:
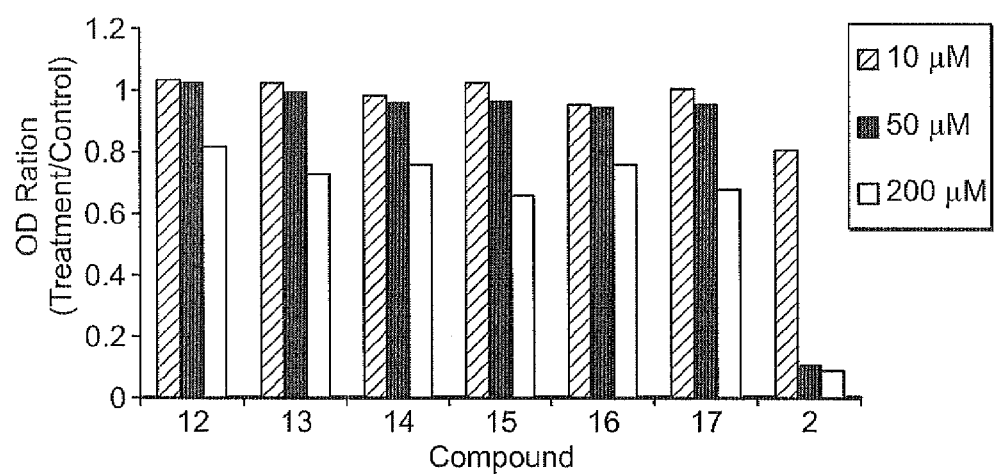
FIG. 10 shows cell proliferation assay [(human embryonic kidney (HEK) 293 tumor cells] for bisubstrate analog 2 and pYEEI (SEQ ID NO: 3) conjugated with long and short chain linkers (12-17)

The ability of several of the bisubstrate analogs to inhibit the growth of cancer cells were assessed in a cell-based proliferation assay in human embryonic kidney (HEK) 293 cells (FIG. 10). The cytotoxicity of these compounds were significant in spite of being charged which may hinder their penetration into cells and having phosphate group which make them susceptible to cleavage by phosphatases in cell culture. Bisubstrate analog 2 significantly inhibited the cell proliferation in this cell line at 50 µM compared to compound without the ATP moiety (12-17) (FIG. 5).

Other Heteroaromatic-Phosphopeptide Conjugates.

Figure 11:
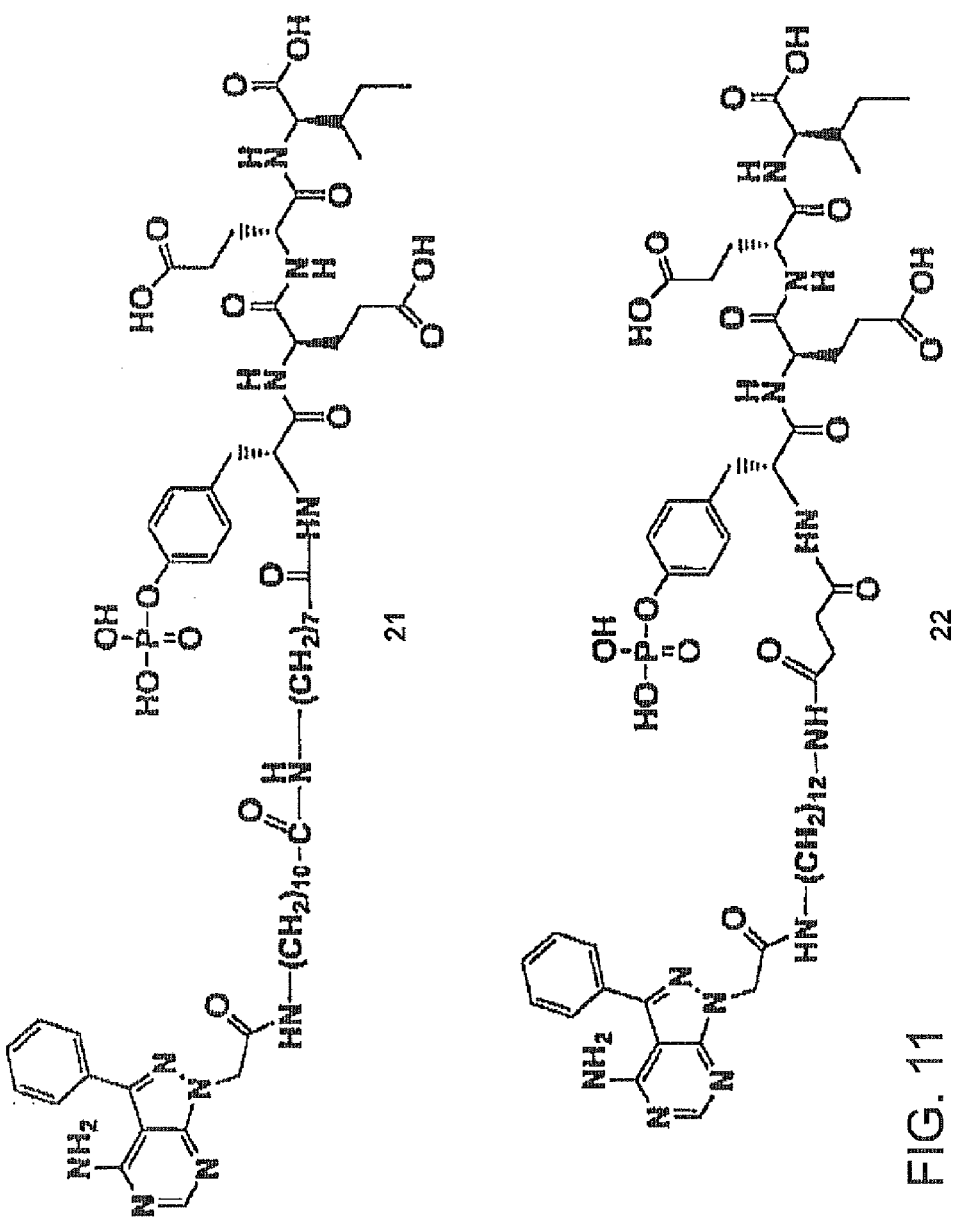
FIG. 11 shows pyrazolopyrimidine-phosphopeptide conjugates as Src kinase inhibitors.
Figure 11:
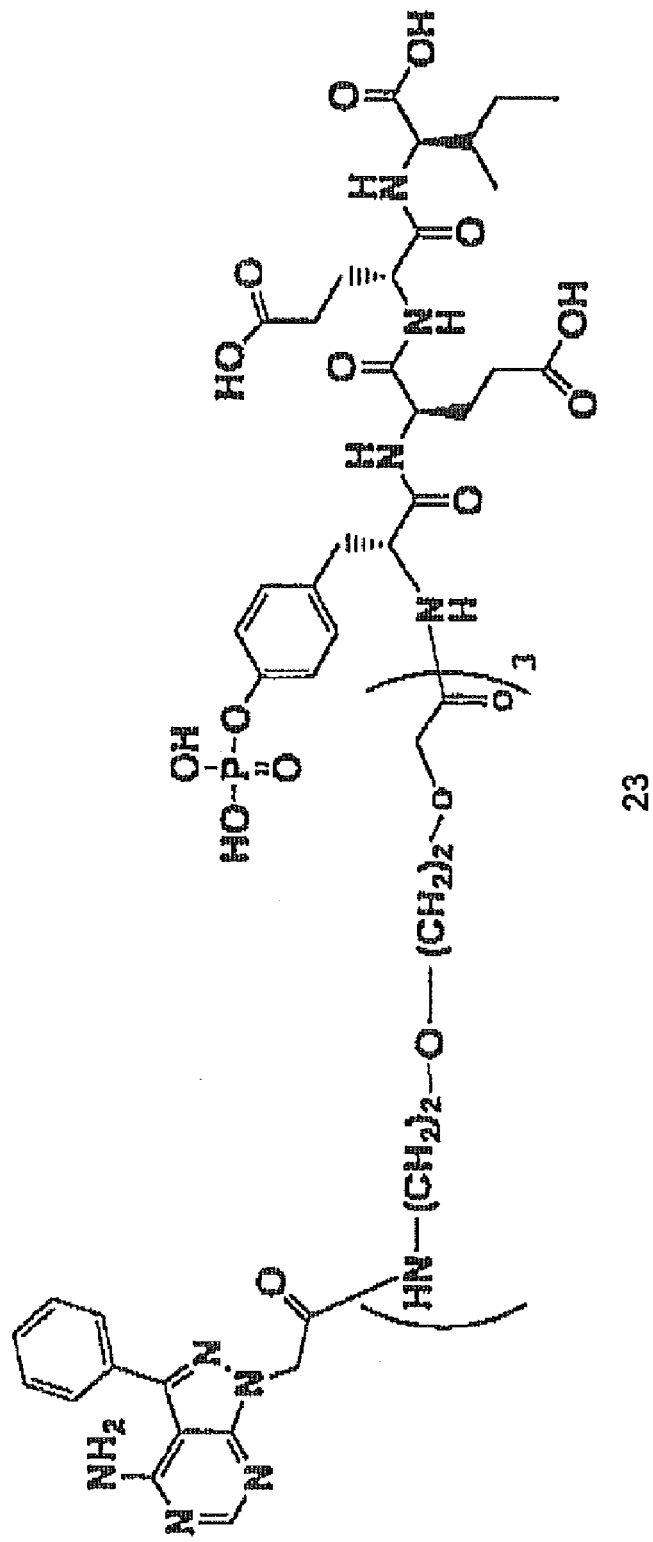

While many of these ATP-phosphopeptide analogs may not have optimal physicochemical properties, they will provide vital mechanistic information for designing compounds with optimal potency. Several other heteroaromatic-phosphopeptide conjugate are disclosed in this invention that have ATP mimics (N-heteroaromatics), including purine-based derivatives, pyrimidine-based derivatives such as 2,4-diamino-5-substituted pyrimidine derivatives, pyrazole[3,4-d] pyrimidine derivatives, pyrrolo[2,3-d]pyrimidine derivatives, pyrido[2,3-d]pyrimidine derivatives, amino-substituted dihydropyrimido [4,5-d]pyrimidinone derivatives, thieno- and furo-substituted derivatives, quinazoline derivatives, quinoline derivatives, and several natural products such as aminogenistein. For example the following three compounds (21-23) were synthesized that have pyrazolopyrimidine in place of ATP and different kinds of linkers (FIG. 11).

It is possible to design and synthesize compounds containing appropriate linkers, ATP mimics, and phosphopeptide mimics to improve bioavailability and introduce selectivity for a specific kinase. Conformational rigidity in the linkers can be introduced for the design of bivalent ligands to avoid the compounds become too floppy in binding to the ATP binding pocket and SH2 domain and to avoid unfavorable entropy loss upon binding.

SH2 domain-directed pTyr mimetics in these conjugates include peptidomimetics, phosphonate-based pTyr mimetics such as phosphonomethylphenylalanine (Pmp) and its analogues, carboxylic acid-based pTyr mimetics such as malonyltyrosine or phenylalanine analogues and their derivatives such as carboxymethyl phenylalanine, uncharged pTyr mimetics, and conformationally constrained peptides.

Figure 12:
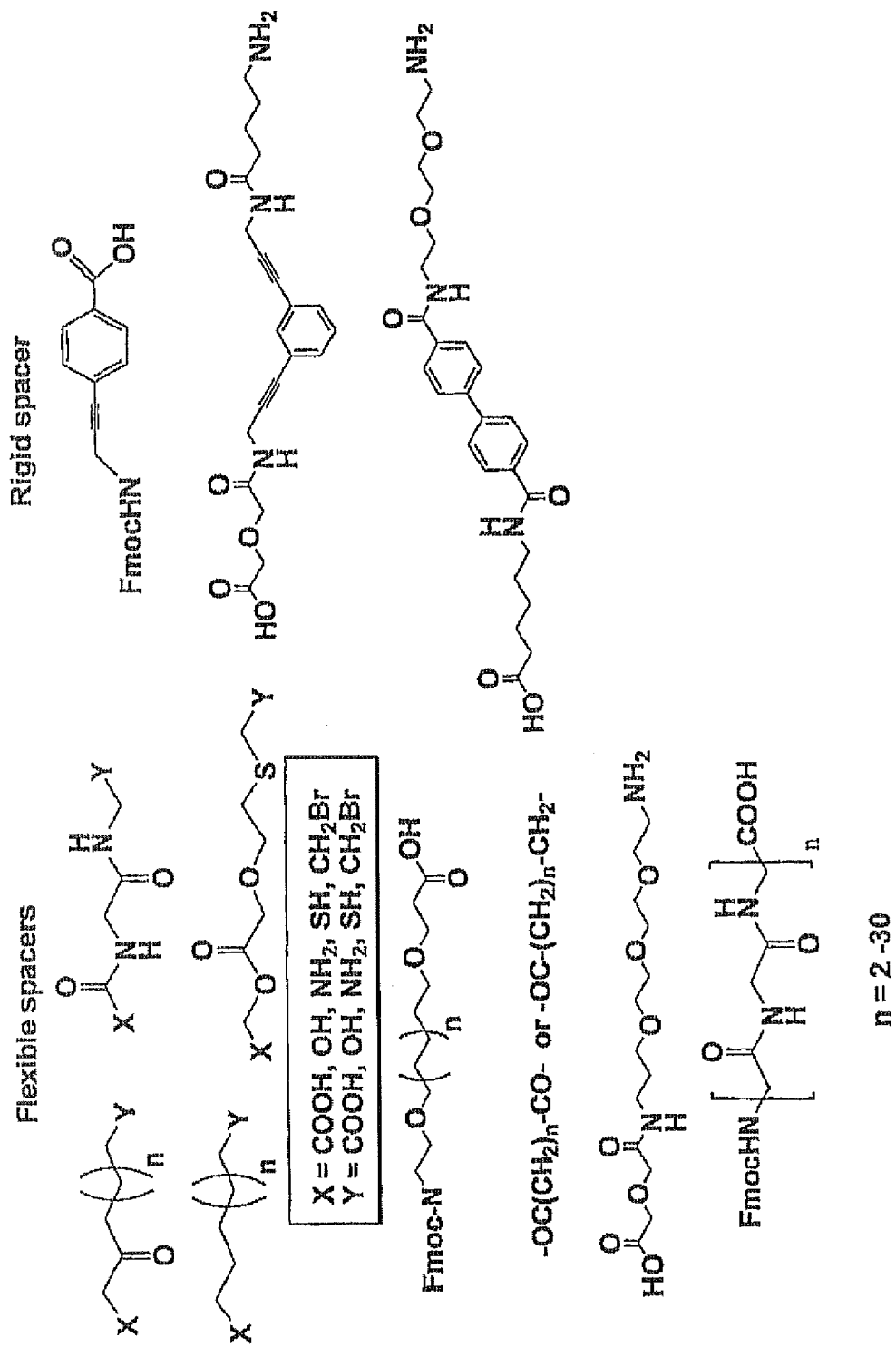
FIG. 12 shows flexible and rigid linkers for designing bisubstrate analogs.

Linkers in these conjugates include alkyl and/or aryl chains of varying length, aminoacyl derivatives [—CO($CH_2$)$_n$NH—, n=2-30]. The linkers may assume a loop-like or extended conformation, so that the nucleotide-binding site- and SH2-directed fragments can associate with their targeted Src kinase regions in a structurally compatible fashion. Some flexible and rigid linkers are shown in FIG. 12. Thus, ATP-selective ligands could be coupled to specific phosphopeptide sequences or SH2 recognition motif to produce bivalent inhibitors with enhanced specificity. Conformational rigidity in the linkers can be changed to avoid the compounds become too floppy in binding to ATP binding pocket and SH2 domain and to avoid unfavorable entropy loss upon binding. The number of flexible or rigid building block can be increased.

Figure 13:
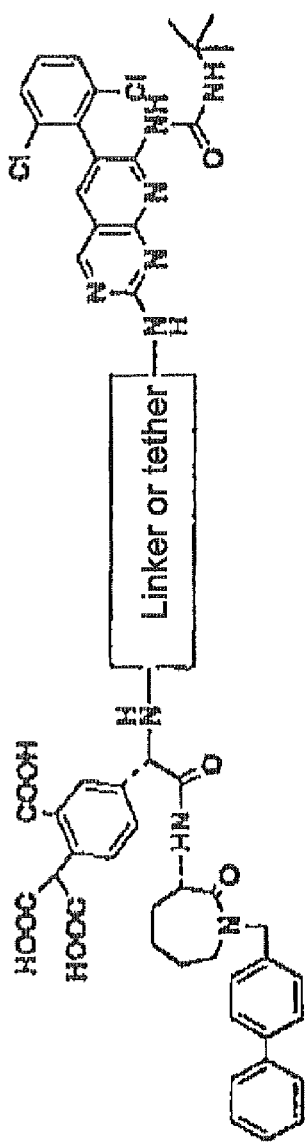
FIG. 13 shows examples of bisubstrate inhibitors having phosphopeptidomimetic and ATP mimic moieties (pYEEI disclosed as SEQ ID NO: 3)
Figure 13:
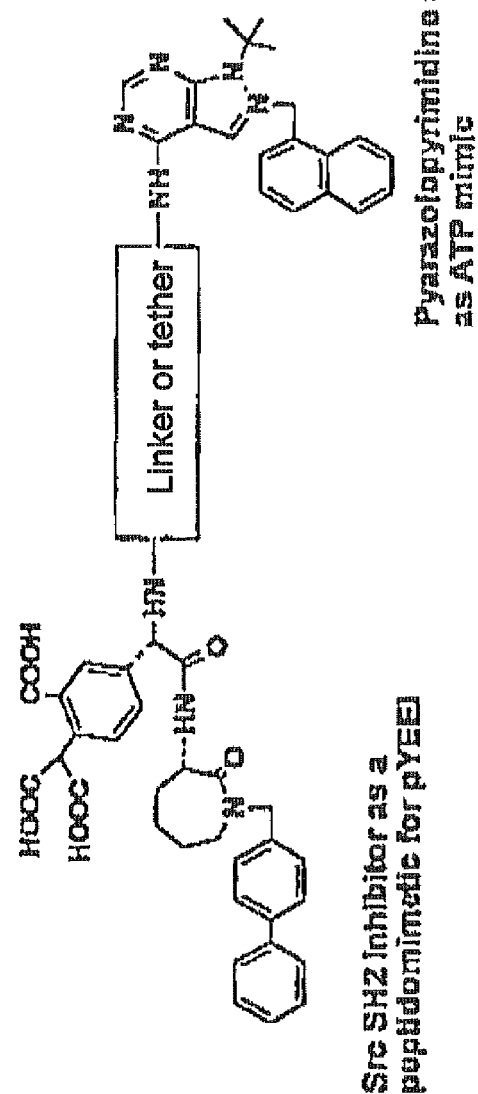
Figure 13:
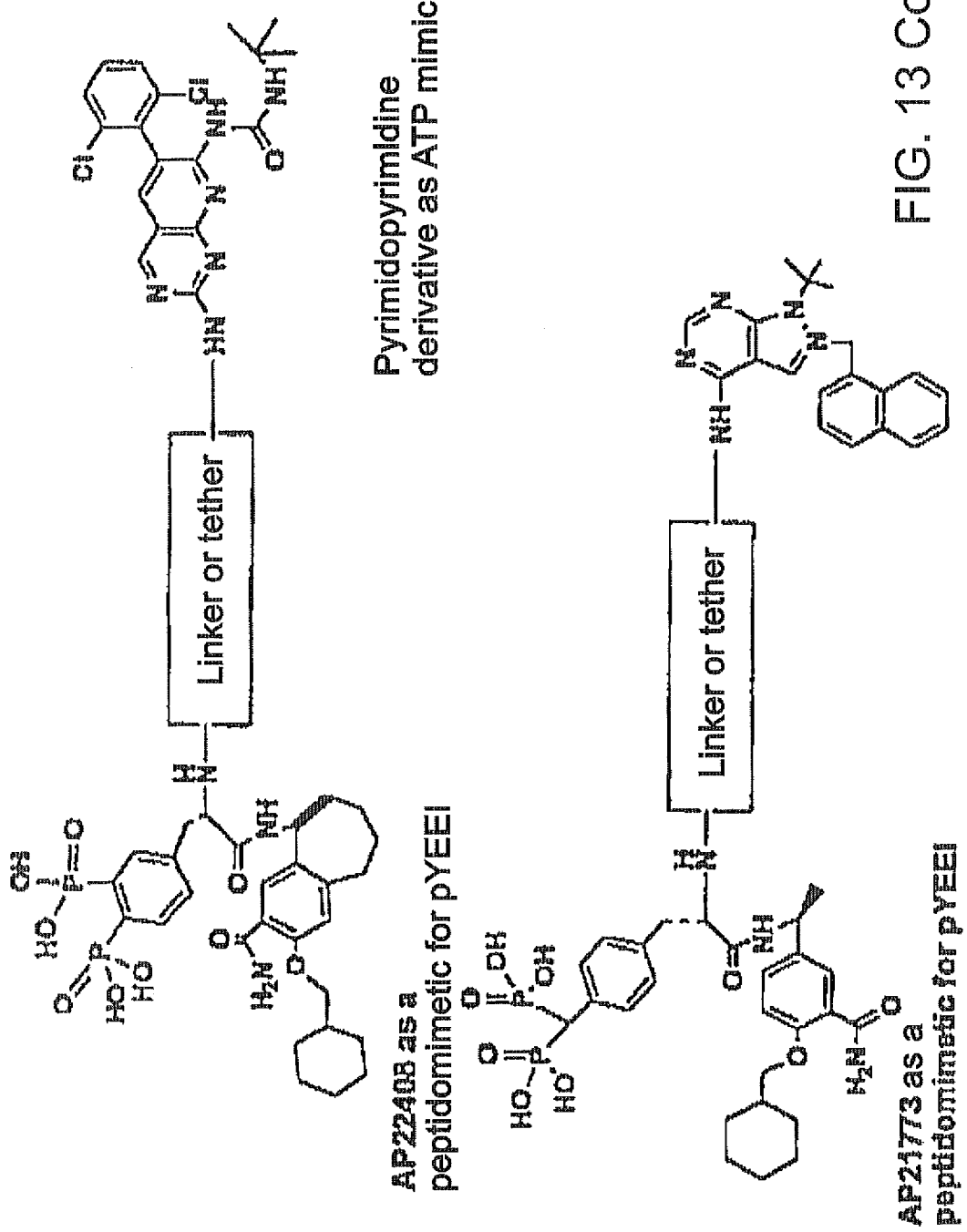
Figure 13:
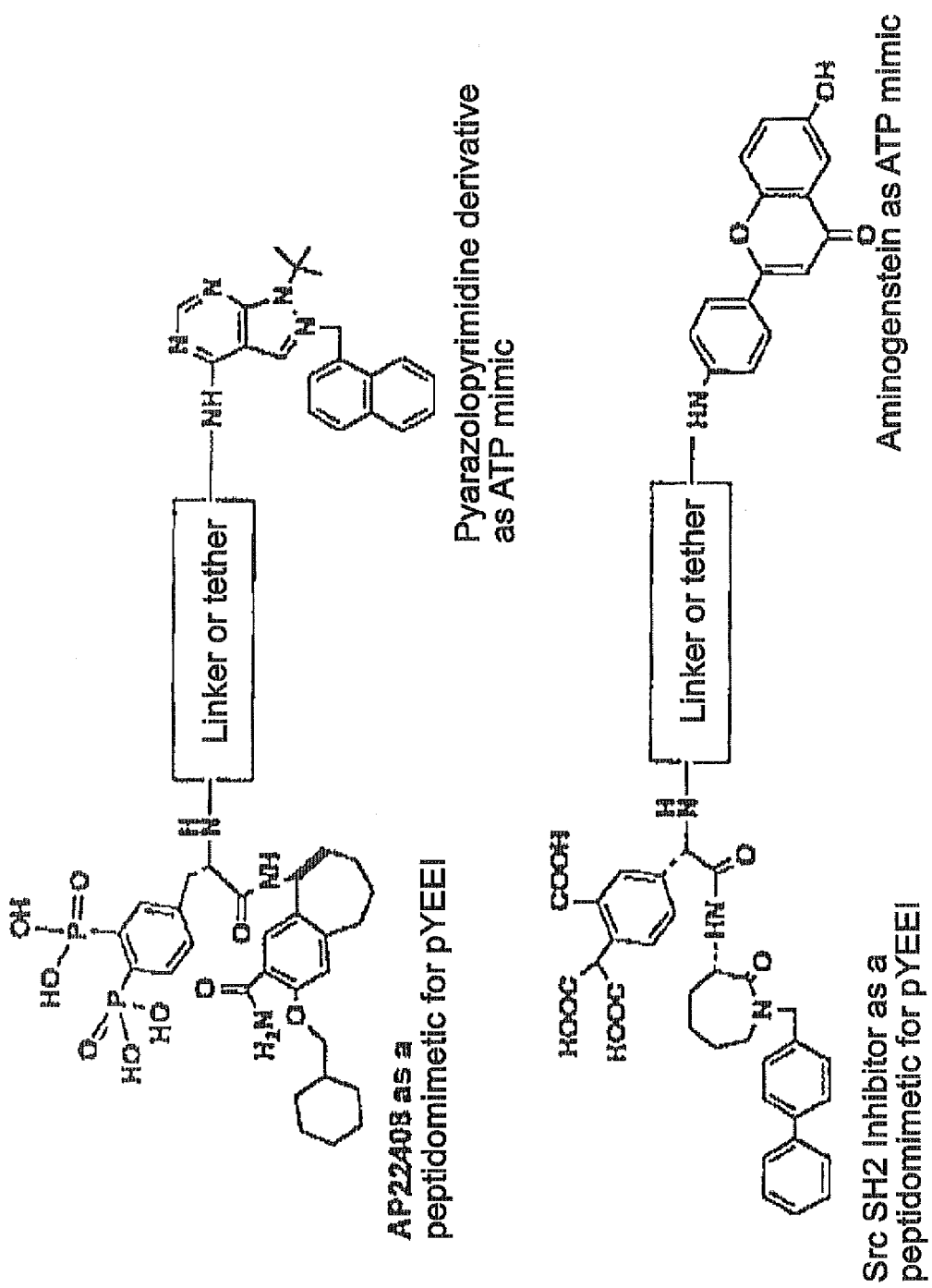
Figure 13:
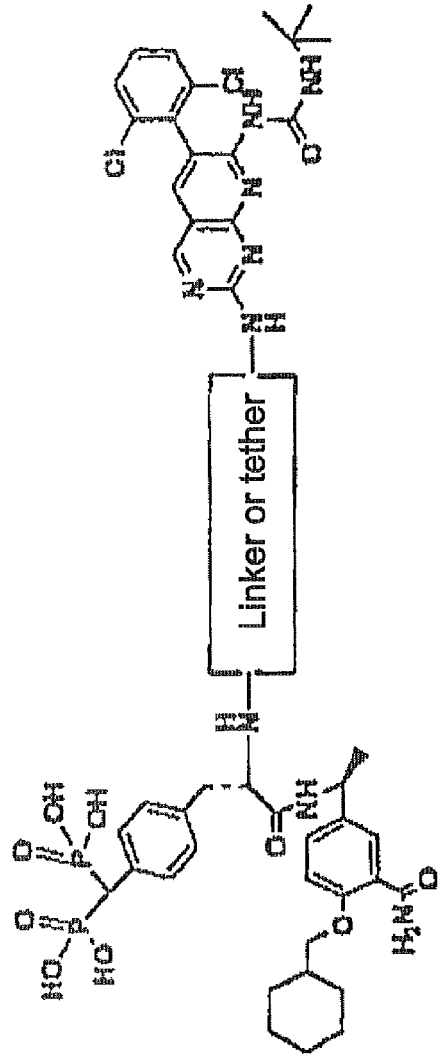
Figure 13:
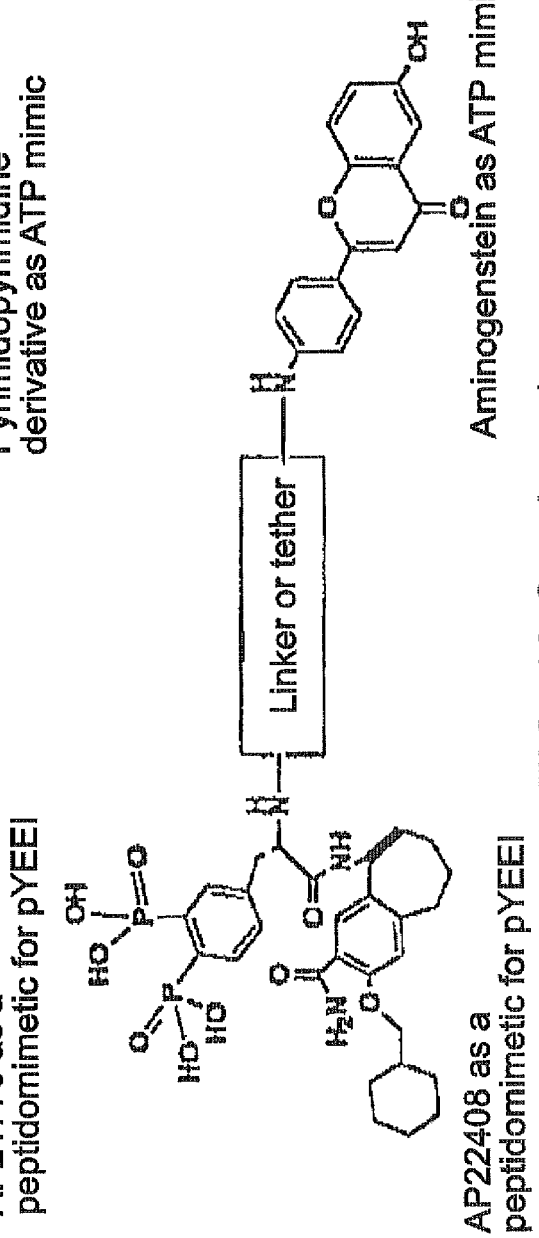
Figure 13:
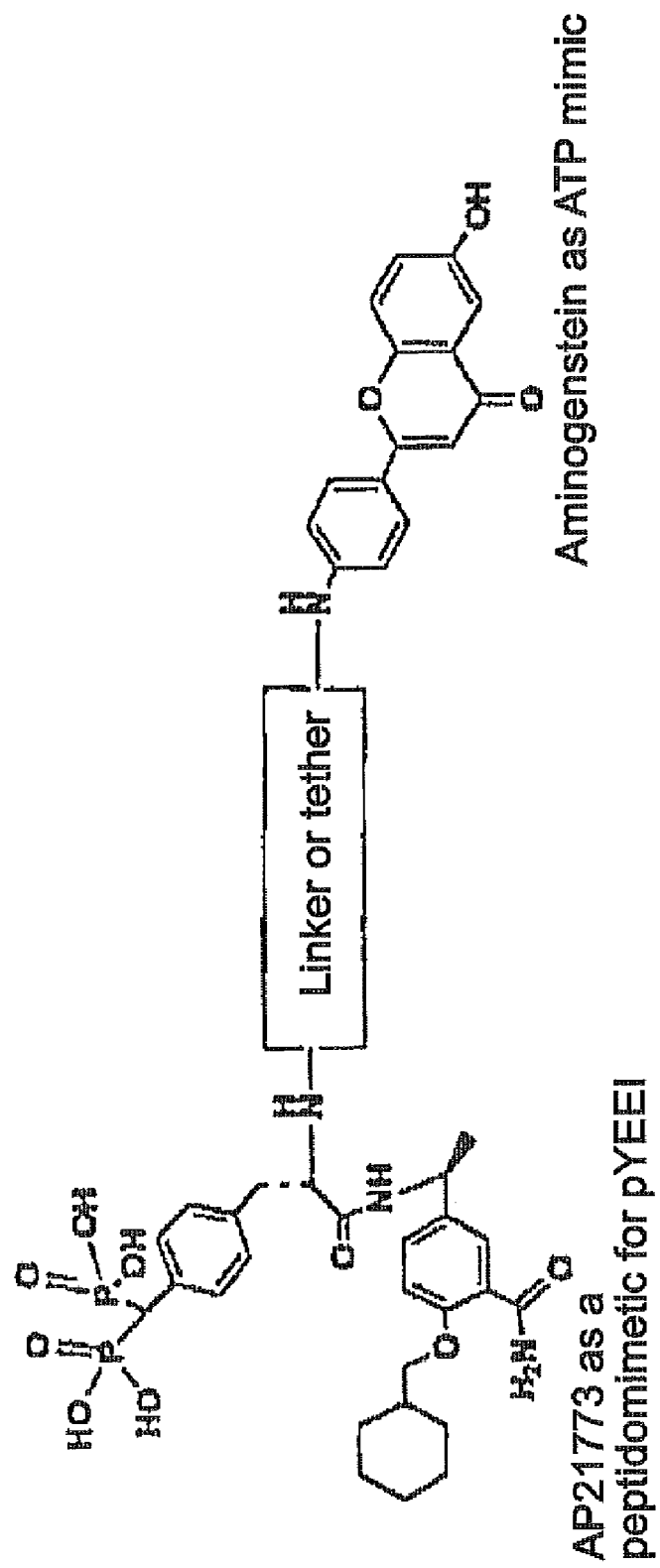

Some of conjugates incorporating the ATP-binding site and SH2 domain recognition motifs are displayed in FIG. 13.

Experimental

General Procedure for the Synthesis and Purification of Peptides

In general, all peptides were synthesized by the solid-phase peptide synthesis strategy on a PS3 automated peptide synthesizer (Rainin Instrument Co., Inc.) employing N-(9-fluorenyl)methoxycarbonyl (Fmoc) based chemistry on 0.1 mmol of Fmoc-Ile-Wang resin (179 mg, loading capacity 0.56 mmol/g) using Fmoc-amino acid building blocks (0.4 mmol). 2-(1H-Benzotriazole-1-yl)-1,1,3,3-tetramethyluronium hexafluorophosphate (HBTU)/1-hydroxybenzotriazole (HOBt) (0.4 mmol), and NMM (0.4 M) in N,N-dimethylformamide (DMF) were used as coupling and activating reagents, respectively. Fmoc-Ile-Wang resin, coupling reagents, and Fmoc-amino acid building blocks, including Fmoc-Tyr($PO_3H_2$)—OH, Fmoc-Glu(tBu)-OH, Fmoc-Glu-OAll, Fmoc-Glu(PhiPr)-OH, and other Fmoc-aliphatic amino acids were purchased from Novabiochem. Other chemicals and reagents were purchased from Sigma-Aldrich Chemical Company (Milwaukee, Wis., USA). Fmoc deprotection at each step was carried out using piperidine in DMF (20%). A mixture of TFA/anisole/water (95:2.5:2.5) was used for side chain deprotection of amino acids and cleavage of the synthesized peptides from the resin. Crude peptides were precipitated by addition of cold diethyl ether (Et$_2$O) and purified by HPLC (Shimadzu LC-8A preparative liquid chromatograph; Shimadzu fraction collector 10A) on a Phenomenex® Prodigy 10 µm ODS reversed-phase column. Peptides were separated by eluting the crude peptide at 4.0 mL/min using a gradient of 0-100% acetonitrile (0.1% TFA) and water (0.1% TFA) over 85 min and were lyophilized. The purity of final products (>95%) was confirmed by analytical HPLC on a Shimadzu 3 µm C-18 column at 0.5 mL/min using the same gradient system. The chemical structures of compounds were confirmed by a high-resolution PE Biosystems Mariner API time of flight mass spectrometer. Details of procedures and spectroscopic data of representative compounds are presented below.

Synthesis of Peptides 12-15.

Peptides were assembled on Fmoc-Ile-Wang resin using automated solid-peptide synthesis (PS3 peptide synthesizer) via the Fmoc strategy using the general synthetic method described above. Cleavage from the resin and purification of the peptide was carried out as described above in the general procedure to yield 12-15 (yields 18-20%). The structures of the peptides were confirmed by electrospray mass spectrometry. 12: H$_2$N-βAla-pTyr-Glu-Glu-Ile-OH (SEQ ID NO: 5): [M]$^+$, calcd. 704.2; found: 705.3 [M+H]$^+$. 13: H$_2$N-6-Ahex-pTyr-Glu-Glu-Ile-OH (SEQ ID NO: 6) (6-Ahex=6-aminohexanoic acid): [M]$^+$, calcd. 745.3; found: 746.2 [M+H]$^+$. 14: H$_2$N-8-Aoct-pTyr-Glu-Glu-Ile-OH (SEQ ID NO: 7) (8-Aoct=8-aminooctanoic acid): [M]$^+$, calcd. 773.3; found: 774.3 [M+H]$^+$. 15: H$_2$N-11-Aund-pTyr-Glu-Glu-Ile-OH (SEQ ID NO: 8) (11-Aund=11-aminoundecanoic acid): [M]$^+$, calcd. 815.4; found: 816.3 [M+H]$^+$.

Synthesis of Peptide H$_2$N-1,13-Trioxa-Suc-pTyr-Glu-Glu-Ile-OH (SEQ ID NO: 9) (1,13-Trioxa=4,7,10-trioxa-1,13-tridecanediamine; Suc=succinoyl) (16).

The peptide sequence pTyr-Glu-Glu-Ile (SEQ ID NO: 3) was assembled on Wang resin (using 0.1 mmol Fmoc-Ile-Wang resin). The Fmoc group on the N-terminal of the p-Tyr moiety was removed using piperidine in DMF (20%, 5 mL×2). The resin was washed with acetic acid in DMF (1%, 50 mL), TEA in DMF (1%, 50 mL), and DMF (50 mL), followed by MeOH (50 mL) and DCM (50 mL), respectively. The obtained resin was completely dried under vacuum, then suspended in dry DMF (5 mL), to which an excess of succinic anhydride (300 mg, 3 mmol) was added. The suspension was mixed for 2 h at room temperature. The solvent was removed by filtration and the resin was washed with TEA in DMF (1%, 50 mL), DMF (50 mL), MeOH (50 mL), and DCM (50 mL), respectively. The resin was then dried under vacuum overnight and suspended in dry DMF (5 mL). To the swelled resin, HBTU (150 mg, 0.4 mmol) was added, followed by 4,7,10-trioxa-1,13-tridecanediamine (176 µL, 0.8 mmol). The resulting suspension was mixed at room temperature for 3 h, then the solvent was filtered off. The resin was washed with DMF (50 mL), MeOH (50 mL), DCM (50 mL), respectively, and dried under vacuum for 30 min. Cleavage of the peptide from the resin and subsequent purification were carried out as described in the general procedure to yield 16 (20%). The identity of the peptide was confirmed by electrospray mass spectrometry. [M]$^+$, calcd. 934.4; found: 935.3 [M+H]$^+$.

Synthesis of Peptide (H$_2$N-1,8-Diam-Suc-1,8-Diam-Suc-pTyr-Glu-Glu-Ile-OH (SEQ ID NO: 10) (1,8-Diam=1,8-diamino-3,6-dioxaoctane; Suc=succinoyl) (17).

The peptide sequence pTyr-Glu-Glu-Ile (SEQ ID NO: 3) was assembled on Wang resin (using 0.1 mmol Fmoc-Ile-Wang resin). The Fmoc group on the N-terminal of the pTyr moiety was removed using piperidine in DMF (20%, 5 mL×2). The resin was washed with acetic acid in DMF (1%, 50 mL), TEA in DMF (1%, 50 mL), and DMF (50 mL), MeOH (50 mL), and DCM (50 mL), respectively. The obtained resin was completely dried under vacuum, then suspended in dry DMF (5 mL), to which an excess of succinic anhydride (300 mg, 3 mmol) was added. The suspension was mixed for 2 h at room temperature. The solvent was removed by filtration and the resin was washed with TEA in DMF (1%, 50 mL), and DMF (50 mL), MeOH (50 mL), and DCM (50 mL), respectively. The resin was dried under vacuum overnight and suspended in dry DMF (5 mL). To the swelled resin in DMF was added HBTU (150 mg, 0.4 mmol), followed by 1,8-diamino-3,6-dioxaoctane (100 µL, 0.8 mmol). The resulting suspension was mixed at room temperature for 3 h, then the solvent was filtered off. The resin was washed with DMF (50 mL), MeOH (50 mL), DCM (50 mL), respectively, and dried under vacuum overnight. Coupling of succinic anhydride and 1,8-diamino-3,6-dioxaoctane was repeated again for one more cycle as described above. Cleavage of the peptide from the resin and subsequent purification were carried out as described above in the general procedure to yield 17 (18%). The identity of the peptide was confirmed by electrospray mass spectrometry. [M]$^+$, calcd. 1092.5; found: 1093.4 [M+H]$^+$.

Synthesis of ATP-Phosphopeptide Conjugates

Synthesis of ATP-βAla-pTyr-Glu-Glu-Ile-OH (SEQ ID NO: 5) (1).

Adenosine 5'-triphosphate disodium salt (30 mg, 54.3 µmol) was dissolved in distilled water (5 ml) and the pH of the solution was brought to 7 (using pH paper indicator) by titrating with sodium hydroxide (1 M). N-Cyclohexyl-N'-(2-morpholinoethyl)carbodiimide methyl-p-toluene sulfonate (382 mg, 0.90 mmol) and additional water (1 ml) were added to the reaction mixture. The pH of solution was brought down to 5.6 with HCl (1 M) and maintained in a pH range between 5.6 and 5.8 throughout the reaction as determined by pH paper. Peptide 12 (15 mg, 21.6 µmol) dissolved in DMF (1 mL) was added to the solution and the reaction mixture was titrated back to pH 5.6-5.8 with sodium hydroxide (1 M). The reaction was left stirring for an additional 4 h and then treated with triethylamine to reach pH 8.5. The mixture was purified on a DEAE Sephadex-A25 anion exchange column with pH 8 triethylammonium bicarbonate (TEAB) buffer. Briefly, a Sephadex DEAE A25 (6 g) was swelled in water, placed into a column, washed with water (100 ml), TEAB (1M, 100 ml) and again water (175 ml). A gradient system was used for purifications (A=water, B=TEAB 1 M) using a flow rate of 3 ml/min and fraction sizes of 6 ml at 4° C.; gradient: 0-60 ml, B (0%); 60-260 ml, B (0-40%), 260-360 ml, B (40-100%). Compound 1 was eluted in 60% TEAB (9.2 mg, 35.7%). MS (ESI) [M]$^+$, calcd. 1192.2; found: 1193.3 [M+H]$^+$, 1214.2 [M+Na]$^+$, 1292.2 [M+TEA]$^+$, 1392.2 [M+2TEA]$^+$.

Synthesis of ATP-6-Ahex-pTyr-Glu-Glu-Ile-OH (SEQ ID NO: 6) (2).

A similar strategy as described above for the preparation and purification of ATP-phosphopeptide conjugate 1 was used using adenosine 5'-triphosphate disodium salt (35 mg, 63.7 µmol), N-cyclohexyl-N'-(2-morpholinoethyl)carbodiimide methyl-p-toluene sulfonate (382 mg, 0.90 mmol) and peptide 13 (20 mg, 26.9 µmol). Compound 2 was eluted in 60% TEAB (7.3 mg, 21.9%). MS (ESI) [M]$^+$, calcd. 1234.2; found: 1235.3 [M+H]$^+$, 1256.2 [M+Na]$^+$, 1334.5 [M+TEA]$^+$, 1434.4 [M+2TEA]$^+$.

Synthesis of ATP-8-Aoct-pTyr-Glu-Glu-Ile-OH (SEQ ID NO: 7) (3).

A similar strategy as described above for the preparation of ATP-phosphopeptide conjugate 1 was used using adenosine 5'-triphosphate disodium salt (35 mg, 63.7 μmol), N-cyclohexyl-N'-(2-morpholinoethyl)carbodiimide methyl-p-toluene sulfonate (382 mg, 0.90 mmol) and peptide 14 (23 mg, 29.7 μmol). Compound 3 was eluted in 60% TEAB (6.5 mg, 17.3%). MS (ESI) $[M]^+$, calcd. 1262.3; found: 1263.3 $[M+H]^+$, 1306.3 $[M+Na]^+$, 1334.5 $[M+TEA]^+$, 1372.3 $[M+5Na]^+$, 1450.4 $[M+4Na^+ TEA]^+$.

Synthesis of ATP-11-Aund-pTyr-Glu-Glu-Ile-OH (SEQ ID NO: 8) (4).

A similar strategy as described above for the preparation of ATP-phosphopeptide conjugate 1 was used using adenosine 5'-triphosphate disodium salt (35 mg, 63.7 μmol), N-cyclohexyl-N'-(2-morpholinoethyl)carbodiimide methyl-p-toluene sulfonate (382 mg, 0.90 mmol) and peptide 15 (21 mg, 25.7 μmol). Compound 4 was eluted in 65% TEAB (7.1 mg, 21.2%). MS (ESI) $[M]^+$, calcd. 1304.5; found: 1305.5 $[M+H]^+$, 1326.3 $[M+Na]^+$, 1404.5 $[M+TEA]^+$, 1504.5 $[M+2TEA]^+$.

Synthesis of ATP-1,13-Trioxa-Suc-pTyr-Glu-Glu-Ile-OH (SEQ ID NO: 9) (5).

A similar strategy as described above for the preparation of ATP-phosphopeptide conjugate 1 was used using adenosine 5'-triphosphate disodium salt (40 mg, 72.8 μmol), N-cyclohexyl-N'-(2-morpholinoethyl)carbodiimide methyl-p-toluene sulfonate (382 mg, 0.90 mmol) and peptide 16 (25 mg, 26.7 μmol). Compound 5 was eluted in 65-70% TEAB (5.7 mg, 14.9%). MS (ESI) $[M]^+$, calcd. 1423.4; found: 1424.4 $[M+H]^+$, 1445.4 $[M+Na]^+$, 1523.4 $[M+TEA]^+$, 1623.4 $[M+2TEA]^+$.

Synthesis of ATP-1,8-Diam-Suc-1,8-Diam-Suc-pTyr-Glu-Glu-Ile-OH (SEQ ID NO: 10) (6).

A similar strategy as described above for the preparation of ATP-phosphopeptide conjugate 1 was used using adenosine 5'-triphosphate disodium salt (50 mg, 91.1 μmol), N-cyclohexyl-N'-(2-morpholinoethyl)carbodiimide methyl-p-toluene sulfonate (382 mg, 0.90 mmol) and peptide 17 (21 mg, 19.2 μmol). Compound 6 was eluted in 65-70% TEAB (5.2 mg, 16.9%). MS (ESI) $[M]^+$, calcd. 1598.5; found: 1599.4 $[M+H]^+$, 1620.5 $[M+Na]^+$, 1698.5 $[M+TEA]^+$.

Synthesis of 1,13-Trioxa-SA-pTyr-γ-p-azidoGlu-Glu-Ile-OH (20).

The resin-bound peptide 18 (0.1 mmol) was synthesized on Wang resin using an automated peptide synthesizer (PS3) via Fmoc peptide strategy. The resin 18 was suspended in TFA/DCM/TIPS (5/90/5, 5 mL) and the resulting suspension was mixed for 1 h to remove the PhiP (2-phenylisopropyl) protecting group on the γ-carboxylic moiety of the β-glutamic acid. The deprotection was repeated with one more cycle. The resin was washed with DMF (50 mL), MeOH (50 mL), and DCM (50 mL), respectively, and was completely dried under vacuum overnight. The dry resin was suspended in dry DMF (5 mL). To the resulting suspension was added HBTU (153 mg, 0.4 mmol), p-azidoaniline (56 mg, 0.4 mmol), and NMM (100 μL). The reaction mixture was covered with aluminum foil and mixed for 3 h at room temperature. The solvent was filtered off and the resin was washed with DMF (50 mL), MeOH (50 mL), and DCM (50 mL), respectively. The resin was then suspended in piperidine/DMF (20%, 5 mL) and mixed for 5 min to unmask the amino group of the N-terminal. This step was repeated once. The resin was then washed with DMF (50 mL), MeOH (50 mL), and DCM (50 mL), respectively, and dried under vacuum overnight. The unmasked amino group was reacted with excess succinic anhydride (200 mg, 2 mmol) to a suspension of the resin in dry DMF (5 mL) for 3 h at room temperature. The solvent was filtered off and the resin was washed with DMF (50 mL), MeOH (50 mL), and DCM (50 mL), respectively, and dried completely under vacuum. The dry resin was suspended again in dry DMF (5 mL), to which HBTU (153 mg, 0.4 mmol), 4,7,10-trioxa-1,13-tridecanediamine (88 μL, 0.4 mmol), and NMM (100 μL) were added. The mixture was mixed for 3 h at room temperature. After that, the resin was washed with DMF (50 mL), MeOH (50 mL), and DCM (50 mL), and dried under vacuum for 30 min to give the resin-bound peptide 19. Cleavage of 19 using TFA as described in the general section afforded peptide 20 (47 mg, 45%). MS (ESI) $[M]^+$, calcd. 1051.4; found: 1052.4 $[M+H]^+$.

Synthesis of ATP-1,13-Trioxa-SA-pTyr-γ-p-azidoGlu-Glu-Ile-OH (7)

8-Azidoadenosine 5'-triphosphate disodium salt (25 mg, 45.5 μmol) was dissolved in distilled water (5 ml) and the pH of the solution was brought to 7 (using pH paper indicator) by titrating with sodium hydroxide (1 M). N-Cyclohexyl-N-(2-morpholinoethyl)carbodiimide methyl-p-toluene sulfonate (382 mg, 0.90 mmol) was added to the reaction mixture with another 1 ml water. The pH of solution was brought down to 5.6 with HCl (1 M) and maintained in a pH range between 5.6 and 5.8 throughout the reaction as determined by pH paper. Peptide 20 (29 mg, 27.5 mmol) in DMF (1 mL) was added to the solution and the reaction mixture was titrated back to pH 5.6-5.8 with sodium hydroxide (1 M). The reaction was covered with aluminum foil and left stirring for an additional 4 h and then treated with triethylamine to reach pH 8.5. The mixture was purified on a DEAE Sephadex-A25 anion exchange column (covered with aluminum foil) with pH 8 triethylammonium bicarbonate (TEAB) buffer as described above for ATP-phosphopeptide conjugate 1. Compound 7 was eluted in 55-60% TEAB (13.9 mg, 32.0%). MS (ESI) $[M]^+$, calcd. 1580.4; found: 1581.4 $[M+H]^+$, 1602.5 $[M+Na]^+$, 1680.5 $[M+TEA]^+$.

Src SH2 Domain Binding Assay.

The binding to the SH2 domain alone vs. binding to full length of these Src kinases for both ATP-phosphopeptide conjugates and parent structures were determined using a fluorescence polarization (FP) binding assay according to previously reported methods. $IC_{50}$ values were assigned to individual compounds according to their competitive binding affinity vs. a high-affinity peptide probe, fluorescein-Gly-pTyr-Glu-Glu-Ile-$NH_2$ (SEQ ID NO: 4). All assays were performed in triplicate. For ATP-phosphopeptide conjugate 7, the same experimental procedures were followed except that after incubation with the Src SH2 domain for 10 min, the reaction mixture containing the compound was radiated with short-wave UV (254 nm) for 1 h then with long-wave UV (365 nm) for 1 h. The inhibition percentages were calculated and the $IC_{50}$ values were obtained by using Curve-Fitting software (CurveExpert 3.1).

Steady-State Kinetic Assays.

Steady-state kinetic assays with Src or Lck were carried out using a radioactive assay to evaluate mechanisms of inhibition by ATP-phosphopeptide conjugates relative to natural substrate ATP. Artificial substrate $polyE_4Y$ (average MW: 35 kD) was used for routine kinase activity. The kinase activity of PTKs was first determined using a standard radiometric PTK activity assay. This assay contains $polyE_4Y$ as the phosphate accepting substrate, [γ-$^{32}$P]-ATP, and $MgCl_2$. After a reaction time of 30 min at 30° C., 35 μl of the reaction mixture was removed and spotted onto a filter paper and placed into warm 5% trichloroacetic acid (TCA). The TCA stops the kinase reaction, precipitates the proteins and polyE$_4$Y onto the filter paper, and washes the un-reacted ATP and others away. After 3 TCA washes for 10 min each, the radioactivity remaining on the filter paper was determined by liquid scintillation counting. The assays were done in duplicates and repeated at least three times. Control reactions lacking polyE$_4$Y were included for each enzyme concentration to correct for any non-polyE$_4$Y specific phosphorylation. Percentage of inhibition was plotted as a function of the compound concentration and the IC$_{50}$ value (the concentration of a compound that caused 50% inhibition) was obtained from such a plot. To determine the inhibitory mechanism with regard to ATP, the K$_m$ and V$_m$ values with ATP as the variable substrate was determined at various concentrations of ATP-phosphopeptide conjugates 5 and 7 while other components of the assay were at fixed concentrations using Lineweaver double reciprocal plots. The inhibitory mechanism was determined based on the effect of the compound on the K$_m$ and V$_m$ values Inhibitory constant (K$_i$) was determined by using Sigma Plot 8.0 Enzyme Kinetics Module. For mixed experiments using ATPγS mixture with pYEEI (SEQ ID NO: 3), same molar concentrations were used for each component.

Cross-Linking Experiment Using Diazido Conjugate 7.

Diazido conjugate 7 (1.2 mg) was dissolved in kinase buffer (265 mL) to make a stock solution of 3,000 μM. The reaction mixtures were prepared with the final concentrations of 7 (50 or 500 μM), MgCl$_2$ (12 mM), and Lck (80 μM). The reaction mixtures were allowed to incubate for 10 min at room temperature, placed in a dark chamber, and irradiated with long wave UV 365 nm for 1.5 h or short wave UV 254 nm for 1 h and long wave 365 nm for 1 h. Control reaction mixtures prepared in the absence of UV and/or ATP-phosphopeptide conjugate 7. All reaction mixtures were denatured by incubation at 95-100° C. for 5 min. A loading buffer containing bromophenol blue (10 mL) was added. The reaction mixtures were subjected to SDS-PAGE by loading into a gel (7%) and running for 2.5 h. The gel was stained using Coomassie Blue (G95) using a standard protocol for protein staining.

N-Heteroaromatic-Peptide Conjugates Targeting the Src Kinase Domain

We previously synthesized a potent and selective peptide-ATP bisubstrate inhibitor that binds to the ATP binding site and the substrate binding site of the insulin receptor kinase (IRK). Herein, we disclose N-heteroaromatic-peptide conjugates that ATP is replaced with N-heteroaromatics. In these compounds, the binding and orientation of the peptide moiety will not be imposed by the presence of ribo-phosphate of ATP. Depending on the positioning of the peptide moiety on the heteroaromatic ring, the functional groups of the peptide may be able to find proper orientation for novel bonding interactions within the kinase domain. Herein, 3-phenylpyrazolo[3,4-d]pyrimidines is shown as an example of the ATP binding site ligands. Other ATP mimics are N-heteroaromatics including purine-based derivatives, pyrimidine-based derivatives such as 2,4-diamino-5-substituted pyrimidine derivatives, pyrazole[3,4-d]pyrimidine derivatives, pyrrolo[2,3-d] pyrimidine derivatives, pyrido[2,3-d]pyrimidine derivatives, amino-substituted dihydropyrimido[4,5-d]pyrimidinone derivatives, thieno- and furo-substituted derivatives, quinazoline derivatives, quinoline derivatives, and several natural products such as aminogenistein. A number of these bicyclic N-heteroaromatics have been described as potent inhibitors of SFKs. Peptides were used as tools for exploring novel potential interactions within the kinase domain. This approach has a fundamental difference with bisubstrate inhibitors that target specific binding sites. N-Heteroaromatic-peptide conjugates do not have the ribo-phosphate of ATP. Therefore, the peptides have the freedom to bind to and interact with potential binding sites when they are positioned properly. Src peptide inhibitors, CIYKYY (SEQ ID NO: 2) and YIYGSFK (SEQ ID NO: 1), were selected as initial templates and examples for conjugation with N-heteroaromatics. Peptides and peptide-like compounds include all substrate binding site inhibitors such as peptidomimetics, cyclic peptides, small molecules designed to mimic peptides, and small molecules designed to bind to activation domain, ATP binding site and substrate binding site.

N$^1$- and N$^4$-Substituted Bicyclic N-Heteroaromatics.

In principle, a limiting feature in the design of N-heteroaromatic-peptide conjugates is lack of understanding of the geometric and electronic features that might contribute to binding of such compounds to Src kinases. In order to attach ATP mimics to peptides, it was necessary to determine the best position in the heterocyclic ring for attachment to selected peptides. Molecular modeling and structure-activity relationship studies suggested that for bicyclic N-heteroaromatics the attachment of the linker and peptide to the heterocyclic ring would not mimic a position similar to the ATP-linker-peptide conjugates. This is due to the absence of a ribo-phosphate linker and the presence of other substituents such as phenyl on the heterocyclic ring of 3-phenylpyrazolopyrimidine.

It has been previously reported that tethering bulky chemical groups to PP1 through its exocyclic amine (N$^4$) yields weak inhibitors, owing to the unfavorable interactions, with a structurally conserved amino acid residue 338 that contains a bulky side chain in all known eukaryotic protein kinases. Substitution at N$^4$ in 3-phenylpyrazolopyrimidine derivatives with esters or larger groups in 24 and 25 (FIG. 14) significantly reduced the inhibitory potency, therefore confirming the previous results.

Figure 14:
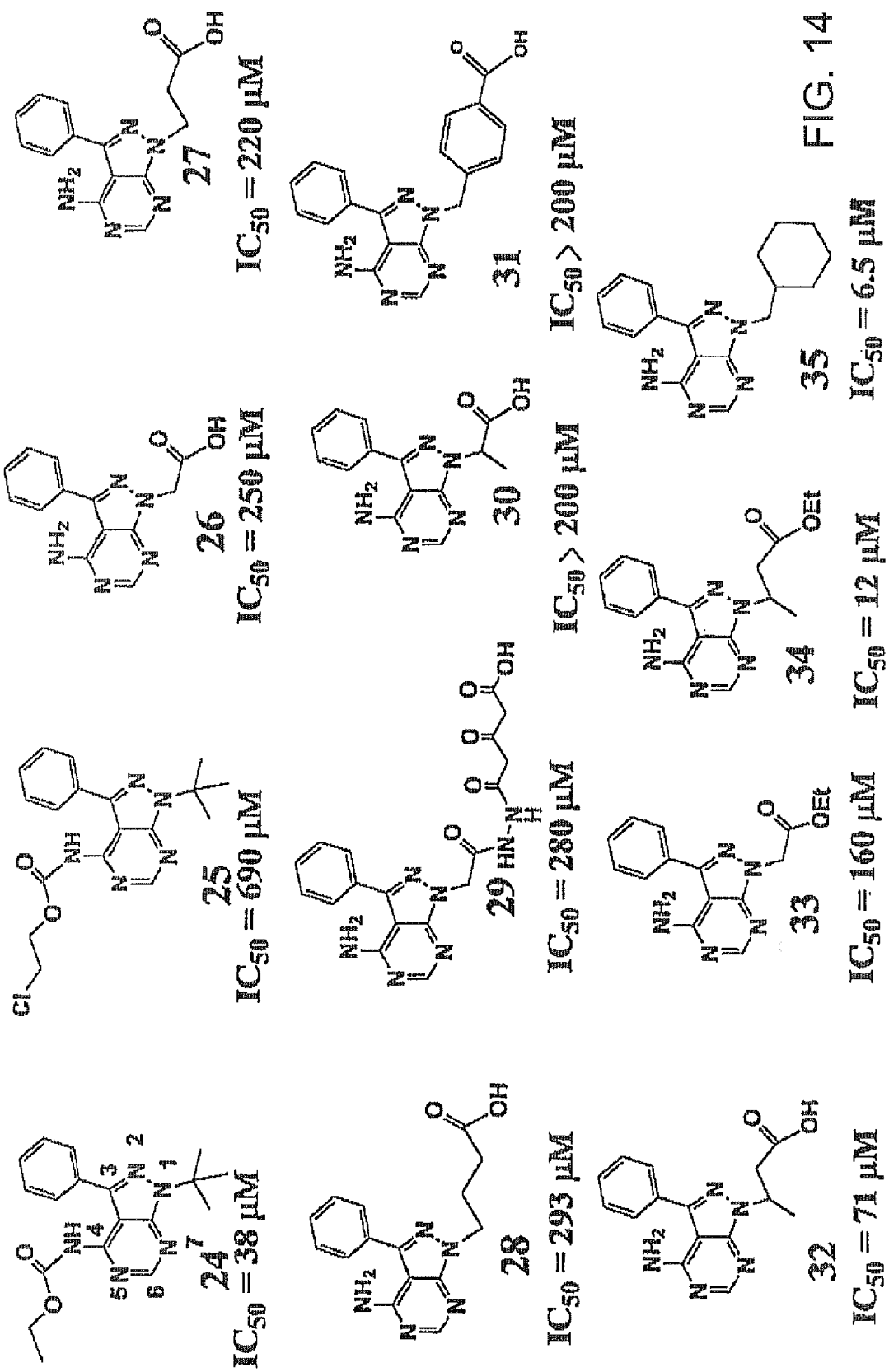
FIG. 14 shows $N^1$- and $N^4$-Substituted 3-phenylpyrazolo[3,4-d]pyrimidine derivatives.
Figure 14:
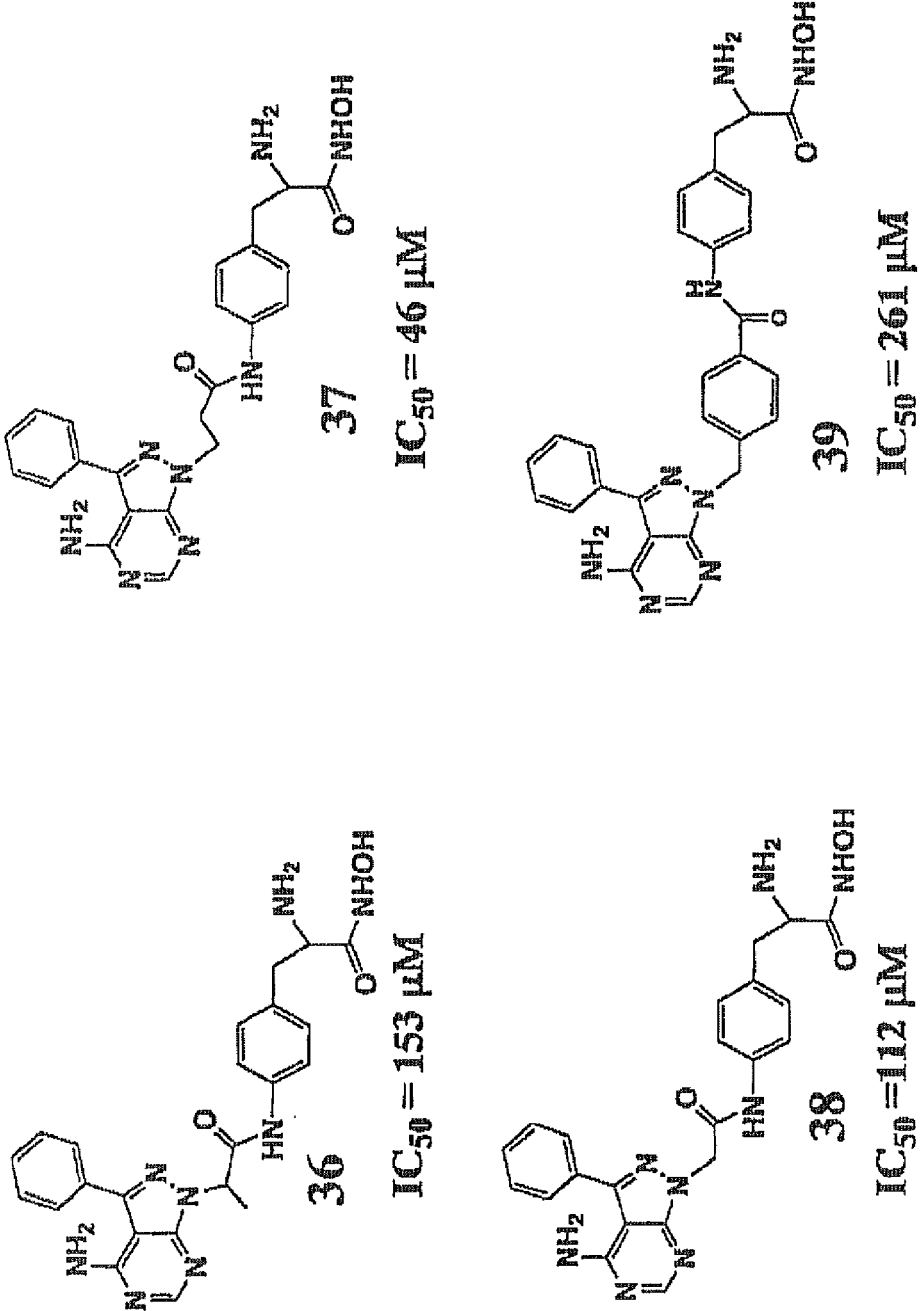

3-Phenylpyrazolopyrimidine derivative 26 (FIG. 14), substituted with an alkyl carboxylic acid at N$^1$ endocyclic amine, exhibited weak inhibitory potency (IC$_{50}$=250 μM). A similar pattern was observed by the attachment of alkyl carboxylic acids containing a longer alkyl chain, as shown in 27-31. Molecular modeling studies indicated that the carboxylic acids in compounds 26-31 have unfavorable electrostatic interaction with the side chain of Asp386. This residue is in the proximity of the cavity occupied by the ATP binding site inhibitors. When the methyl group was incorporated on the β-carbon of the side chain of alkyl carboxylic acid, a higher inhibitory potency (IC$_{50}$=71 μM) was resulted (32 versus 27); this may be due to the enhanced hydrophobic interaction by the methyl group with the hydrophobic cavity. Conversion of carboxylic acid in 26 and 32 to ethyl ester in 33 and 34, respectively, improved the inhibitory potency slightly, suggesting that the short carboxylic acids as N$_1$ substituents have unfavorable electrostatic interaction with Asp386. Attachment of the cyclohexyl group to N$_1$ position in 35 improved the inhibitory potency significantly, but the attachment of phenylalanine hydroxamates in 36-39 was not effective (FIG. 14). In the next step, we investigated whether the attachment of specific Src peptide inhibitors to the N$^1$ endocyclic amine, through a short linker, can improve the inhibitory potency.

N$^1$-Attachment of 3-Phenylpyrazolopyrimidine to N-Terminal of Peptides Through Short Linkers.

Two peptides (FIG. 15), Ac-CIYKYY (SEQ ID NO: 2) (40) and Ac-YIYGSFK (SEQ ID NO: 1) (41), were selected for the conjugation with the 3-phenylpyrazolopyrimidine. Peptides 40 and 41 have been reported to be substrate binding side inhibitors of Src. A radioactive kinase assay using polyE4Y as the substrate showed that Ac-CIYKYY (SEQ ID NO: 2) (40, $IC_{50}$=400 μM) and Ac-YIYGSFK (SEQ ID NO: 1) (41, $IC_{50}$=570 μM) were weak inhibitors of polyE4Y phosphorylation. In this invention, CIYKYY (SEQ ID NO: 2) and YIYGSFK (SEQ ID NO: 1) were used as the initial templates for conjugation with N-heteroaromatics to generate synergistic inhibition effect for the second class of compounds. Any heteroaromatic-peptide conjugates synthesized in this way from attachment of any other peptides, peptidomimetic, cyclic peptides to N-heteroaromatics is claimed in this invention.

Since both 3-phenylpyrazolopyrimidine derivative 26 and peptides 40 and 41 exhibited weak inhibitory potency, we investigated whether the conjugation of these compounds can generate some synergistic inhibition effect.

Two 3-phenylpyrazolopyrimidine-peptide conjugates were synthesized (FIG. 15) using 3-phenylpyrazolopyrimidine as the ATP mimic and CIYKYY (SEQ ID NO: 2) (40) and YIYGSFK (SEQ ID NO: 1) (41) as peptide substrates. Conjugates were designed to mimic the phosphate donor (ATP) and the acceptor components (Tyr-containing peptides). Both 3-phenylpyrazolopyrimidine-peptide conjugates 42 ($IC_{50}$=0.38 μM) and 43 ($IC_{50}$=2.7 μM) inhibited the polyE4Y phosphorylation by active Src significantly higher than compound 26 ($IC_{50}$=250 μM) and peptides, Ac-$C_1I_2Y_3K_4Y_5Y_6$ (SEQ ID NO: 2) (40, $IC_{50}$=400 μM) and Ac-YIYGSFK (SEQ ID NO: 1) (41, $IC_{50}$=570 μM), respectively; this suggests a synergistic inhibition effect of the conjugation of the ATP mimic with the peptide by possibly creating favorable interactions between the conjugate and the kinase domain.

Deletions of Amino Acids.

The presence of the specific amino acids seems to be critical for generating the inhibitory potency. The removal of amino acids in the peptide chains of CIYKYY (SEQ ID NO: 2) in 3-phenylpyrazolopyrimidine-peptide conjugate (FIG. 16a) reduced the inhibitory potency. For example, compound 44 lacked IYKYY (SEQ ID NO: 11) and exhibited a reduced inhibitory potency by approximately 2000-fold when compared to 42. The 3-phenylpyrazolopyrimidine-peptide conjugate 45 that did not have KYY reduced the inhibitory activity by approximately 145-fold when compared to 42. By the removal of KYY in C-terminal, the peptide does not have any other potential interactions with the exterior region of the ATP binding site. Approximately half of the inhibition activity was lost in 46 when C-terminal tyrosine was removed in the conjugate 42. The results indicate that all amino acids are required in generating the maximum inhibitory activity. Molecular modeling studies suggested that in all of these analogs, 42 (FIG. 15) and 44-46 (FIG. 16a), the peptide is located in the opposite direction of the phenyl group of pyrazolopyrimidine and does not bind to the substrate binding site.

Deletion of the Phenyl Group.

The compound 47 that lacks 3-phenyl moiety exhibited no inhibitory potency (FIG. 16b) compared to the corresponding compound containing the phenyl moiety (42, $IC_{50}$=0.38 μM). These results suggest that the hydrophobic interaction of the phenyl group with hydrophobic pocket is essential for the binding of 3-phenylpyrazolopyrimidines to the ATP binding site. By removing the phenyl group, the peptide moiety loses the right orientation for binding to the kinase domain.

The Attachment of 3-Phenylpyrazolopyrimidines to the Side Chains of Different Amino Acids in the Peptide Sequence.

Figure 17:
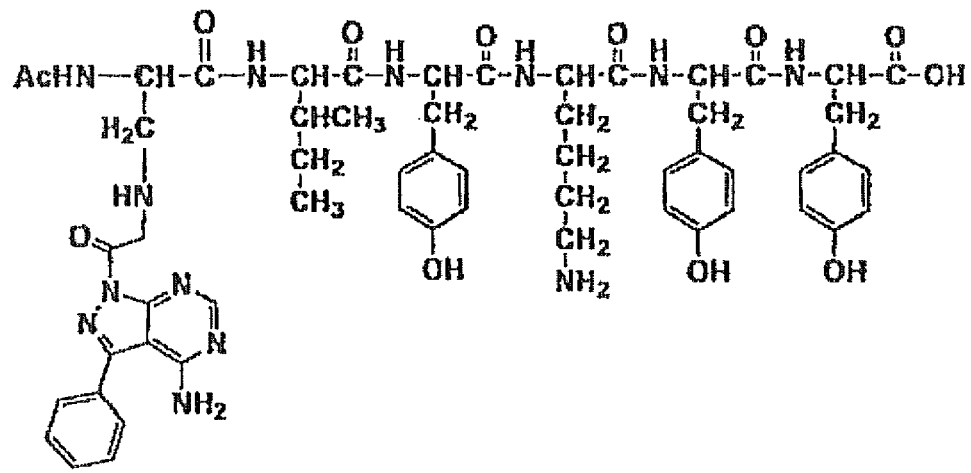
FIG. 17 shows the attachment of 3-phenylpyrazolopyrimidines to the side chains of different amino acids.
Figure 17:
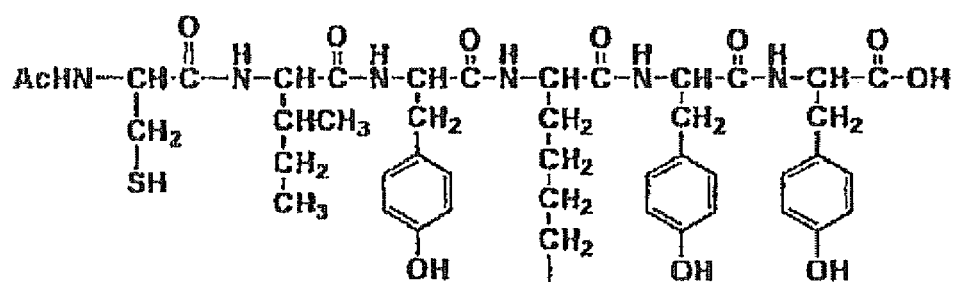
Figure 17:
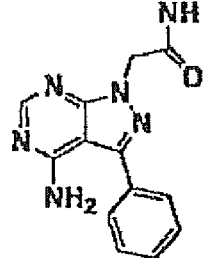
Figure 17:
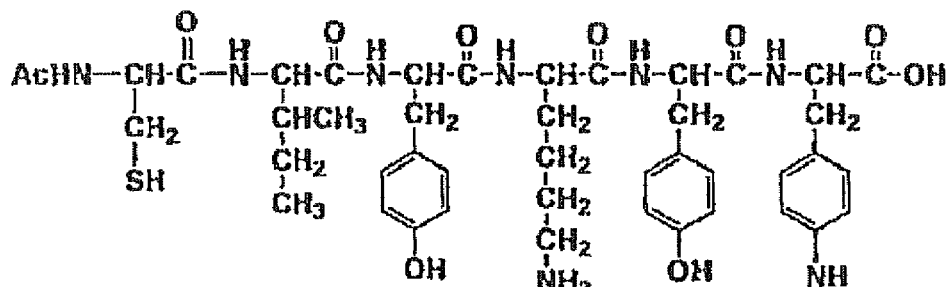
Figure 17:
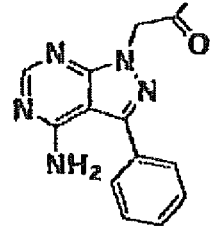
Figure 17:
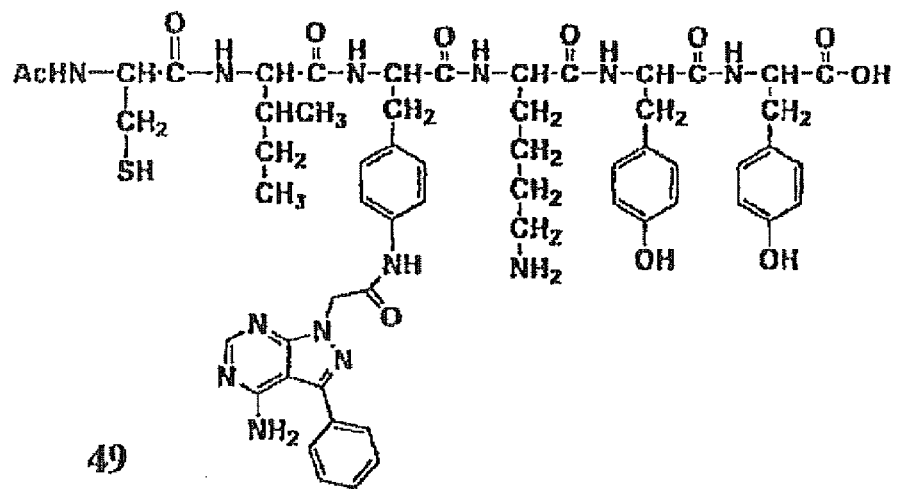
Figure 17:
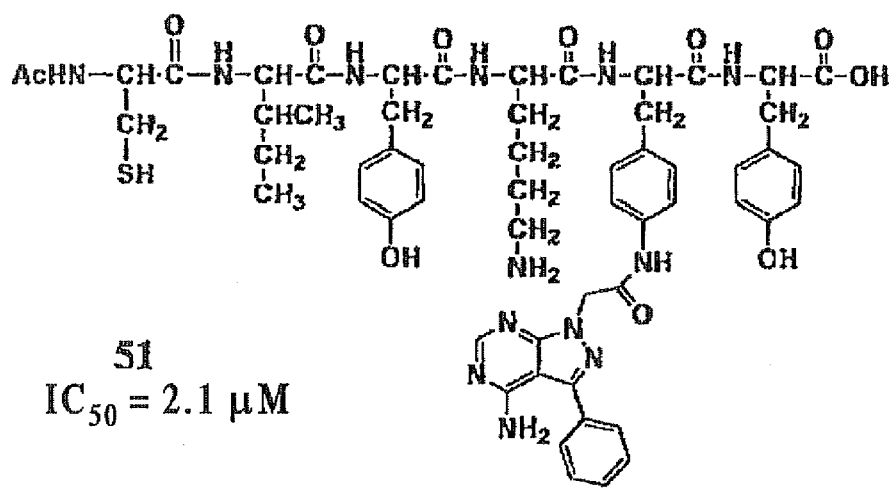
Figure 17:
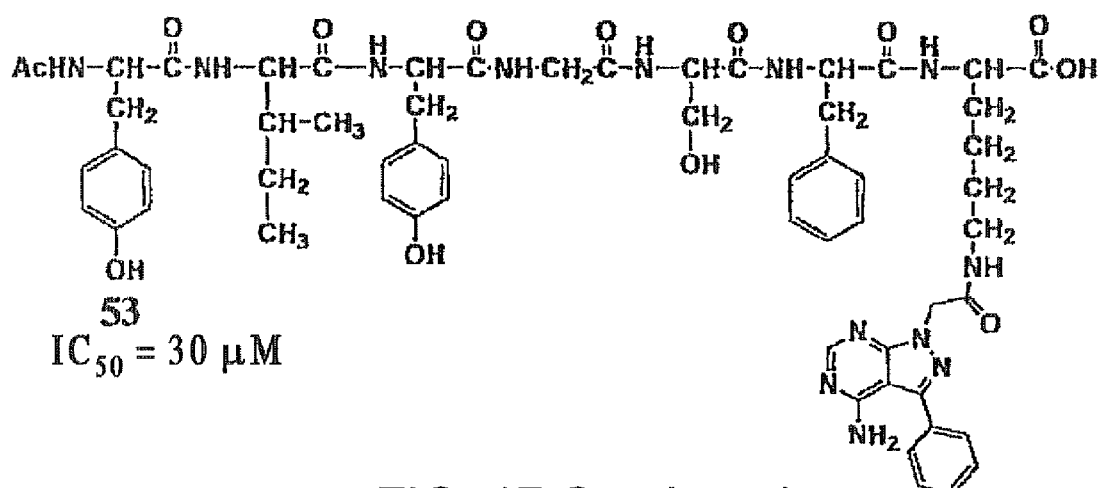

The position of the 3-phenylpyrazolopyrimidine ring relative to the peptide substrate, $C_1I_2Y_3K_4Y_5Y_6$ (SEQ ID NO: 2), proved to be critical for generating maximal inhibitory potency. When the 3-phenylpyrazolopyrimidine ring was moved along the peptide (FIG. 17) and was attached to the side chains of different amino acids, the inhibition potency was reduced. Aminophenylalanine and β-aminoalanine were used for conjugation purposes in place of tyrosine and cysteine, respectively.

Attachment to side chains of $C_1$, $K_4$, and $Y_6$ diminished the inhibitory potency significantly when compared to 42. The reduction of inhibition was significant in 48 ($IC_{50}$=64 μM), in which the 3-phenylpyrazolopyrimidine was attached to the side chain of the first amino acid and where the $SH_2$ group of cysteine was substituted with the amino group. These results suggest that the free side chain of Cys residue is crucial for the inhibition. Molecular modeling studies suggested that the orientation of the peptide was changed with the attachment of the heterocyclic ring at this position and lost some of the bonding interactions with the kinase domain observed in 42. Similarly, the attachment of the N-heteroaromatic to the side chain of lysine ($K_4$) (50), and C-terminal amino acid tyrosine ($Y_6$) (52) reduced the inhibition by the analogs significantly. Attachment of the 3-phenylpyrazolopyrimidine to the side chains of the other tyrosines ($Y_3$) (49) and $Y_5$ (51) reduced the catalytic activity inhibition much less compared to other peptide conjugates 48, 50, and 52. There was a significant difference in the inhibitory potency in compounds 49 and 50, indicating the importance of the free amino group of the side chain of lysine for inhibition. Therefore, the placement of the 3-phenylpyrazolopyrimidine ring at the N-terminal of the peptide as seen in 42 appears to be optimal for generating maximal inhibitory potency.

Figure 15:
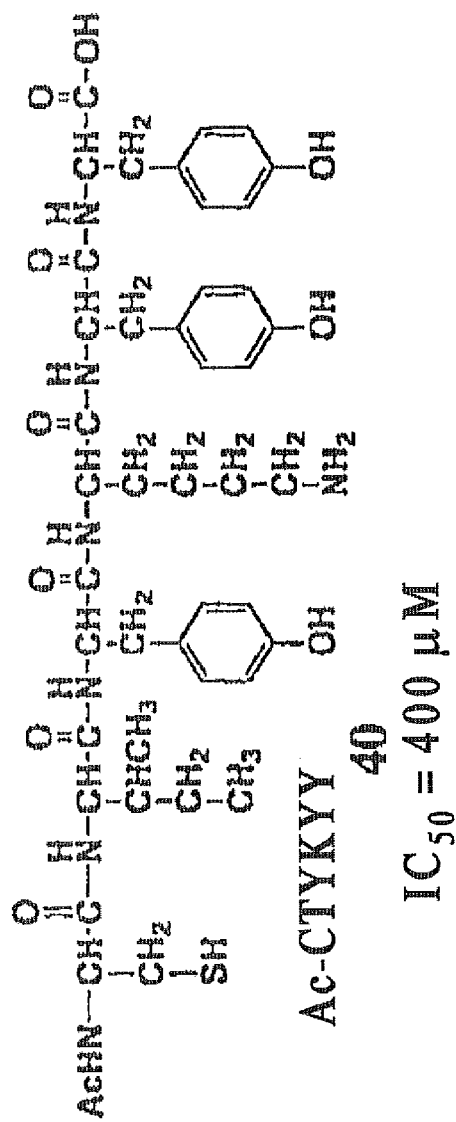
FIG. 15 shows comparison of inhibitory potency of peptides and the corresponding 3-phenylpyrazolopyrimidine-peptide conjugates suggest the synergistic inhibition effect (CIYKYY and YIYGSFK disclosed as SEQ ID NOS 2 and 1 respectively)
Figure 15:
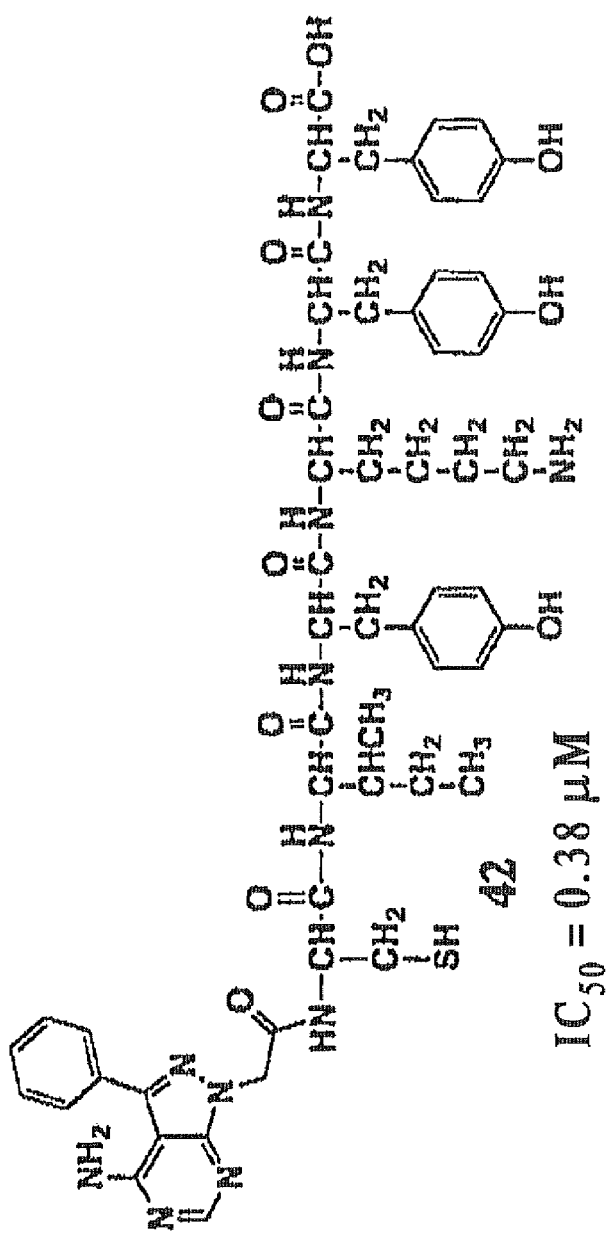
Figure 15:
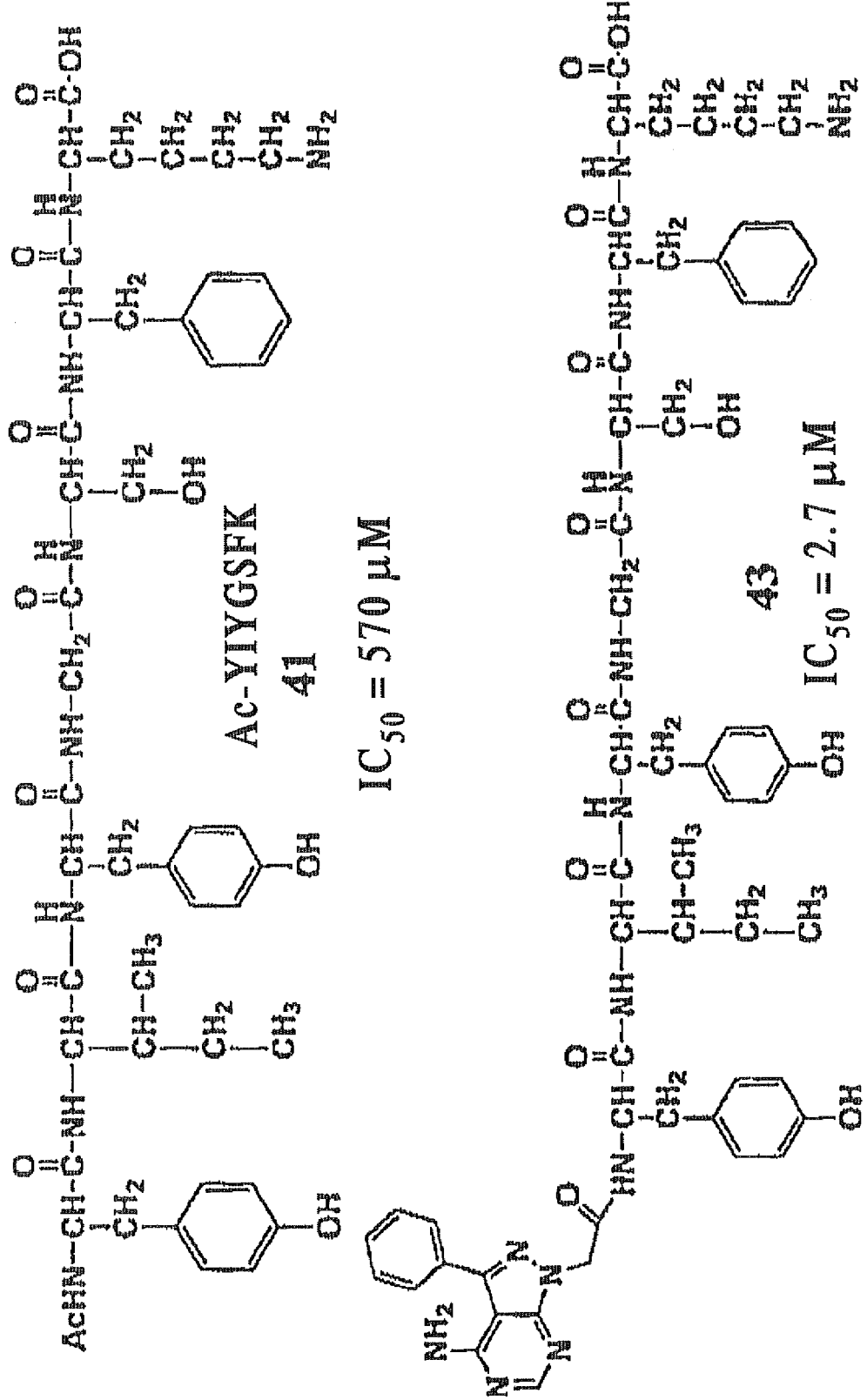
Figure 16:
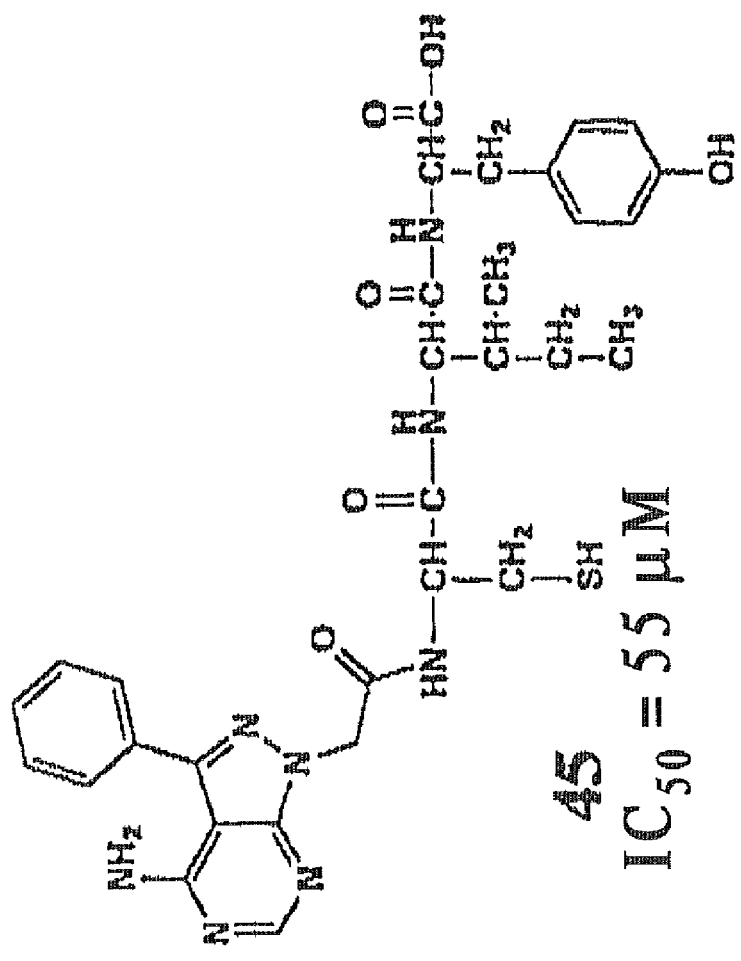
FIG. 16 shows (a) effects of deleting one or more amino acids in 3-phenylpyrazolopyrimidine-peptide conjugate 42 and (b) deleting the phenyl group in 42 to yield pyrazolopyrimidine-peptide conjugate 19.
Figure 16:
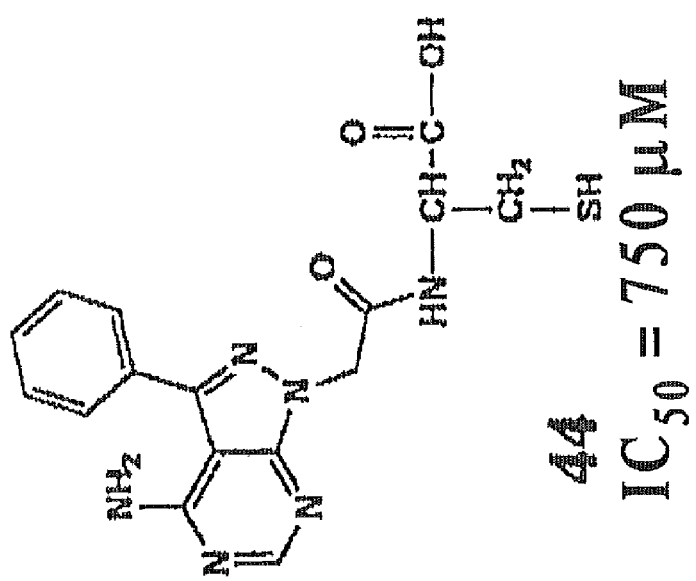
Figure 16:
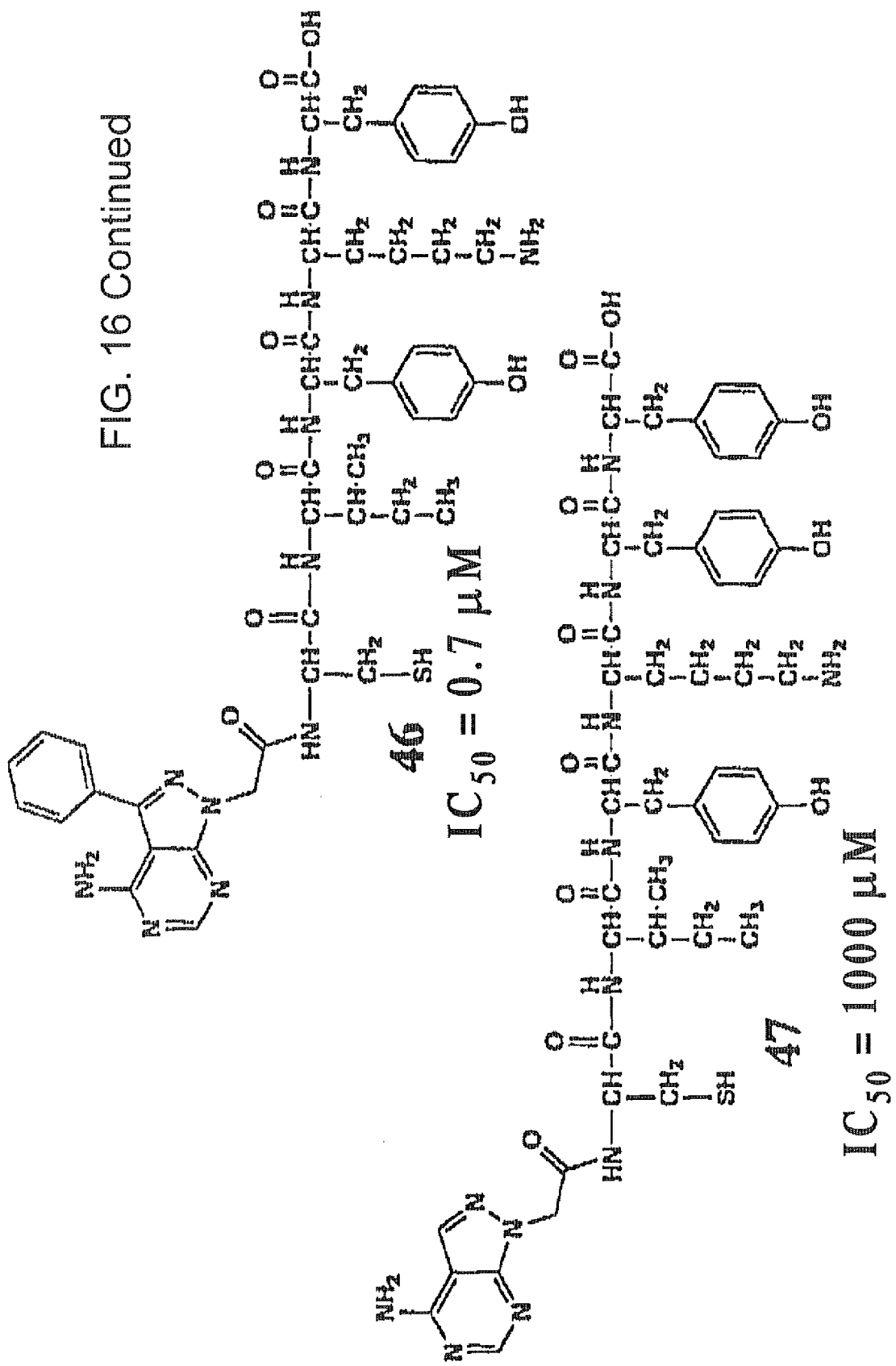

Similarly, in compound 53, in which the 3-phenylpyrazolopyrimidine is attached to the side chain of C-terminal lysine in YIYGSFK (SEQ ID NO: 1) (FIG. 17), the inhibitory potency was reduced by 11-fold when compared to the corresponding N-terminal analog 43 ($IC_{50}$=2.7 μM, FIG. 15). This invention include several other compounds in which the heterocyclic ring (pyrrolopyrimidine, pyrazolopyrimidine, or pyrimidopyrimidine and other ATP mimics listed above) is attached to the side chain of different amino acids in more potent peptide templates.

The Nature and Size of the Linker.

Figure 18:
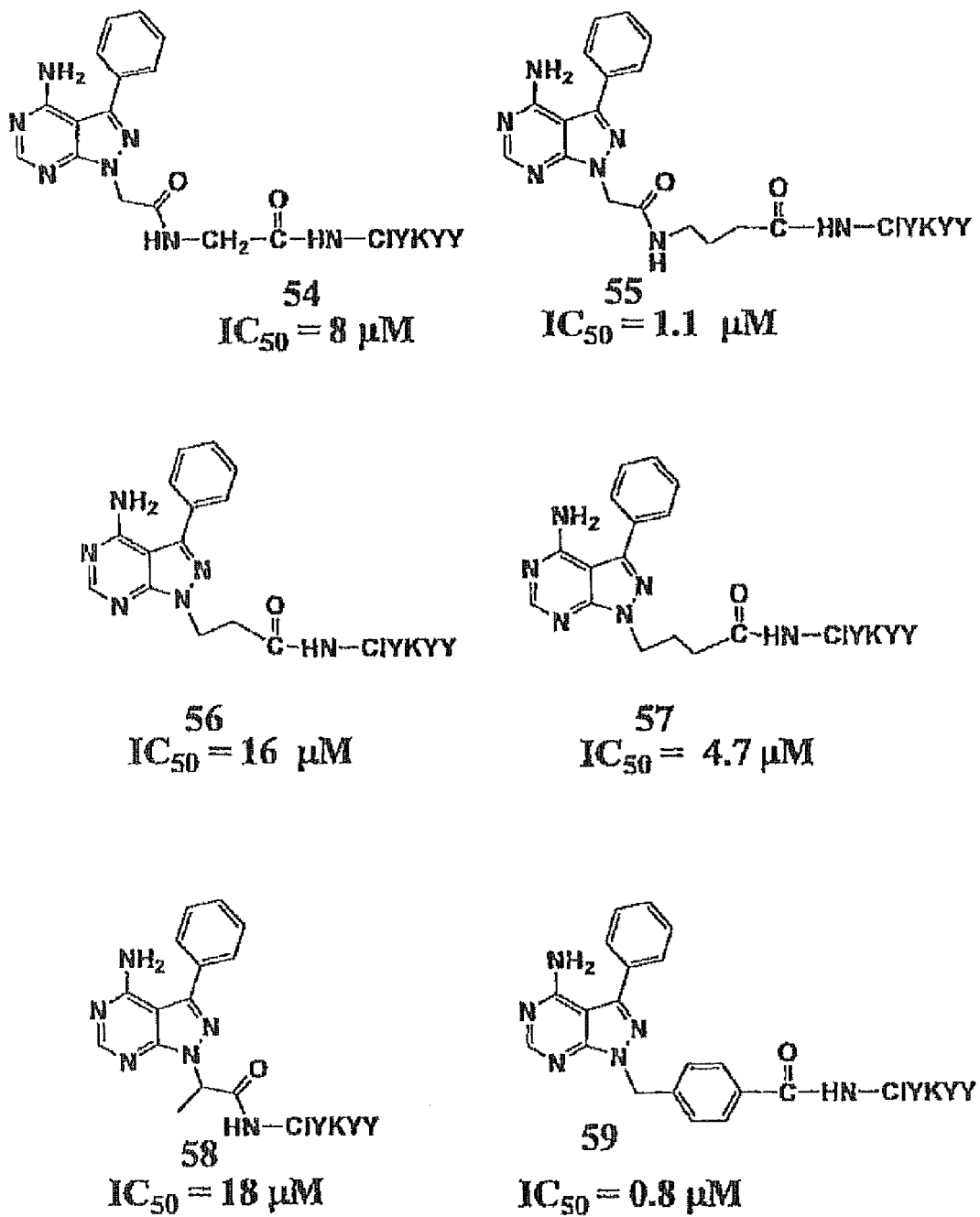
FIG. 18 shows 3-phenylpyrazolopyrimidine-peptide conjugates having different linkers (CIYKYY disclosed as SEQ ID NO: 2)

The nature and the length of the linker appeared to be important in the inhibitory activity. To determine the importance of the linker distance, several new compounds were prepared that had longer linkers between the peptide and the 3-phenylpyrazolopyrimidine (FIG. 18). The incorporation of glycine between the N-heteroaromatic and cysteine residue in 54 reduced the inhibitory potency by 21-fold when compared to 42 ($IC_{50}$=0.38 μM). Increasing the length of the linker by using γ-aminobutyric acid in 55 rescued some of the inhibitory potency. A similar pattern was observed when comparing 56 and 57. Compound 57 with additional methylene group in the linker had approximately 3.5 fold more inhibitory potency than 56. Consequently, the nature and length of the linker appear to directly effect the orientation of the peptide and inhibitory potency. The incorporation of methyl groups in the linker diminished the inhibitor potency as seen in 58 (FIG. 18) compared to the corresponding compound 42 ($IC_{50}$=0.38 μM) without the methyl group. However, the conjugate 58 was more potent compared to the parent N-heteroaromatic 30 ($IC_{50}$>200 μM, FIG. 14) containing the linker with carboxylic acid. The incorporation of a phenyl group between the N-heteroaromatic and cysteine residue in 59 significantly improved the inhibitory potency ($IC_{50}$=0.8 μM). Overall, these studies underscore the importance of linker length for achieving a high affinity interaction. Since these 3-phenylpyrazolopyrimidines lack the ribo-phosphate groups of ATP, the N-heteroaromatic group is closer to the peptide. Therefore, it is necessary to incorporate an appropriate linker to achieve the maximal inhibition. This disclosure include other linkers such as those in FIG. 12 used for the conjugation. This disclosure also include other N-heteroaromatic derivatives such as 32, 35 (FIG. 14), pyrrolopyrimidine, pyrazolopyrimidine, or pyrimidopyrimidine, other ATP mimics listed above. This disclosure also includes other peptides (listed in Table 1 and others), peptidomimetics, small molecules and cyclic peptides for binding to N-heteroaromatics for this purpose of inhibiting Src kinases.

The Nature of the Peptide.

The nature of the peptide plays an important role in generating inhibitory activity. Table 1 shows a list of some of the peptides disclosed as Src kinases inhibitors alone or in conjugation with heteroaromatic rings. It was investigated whether functional group modifications in peptide side chains can improve the inhibitory activity of weak inhibitor peptide Ac-CIYKYY (SEQ ID NO: 2), 40 ($IC_{50}$=400 μM). Peptide Ac-CIYKF($NO_2$)Y (SEQ ID NO: 12) (62), in which the nitrophenylalanine is located at $Y_5$ position, demonstrated a significantly higher inhibitory potency by approximately 750-fold versus 40 (Table 1). The peptide Ac-CIYKF($NH_2$)Y (SEQ ID NO: 13) (63), in which the aminophenylalanine is in a similar position to nitrophenylalanine in 62, exhibited a significantly reduced inhibitory potency ($IC_{50}$=93 μM). All of the inhibitory potency disappeared when the nitrophenylalanine in peptide Ac-CIYKF($NO_2$)Y (SEQ ID NO: 12) (62) was replaced with the phenylalanine in peptide Ac-CIYKFY (SEQ ID NO: 14) (61) ($IC_{50}$>700 μM), indicating the importance of the nitro functional group for inhibition.

The incorporation of nitrophenylalanine at position 3 or 6 in peptides Ac-CIF($NO_2$)KYY (SEQ ID NO: 15) (64) ($IC_{50}$=1.5 μM) or Ac-CIYKYF($NO_2$) (SEQ ID NO: 16) (66) ($IC_{50}$=10.8 μM), respectively, showed lower inhibitory potency when compared to peptide CIYKF($NO_2$)Y (SEQ ID NO: 12) (62), suggesting that the incorporation of nitrophenylalanine at the $Y_5$ position is the optimal for generating the maximal inhibitory potency. Peptides 67 (Ac-CIF($NH_2$)KYY) (SEQ ID NO: 17) and 68 (Ac-CIYKYF($NH_2$) (SEQ ID NO: 18)), in which the aminophenylalanine is incorporated at the $Y_3$ and $Y_6$ positions, respectively, were not active when compared to the corresponding nitropeptides 64 and 66, suggesting the importance of the nitro group for producing the inhibitory potency (Table 1).

Dinitropeptides, Ac-CIF($NO_2$)KF($NO_2$)Y (SEQ ID NO: 19) (69) and Ac-CIYKF($NO_2$)F($NO_2$) (SEQ ID NO: 20) (70), in which the nitrophenylalanine was incorporated at position 5, partially improved the inhibition compared to the corresponding mononitropeptides, 64 and 66, respectively; this may be due to the importance of the synergistic inhibition effect of the nitrophenylalanine at position 5. Similarly, the dinitropeptide Ac-CIF($NO_2$)KYF($NO_2$) (SEQ ID NO: 21) (71) exhibited the inhibitory potency between mononitropeptides Ac-CIF($NO_2$)KYY (SEQ ID NO: 15) (64) and Ac-CIYKYF($NO_2$) (SEQ ID NO: 16) (66) (Table 1).

The effect of substitution on the phenyl group at Y5 position of CIYKYY (SEQ ID NO: 2) with other substituents, such as phosphate, guanidine, or halogens, was investigated. The presence of negatively- or positively-charged groups, such as phosphate and guanidine, at para position of the phenyl eliminated the inhibitory potency, as shown in 72 and 73. On the other hand, compounds with substituted halogens (74-76) exhibited inhibitory potency in the order of I>Cl>F, suggesting the importance of the hydrophobic interaction. Molecular modeling studies showed that the intramolecular hydrogen bonding of the amino group of the K4 with hydroxyl group of Y5 in 40 is eliminated when the hydroxyl group is substituted with nitro group or halogens in 62 and 74-76, respectively. Other substituents such as phosphate, guanidine, and sulfonamide, showed intramolecular hydrogen bonding with the amino side chain group of the lysine. It appears that the free amino group of the lysine has a critical interaction with the binding pocket in the kinase domain. This interaction is interrupted by the presence of the intramolecular hydrogen bonding between the amino group of K4 and substituents of the phenyl group at the Y5 position (Table 1).

TABLE 1

Inhibitory potency values for modified peptide analogs for some of the modified peptide analogs synthesized as Src kinase inhibitors and as the peptide moiety for the attachment to the heteroaromatic ring.

| Number | Compound | Mass Calculated | Mass Found | $IC_{50}$ (μM) |
| --- | --- | --- | --- | --- |
| 40 | Ac-CIYKYY (SEQ ID NO: 2) | 893.40 | 894.4066 | 400 |
| 60 | CIYKYY (SEQ ID NO: 2) | 851.39 | 852.3309 | >200 |
| 61 | Ac-CIYKFY (SEQ ID NO: 14) | 877.40 | 877.7894 | >700 |
| 62 | Ac-CIYKF($NO_2$)Y (SEQ ID NO: 12) | 922.39 | 922.8111 | 0.53 |
| 63 | Ac-CIYKF($NH_2$)Y (SEQ ID NO: 13) | 892.42 | 893.4963 | 93 |
| 64 | Ac-CIF($NO_2$)KYY (SEQ ID NO: 15) | 922.39 | 922.7900 | 1.5 |
| 65 | Ac-CIYKF($NO_2$)YF (SEQ ID NO: 22) | 1069.46 | 1069.6403 | 1.0 |
| 66 | Ac-CIYKYF($NO_2$) (SEQ ID NO: 16) | 922.39 | 922.8101 | 10.8 |
| 67 | Ac-CIF($NH_2$)KYY (SEQ ID NO: 17) | 892.42 | 893.1398 | 760 |
| 68 | Ac-CIYKYF($NH_2$) (SEQ ID NO: 18) | 892.42 | 893.4476 | >700 |
| 69 | Ac-CIF($NO_2$)KF($NO_2$)Y (SEQ ID NO: 19) | 951.38 | 951.7400 | 1.4 |
| 70 | Ac-CIYKF($NO_2$)F($NO_2$) (SEQ ID NO: 20) | 951.38 | 951.7349 | 5.6 |
| 71 | Ac-CIF($NO_2$)KYF($NO_2$) (SEQ ID NO: 21) | 951.38 | 951.7395 | 3.4 |
| 72 | Ac-CIYKpYY (SEQ ID NO: 23) | 973.37 | 973.6418 | >700 |
| 73 | Ac-CIYKF(4-Guanidine)Y (SEQ ID NO: 24) | 934.10 | 934.6483 | >700 |
| 74 | Ac-CIYKF(4-F)Y (SEQ ID NO: 25) | 895.39 | 895.7585 | 26 |
| 75 | Ac-CIYKF(4-Cl)Y (SEQ ID NO: 26) | 911.37 | 911.6703 | 7.3 |
| 76 | Ac-CIYKF(4-I)Y (SEQ ID NO: 27) | 1003.30 | 1003.4640 | 0.78 |
| 77 | CIYKF($NO_2$)Y (SEQ ID NO: 12) | 880.38 | 880.4645 | 3 |
| 78 | Ac-CIYKF(CN)Y (SEQ ID NO: 28) | 902.40 | 902.3045 | 6 |
| 79 | Ac-CIYKF($N_3$)Y (SEQ ID NO: 29) | 918.41 | 918.4251 | 2 |
| 80 | Ac-CIYKF(4-$NHSO_2CH_3$)Y (SEQ ID NO: 30) | 970.39 | 970.6248 | >100 |
| 81 | IYKYY (SEQ ID NO: 11) | 748.38 | 749.0283 | 211 |

TABLE 1-continued

Inhibitory potency values for modified peptide analogs for some of the modified peptide analogs synthesized as Src kinase inhibitors and as the peptide moiety for the attachment to the heteroaromatic ring.

| Number | Compound | Mass Calculated | Found | IC$_{50}$ (μM) |
|---|---|---|---|---|
| 82 | Ac-CIYKY (SEQ ID NO: 31) | 730.34 | 730.8860 | >100 |
| 83 | Ac-CYKF(4-Cl)Y (SEQ ID NO: 32) | 798.28 | 798.6547 | 39 |
| 84 | Ac-CYKpYY (SEQ ID NO: 33) | 860.28 | 860.7594 | >100 |
| 85 | YIYGSFK (SEQ ID NO: 1) | 876.44 | 877.2145 | >100 |
| 86 | YIF(NO$_2$)GSFK (SEQ ID NO: 34) | 905.43 | 905.7598 | >100 |
| 87 | Ac-YIF(NO$_2$)GSFK (SEQ ID NO: 34) | 947.44 | 947.7075 | >100 |

In general, the presence of the nitrophenylalanine or iodophenylalanine at Y$_5$ position appears to be optimal for generating the maximal inhibitory potency. Taken together, these results suggest that exploring further sequence diversity of functional groups of peptide side chains may lead to more potent peptide inhibitors. Peptide 62 and 76 and several other peptide derivatives are disclosed for attachment with bicyclic N-heteroaromatic ATP-mimics including purine-based derivatives, pyrimidine-based derivatives such as 2,4-diamino-5-substituted pyrimidine derivatives, pyrazole[3,4-d]pyrimidine derivatives, pyrrolo[2,3-d]pyrimidine derivatives, pyrido[2,3-d]pyrimidine derivatives, amino-substituted dihydropyrimido[4,5-d]pyrimidinone derivatives, thieno- and furo-substituted derivatives, quinazoline derivatives, quinoline derivatives, and several natural products such as aminogenistein.

Figure 19:
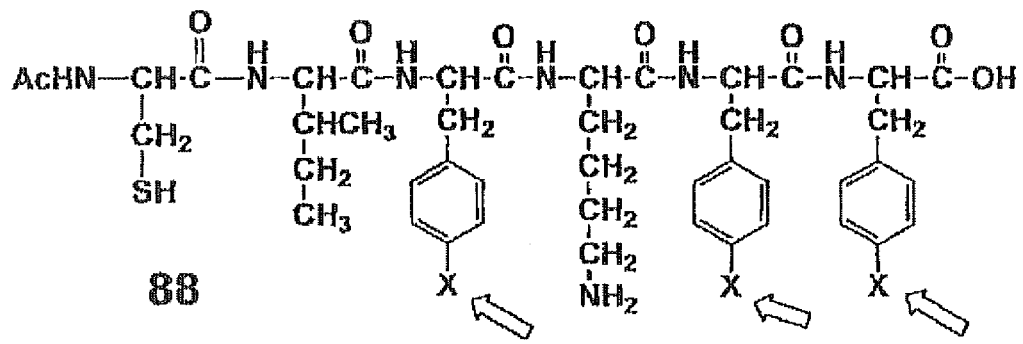
FIG. 19 shows changing the nature of peptide by substitution on one or more phenyl groups.
Figure 20:
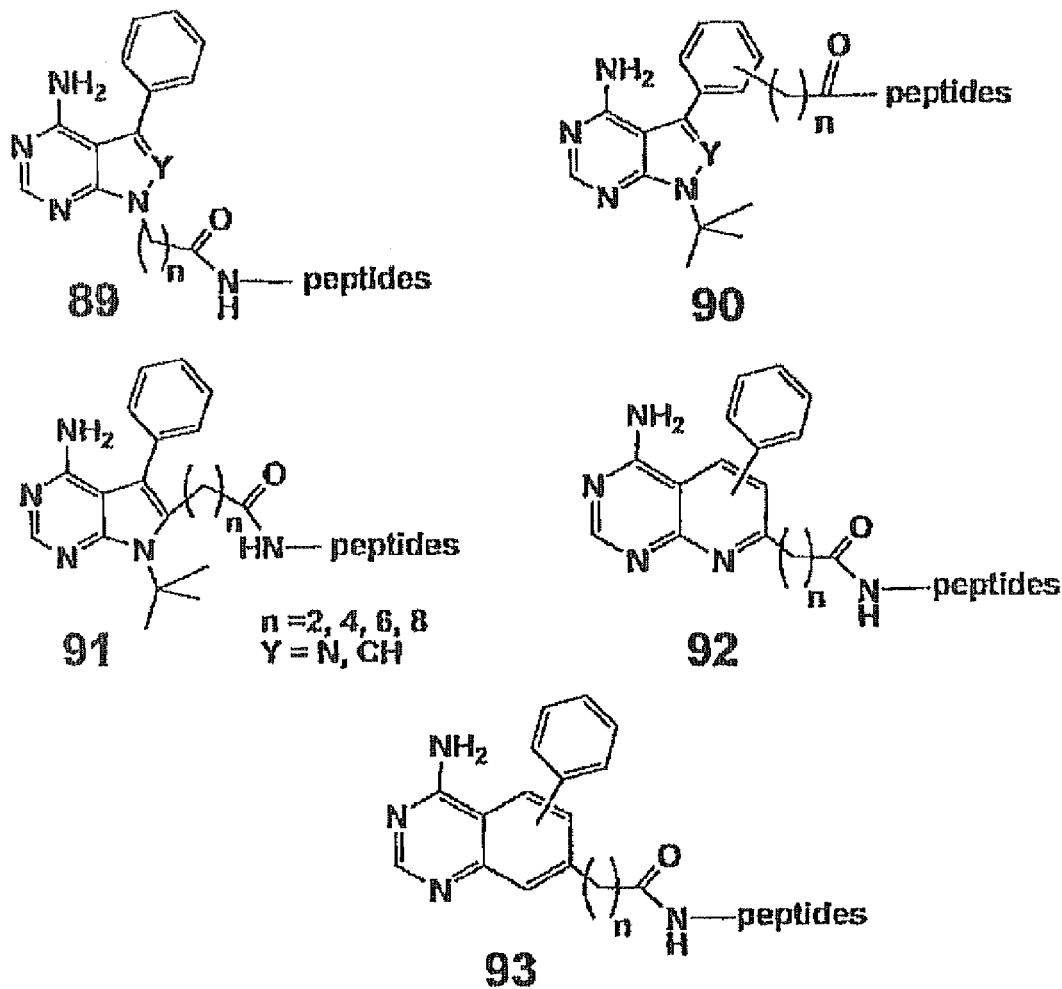
FIG. 20 shows conjugation of lead peptides with bicyclic N-heteroaromatics.

Peptides Ac-CIYKF(NO$_2$)Y (SEQ ID NO: 12) (62) and Ac-CIKYF(I)Y (SEQ ID NO: 35) (76) (Table 1) containing a nitrophenylalanine and iodophenylalanine at Y$_5$ position, respectively, exhibited high inhibitory potency. Several other peptides (FIG. 19), such as peptides substituted with azide, thiocyanate, halogens or carbamate (88), at different positions in the peptide sequence are disclosed here. This is also a disclosure for the peptides conjugated with all the heteroaromatics listed above as ATP mimics, such as pyrazolopyrimidine, pyrrolopyrimidine, pyridopyrimidines, or phenylpyrimidine rings to yield for example conjugates such as 89-93 (FIG. 20). The peptides are attached to different atoms in the N-heteroaromatics.

Conformationally Constrained Peptide Analogs as Inhibitors of the Src SH2 Domain.

Figure 21:
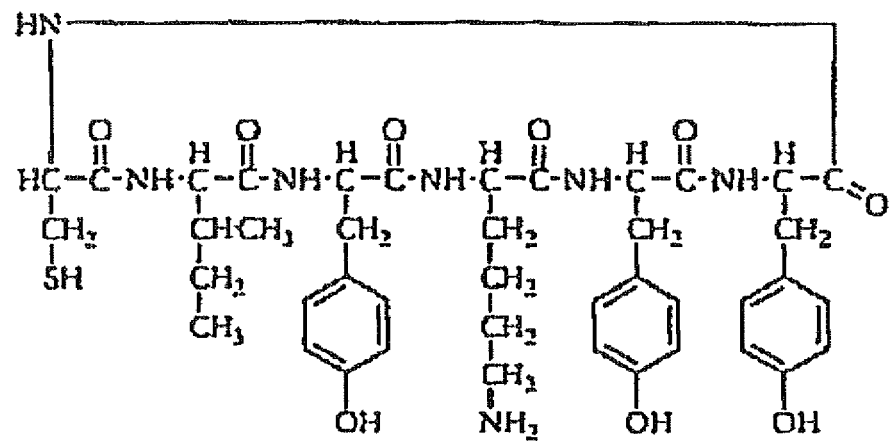
FIG. 21 shows peptides and N-heteroaromatic-peptide conjugates containing conformationally constrained peptides (n=2, 4, 6; X=Ac- or N-heteroaromatics listed above)
Figure 21:
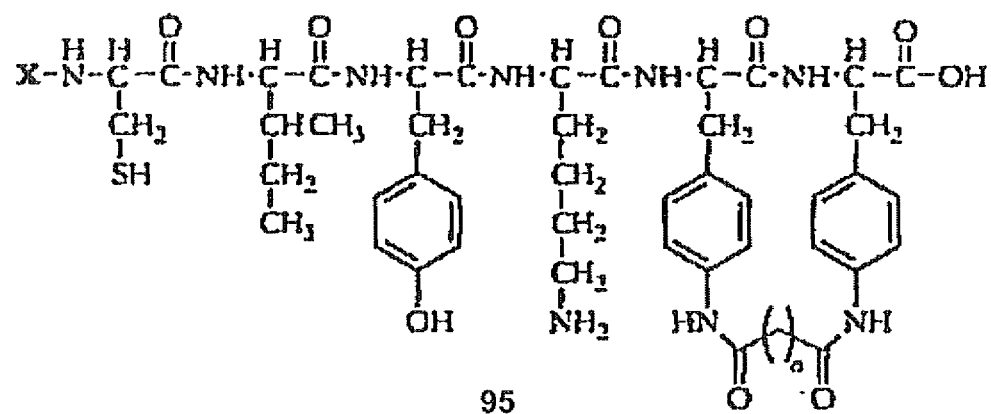
Figure 21:
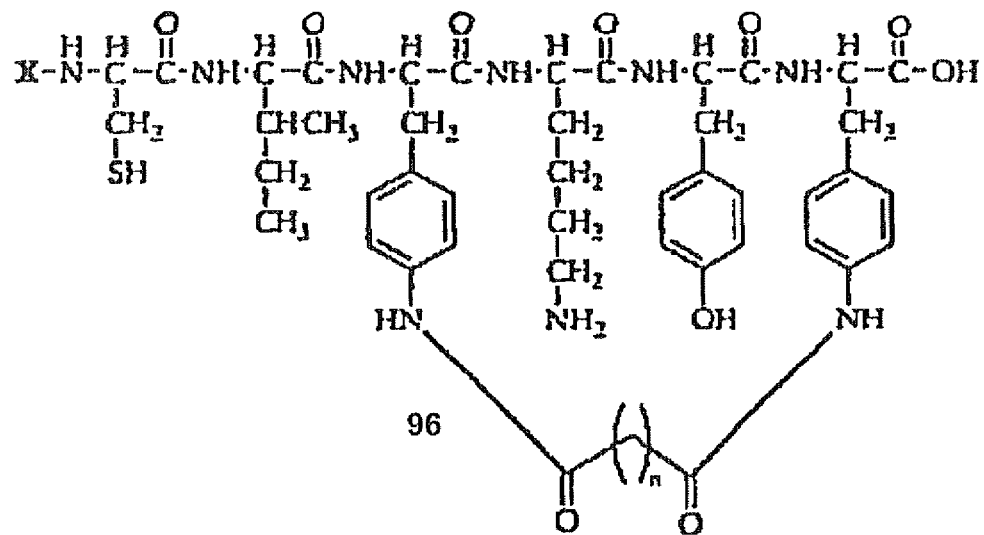
Figure 21:
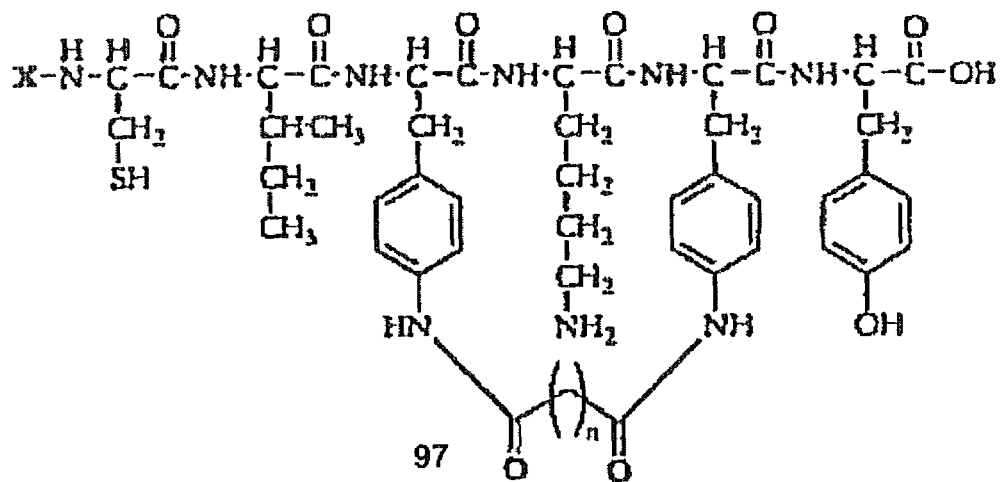
Figure 21:
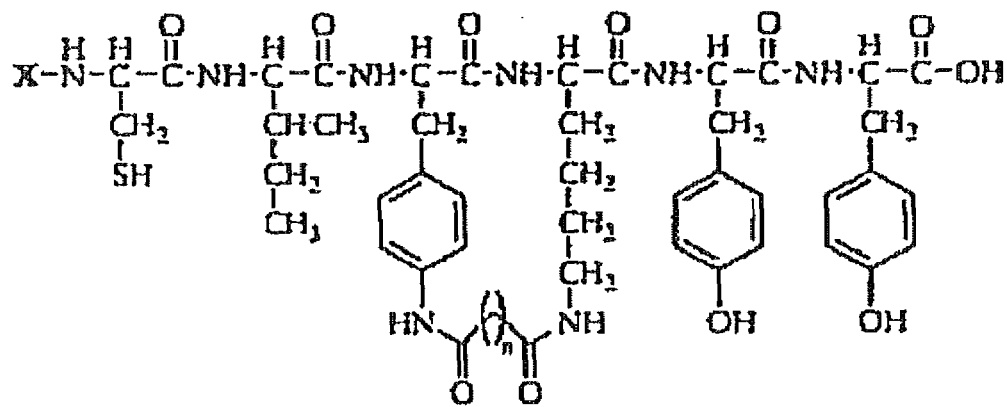
Figure 21:
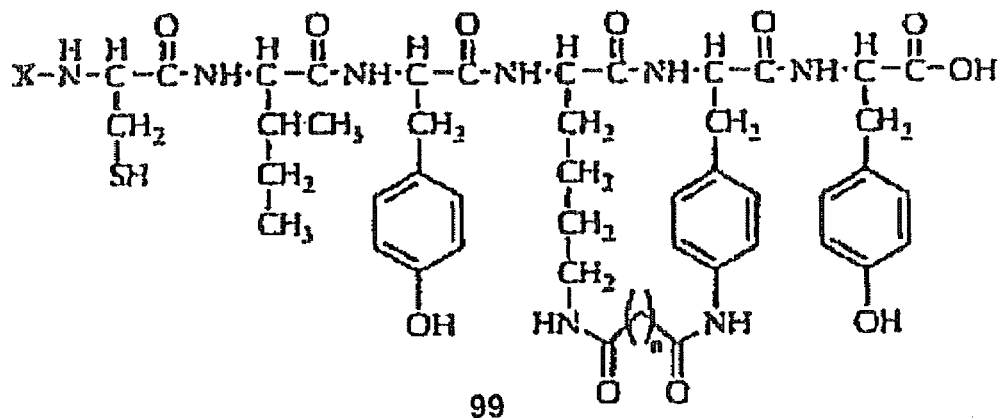
Figure 21:
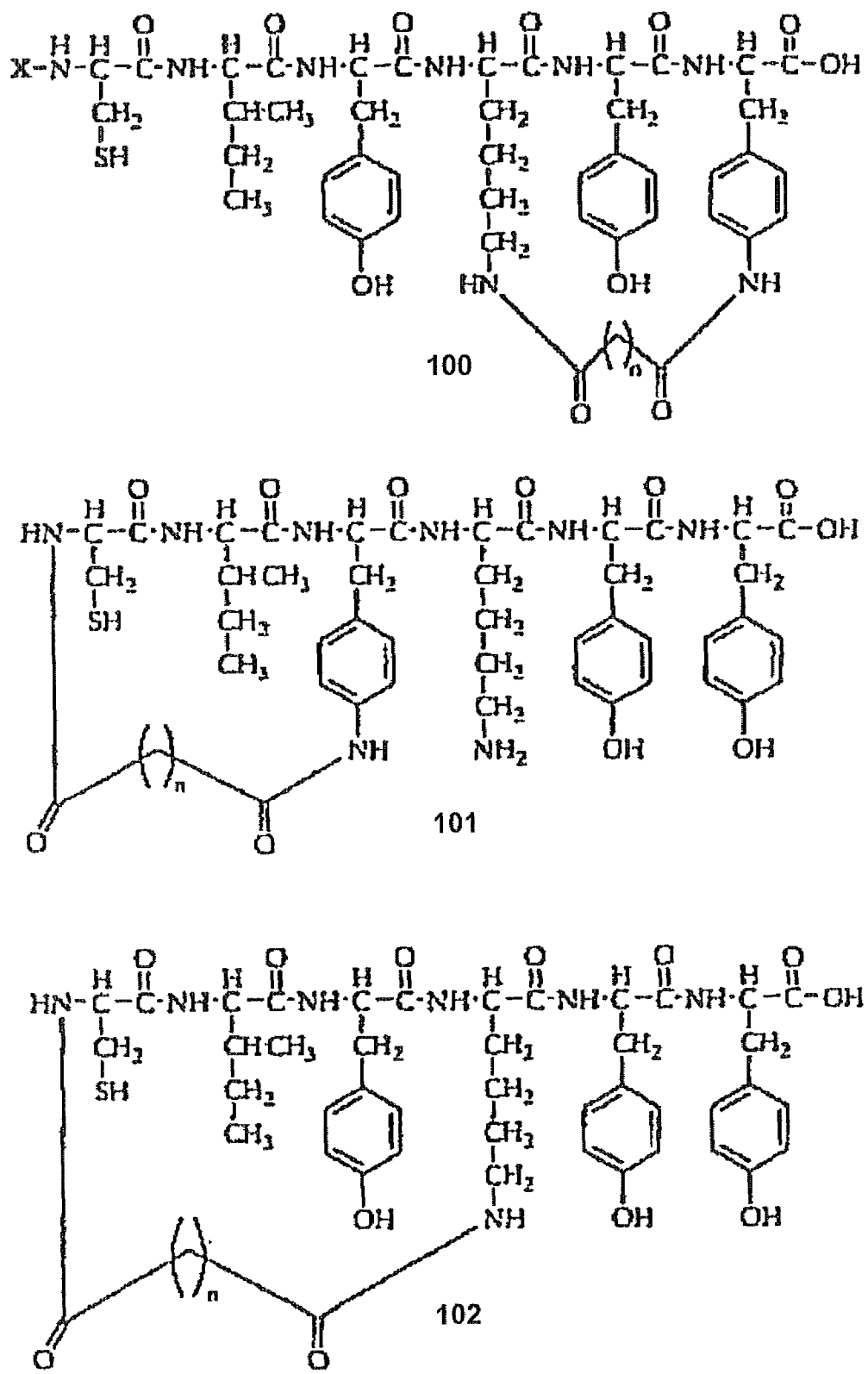
Figure 21:
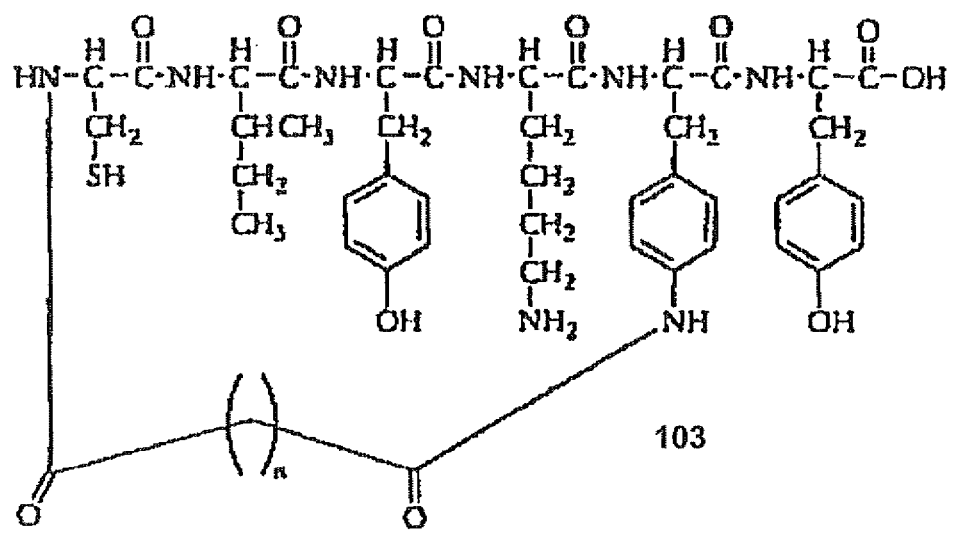
Figure 21:
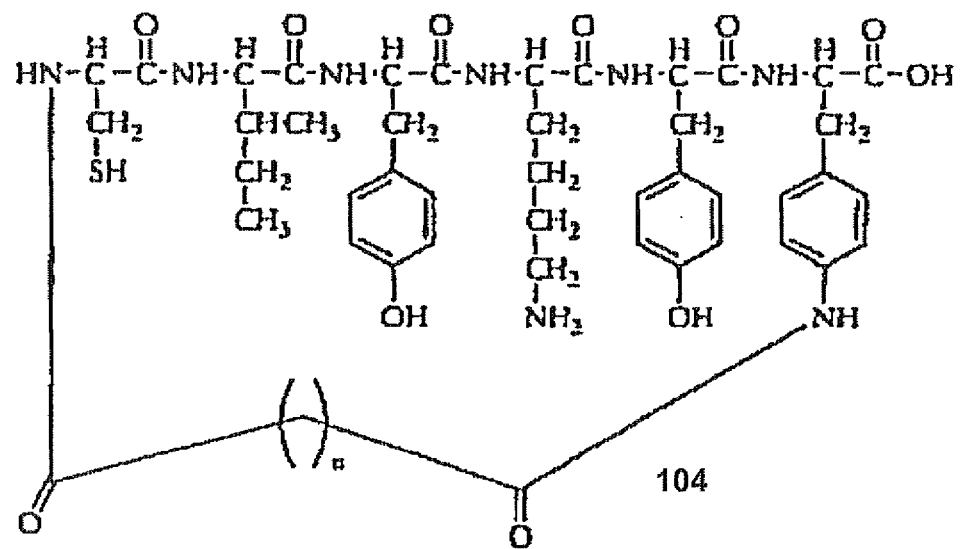
Figure 21:
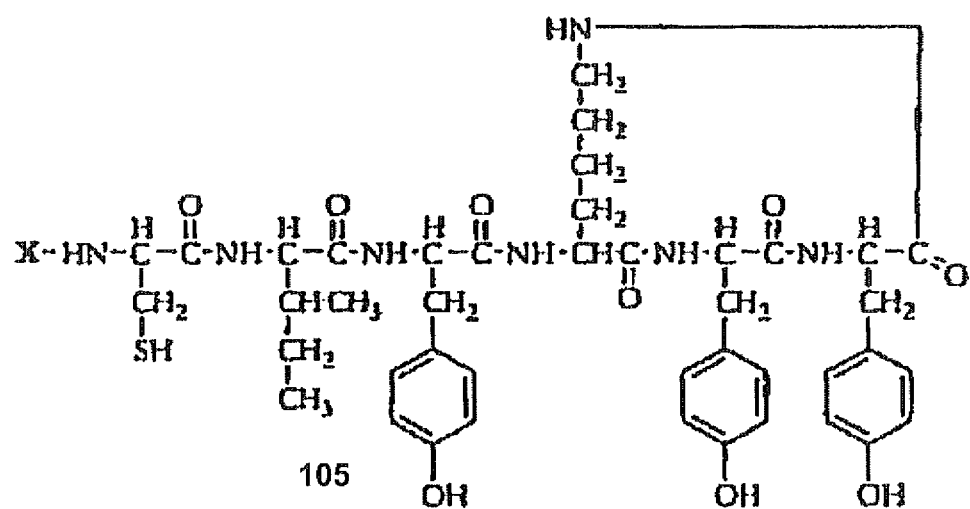

Due to the presence of three tyrosine residues and one lysine in the C$_1$I$_2$Y$_3$K$_4$Y$_5$Y$_6$ (SEQ ID NO: 2), there are several opportunities for linking side chains of amino acids and cyclization. We examined whether conformational constraints could improve the binding affinities to the kinase domain. FIG. 21 represents a series of conformationally constrained peptides based on a peptide sequence CIYKYY (SEQ ID NO: 2). In general, several of the constrained peptides with acetyl group in N-terminal (IC$_{50}$=1.9-75 μM range) among compounds 94-105 showed higher inhibitory potency relative to the corresponding linear peptides, 40 (IC$_{50}$=400 μM). The presence of the constrained ring had a dramatic effect on the binding, enhancing the affinity significantly over the acyclic analogs probably by creating novel binding interactions. Compounds 94-105 are shown here as some of the claimed compounds (FIG. 21). These compounds include peptides or heteroaromatic-peptide conjugates formed by side chain-side chain (e.g., 95-100), side chain-N-terminal (e.g., 101-104), or side chain-C-terminal (e.g. 105) cyclization. Other peptides listed in section C.2.7. are also used utilizing similar concept for cyclization and attachment to N-heteroaromatics.

Several N-heteroaromatic-peptide derivatives were prepared for targeting the ATP binding site and other potential sites. Taken together, a combination of empirical synthetic manipulation and mechanism-based design was used in producing optimized Src kinase inhibitors. Several lead compounds) can be used as templates for further optimization. Optimization includes cyclization of the peptide, attaching the peptide to different atoms in the N-heteroaromatics, using different N-heteroaromatics, and changing the nature of the peptide (sequence, size) and the linker (size, rigidity). The N-heteroaromatics cores such as pyrazolopyrimidine and pyrrolopyrimidine cores resemble the purine core of ATP itself and like PP1 and PP2, bind in the nucleotide binding site in the position normally occupied by the adenine base, and can bind to both down- and upregulated forms of the enzyme. Any substituent attached to N$_1$ of pyrazole or pyrrole occupies a mostly hydrophobic cavity. Most of this hydrophobic cavity remains unfilled. This cavity, in part, formed from side chains of helix αC and helix αD.

Figure 22:
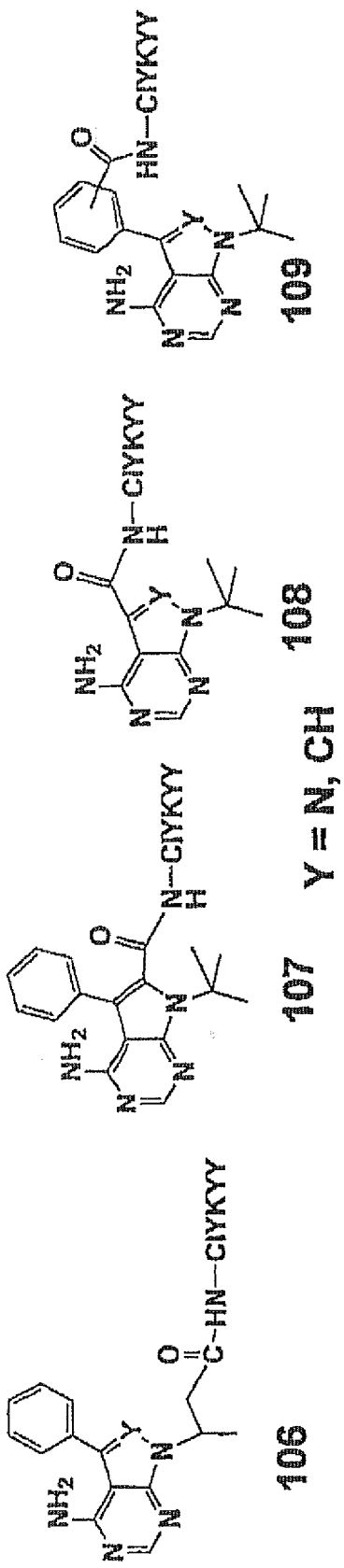
FIG. 22 shows bicyclic N-heteroaromatic-peptide conjugates with peptides attached to 3-phenyl, $N^1$, $C^2$, or $C^3$ position of heteroaromatic moiety (CIYKYY disclosed as SEQ ID NO: 2)

The N-heteroaromatics are connected by a linker to side chains of different amino acids in the peptides. Furthermore, different atoms of the heterocyclic compound are used for the attachment of the linker based on the molecular modeling studies and acquired inhibitory potency data. Compounds include the direct attachment of the peptide to N$_1$, C$_2$, C$_3$, of the bicyclic N-heteroaromatic group (such as those shown in compounds 106-109) (FIG. 22) and N-heteroaromatics including purine-based derivatives, pyrimidine-based derivatives such as 2,4-diamino-5-substituted pyrimidine derivatives, pyrazole[3,4-d]pyrimidine derivatives, pyrrolo[2,3-d]pyrimidine derivatives, pyrido[2,3-d]pyrimidine derivatives, amino-substituted dihydropyrimido[4,5-d]pyrimidinone derivatives, thieno- and furo-substituted derivatives, quinazoline derivatives, quinoline derivatives, and several natural products such as aminogenistein.

Figure 23:
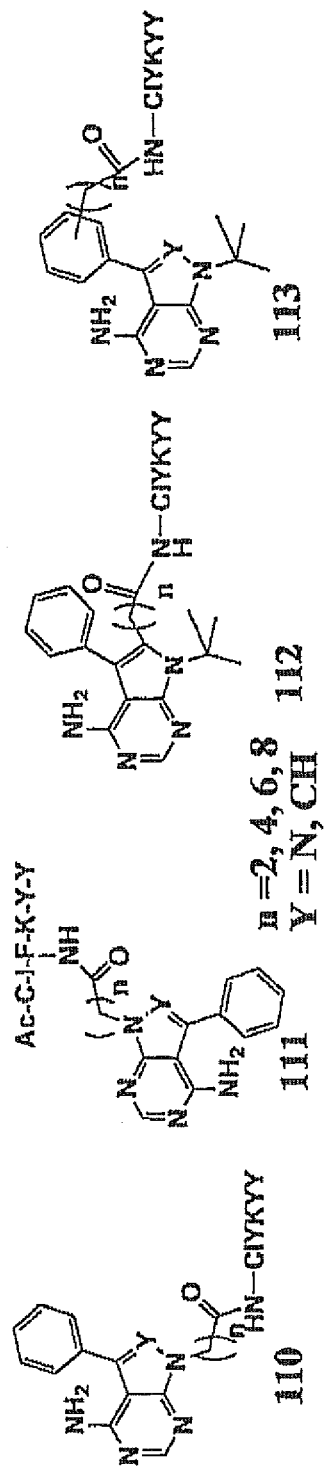
FIG. 23 shows proposed bicyclic N-heteroaromatic-peptide conjugates containing various linkers (CIYKYYY and CIFKYY disclosed as SEQ ID NOS 2 and 44 respectively)

Several linkers are claimed based on our modeling studies. The linker length and rigidity can be changed and optimized utilizing alkyl chains of varying length and rigidity including those shown in FIG. 12. Some examples of rigid linkers include glycine, γ-aminobutyric acid, or phenyl. Compounds 110 and 111 are examples of disclosed compounds. Other derivatives include conjugates containing peptides located in C$_2$ and 3-phenyl positions of the heteroaromatic ring (e.g., 112 and 113) (FIG. 23) and N-heteroaromatics including purine-based derivatives, pyrimidine-based derivatives such as 2,4-diamino-5-substituted pyrimidine derivatives, pyrazole[3,4-d]pyrimidine derivatives, pyrrolo[2,3-d]pyrimidine derivatives, pyrido[2,3-d]pyrimidine derivatives, amino-substituted dihydropyrimido [4,5-d]pyrimidinone derivatives, thieno- and furo-substituted derivatives, quinazoline derivatives, quinoline derivatives, and several natural products such as aminogenistein. The number of the linker groups can be modified.

Experimental

Material and Methods (Fmoc-Tyr(tBu) Wang resin, Fmoc-Phe(4-NO$_2$)-Wang resin and Fmoc protected amino acids were purchased from Novabiochem. Fmoc-Phe(4-Guanidine(Boc)$_2$)—OH was purchased from Advanced Chemtech. All other chemical were purchased from Fischer Scientific Company and were used as received. HPLC purification was performed on a PHENOMENEX® Prodigy 10μ ODS reversed phase column eluting at 6.0 mL/min using water (0.01% TFA) and acetonitrile (0.01% TFA) as eluent with a gradient of 0-100% over 65 min. The high resolution electrospray ionization mass stereoscopy (ESI-MS) was performed on PE Biosystem API 2000 electrospray mass spectrometer.

Synthesis of Peptides and Bicyclic N-Heteroaromatic-Peptide Conjugates. Synthesis of Peptides In general, all peptide were synthesized by the solid phase peptide synthesis strategy on a PS3 automated peptide synthesizer (Renin Instrument Co., Inc.) employing Fmoc based chemistry. NMM (0.4M) and HBTU (1 equivalent to amino acid) in N,N-dimethylformamide (DMF) were used a activating and coupling reagent, respectively. Piperidine (20% in DMF) was used for deprotection of Fmoc at each step and N-terminal acetylation was accomplished by using acetic anhydride. Finally a mixture of TFA (90%), anisole (3%), water (3%), thioanisole (2%) and 1,2-dithioethanol (2%) was used for side chain deprotection of amino acids and cleavage of the peptide from the resin. The crude peptide were precipitated by addition of cold diethyl ether and centrifuged. The precipitated peptides were purified by preparative HPLC. The purity and chemical structure of peptides were confirmed by high resolution ESI-MS.

Figure 24:
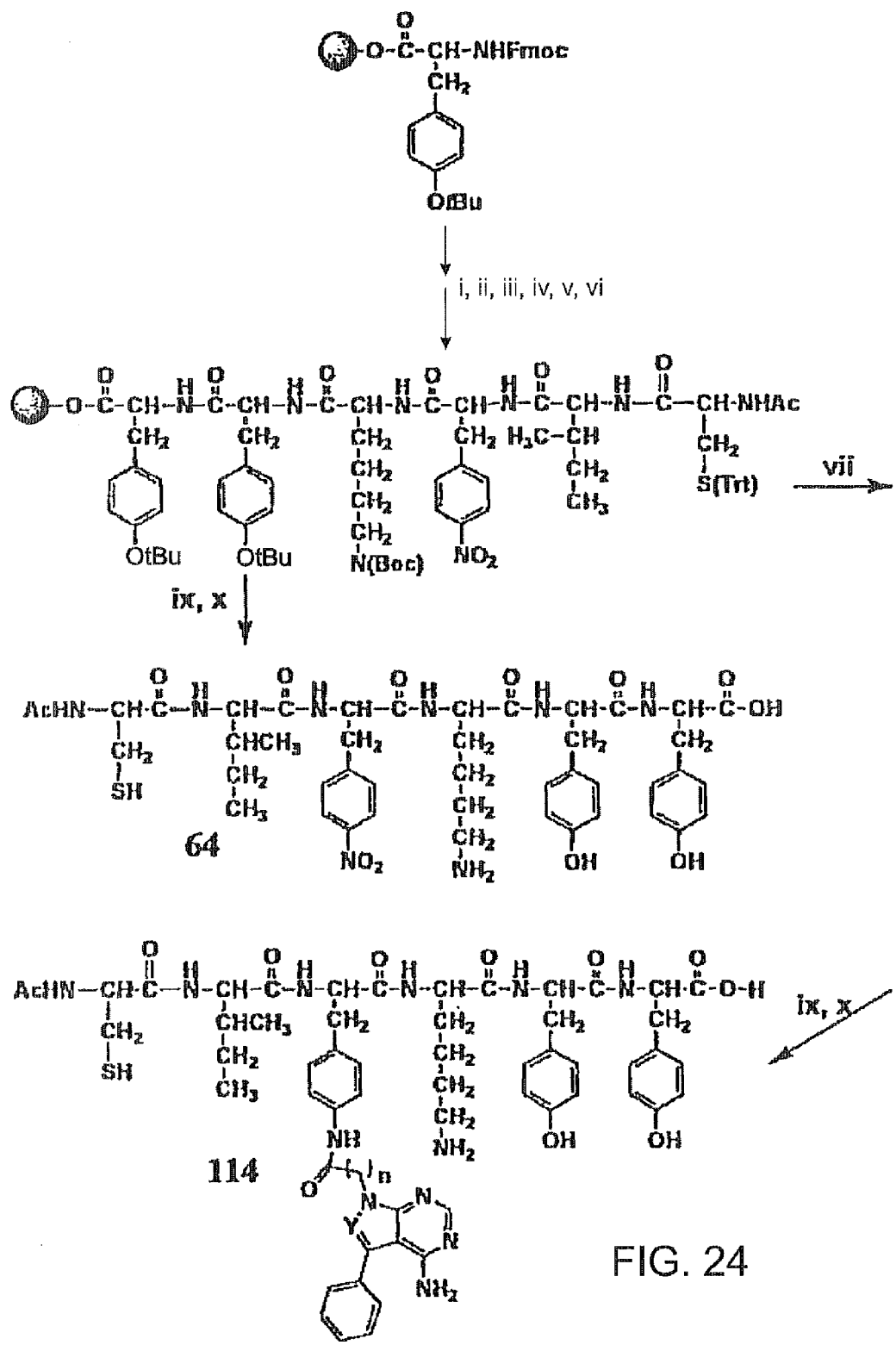
FIG. 24 shows the synthetic procedure for the preparation of nitropeptide 64 and pyrazolpyrimidine-peptide conjugate 114. Reagents: (i) Fmoc-Tyr(OtBu)-OH, HBTU, NMM, piperidine, DMF; (ii) Fmoc-Lys(Boc)-OH,HBTU, NMM, piperidine, DMF; (iii) Fmoc-Phe(4-NO$_2$)—OH, HBTU, NMM, piperidine, DMF; (iv) Fmoc-Ile-OH, HBTU, NMM, piperidine, DMF; (v) Fmoc-Cys(Trt)-OH, HBTU, NMM, piperidine, DMF; (vi) Acetic anhydride, DMF; (vii) SnCl$_2$.2H$_2$O in DMF (2N); (viii) HBTU, NMM; (ix) 2% Hydrazine hydrate in DMF; (x) TFA: anisole:water:phenol:EDT (90:2.5:2.5:2.5: 2.5)
Figure 24:
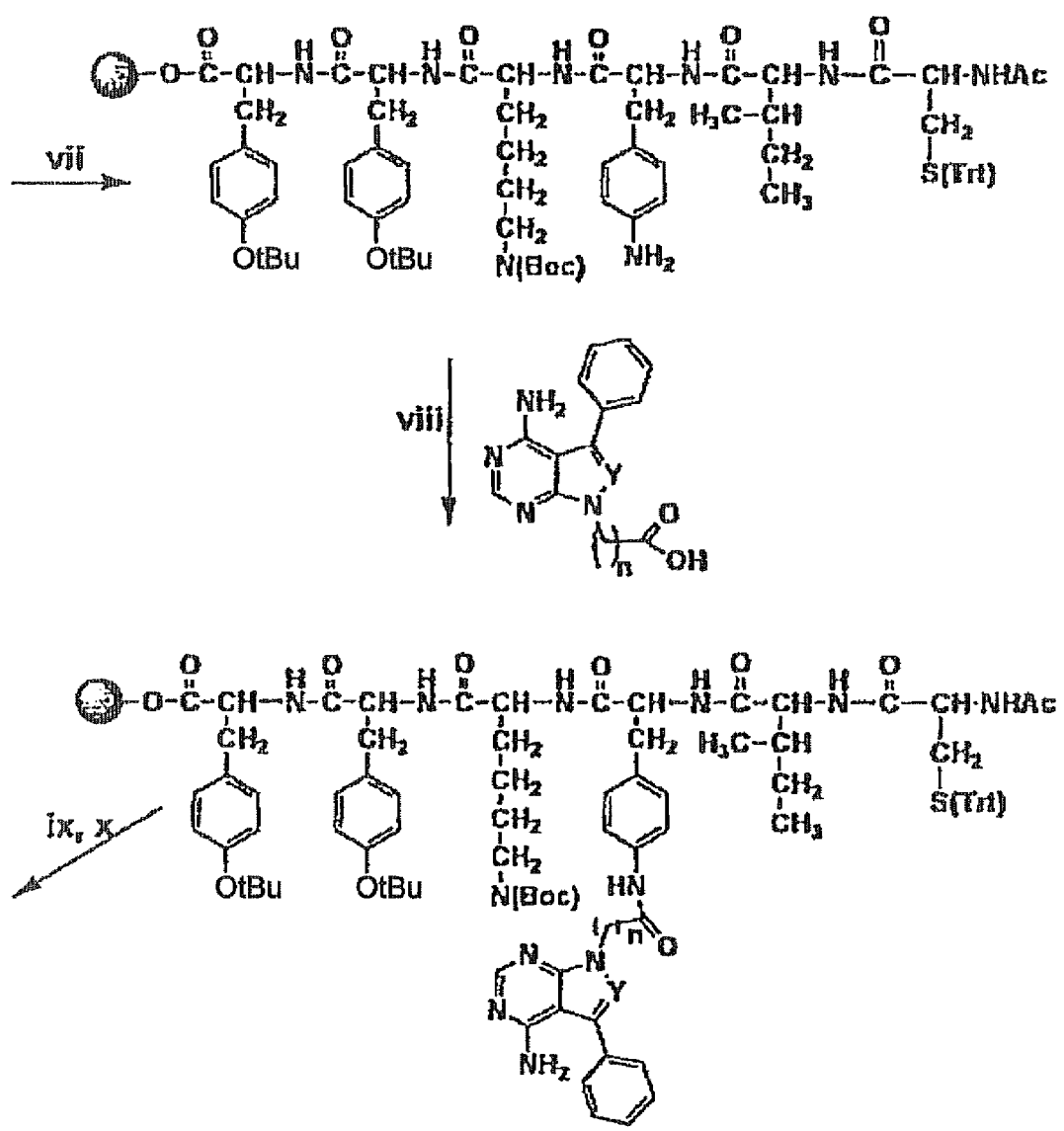
Figure 25:
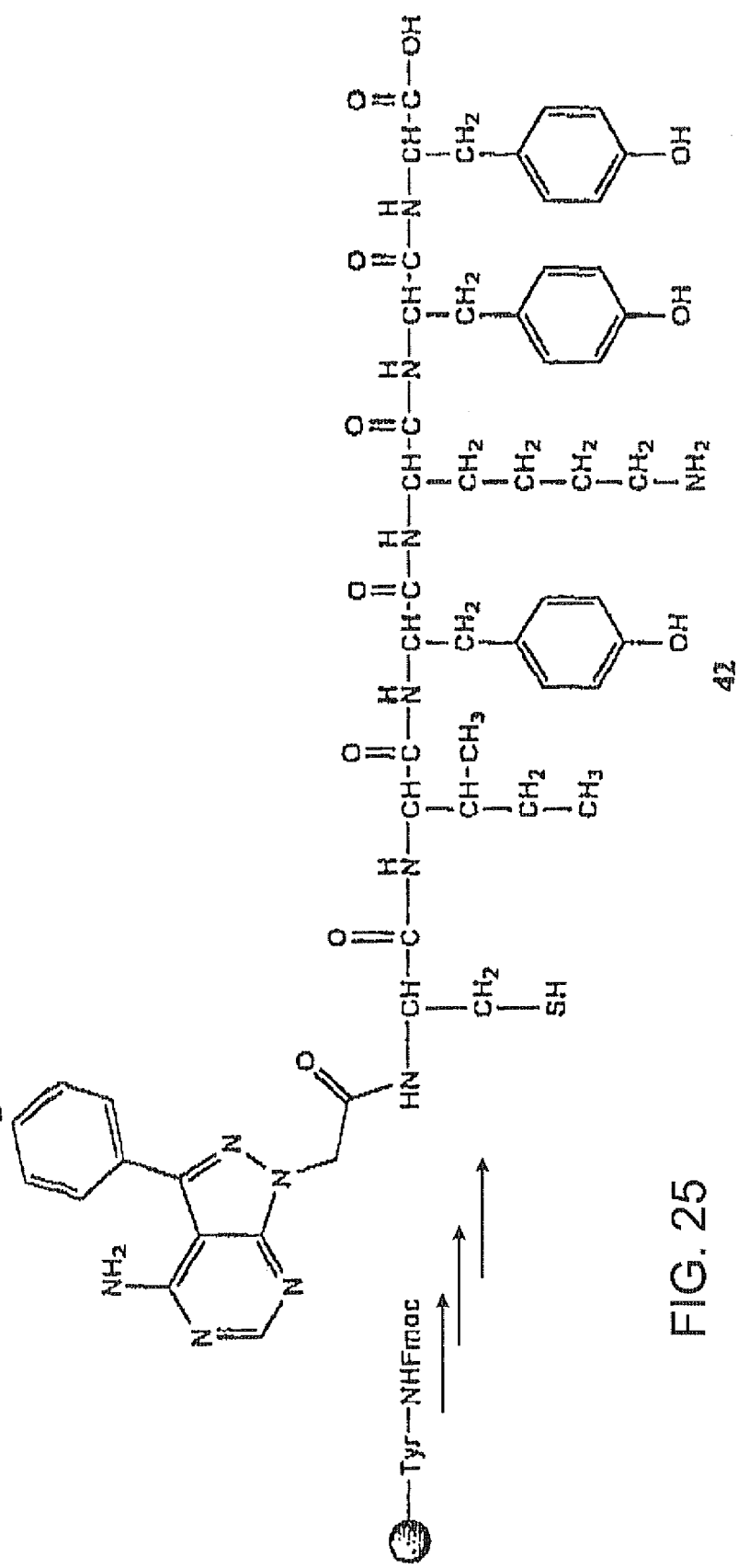
FIG. 25 shows the synthesis of heteroaromatic-peptide conjugates with N-heteroaromatics attached to the N-terminal of the peptide (SEQ ID NOS 37-39, respectively, in order of appearance)
Figure 25:
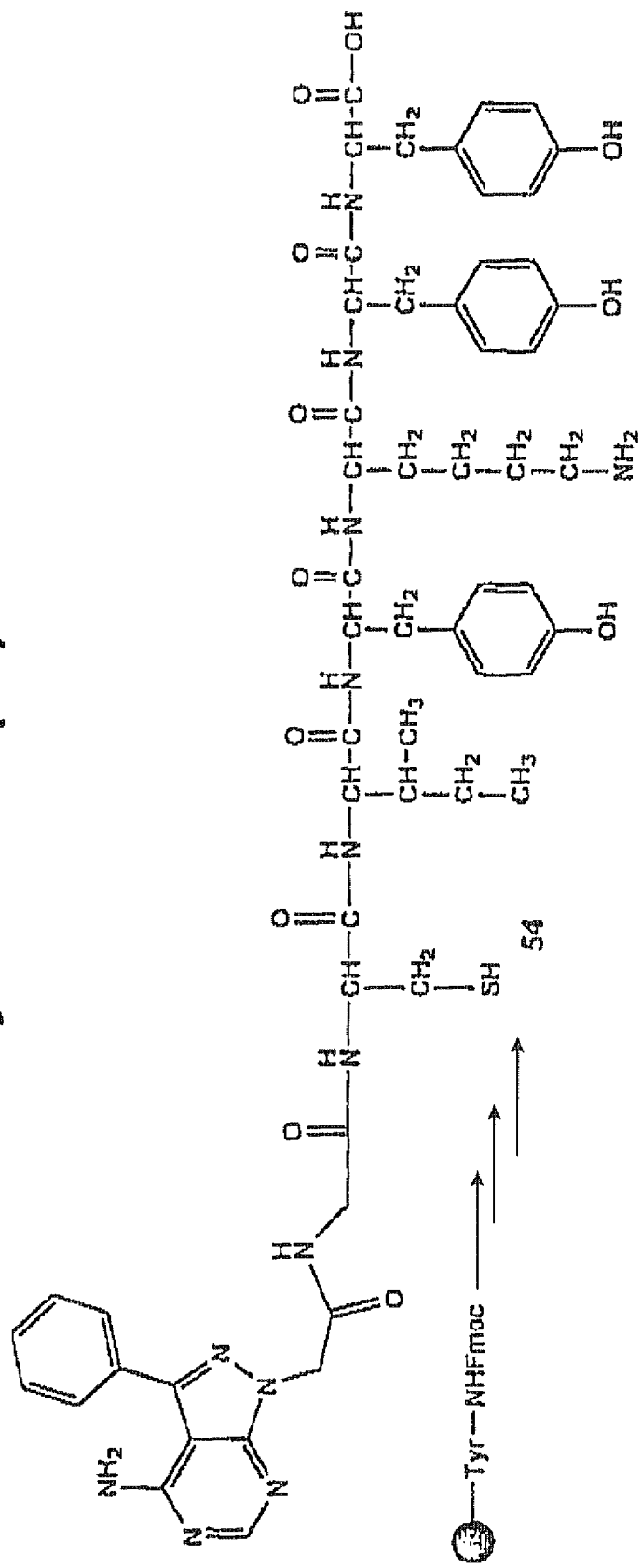
Figure 25:
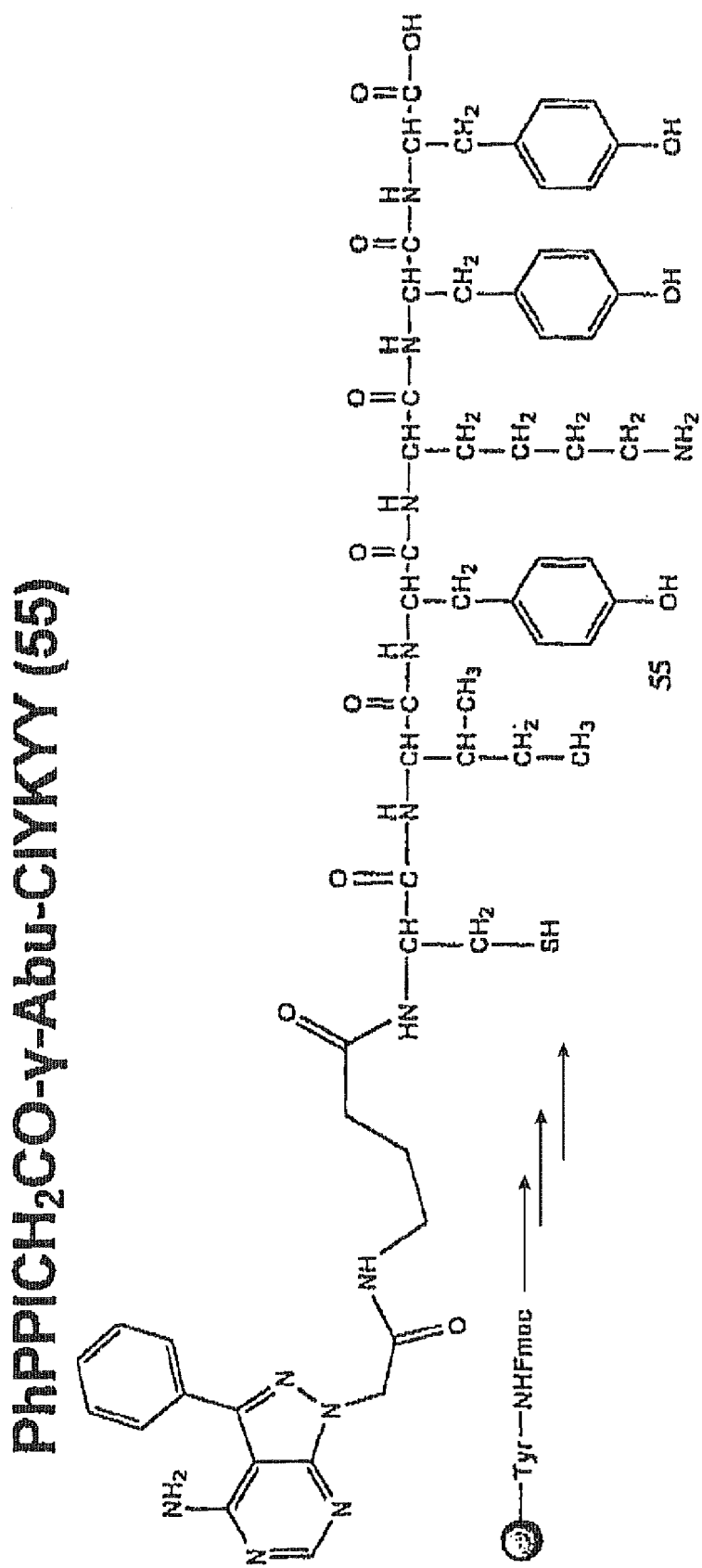
Figure 26:
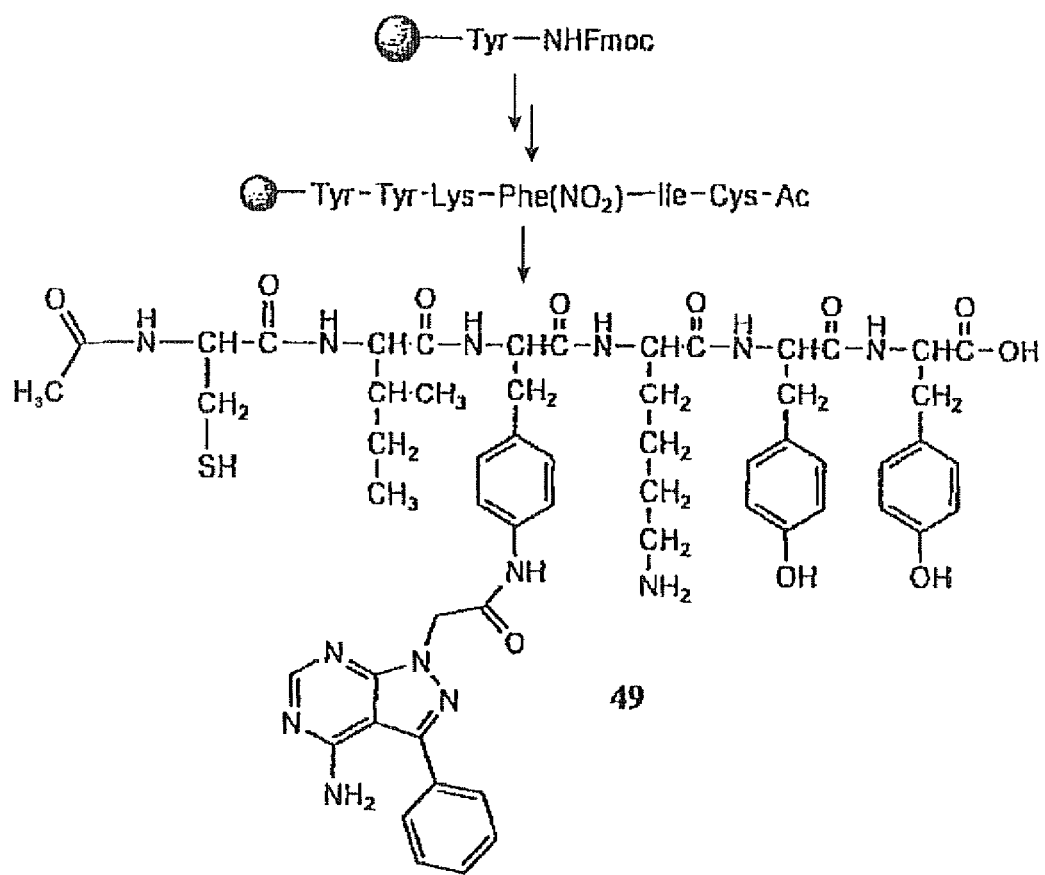
FIG. 26 shows the synthesis of heteroaromatic-peptide conjugates (SEQ ID NOS 40, 15, 41, 2, 42, 15, 43 and 16, respectively, in order of appearance) with N-heteroaromatics attached to the side chains of different amino acids in the peptide.
Figure 26:
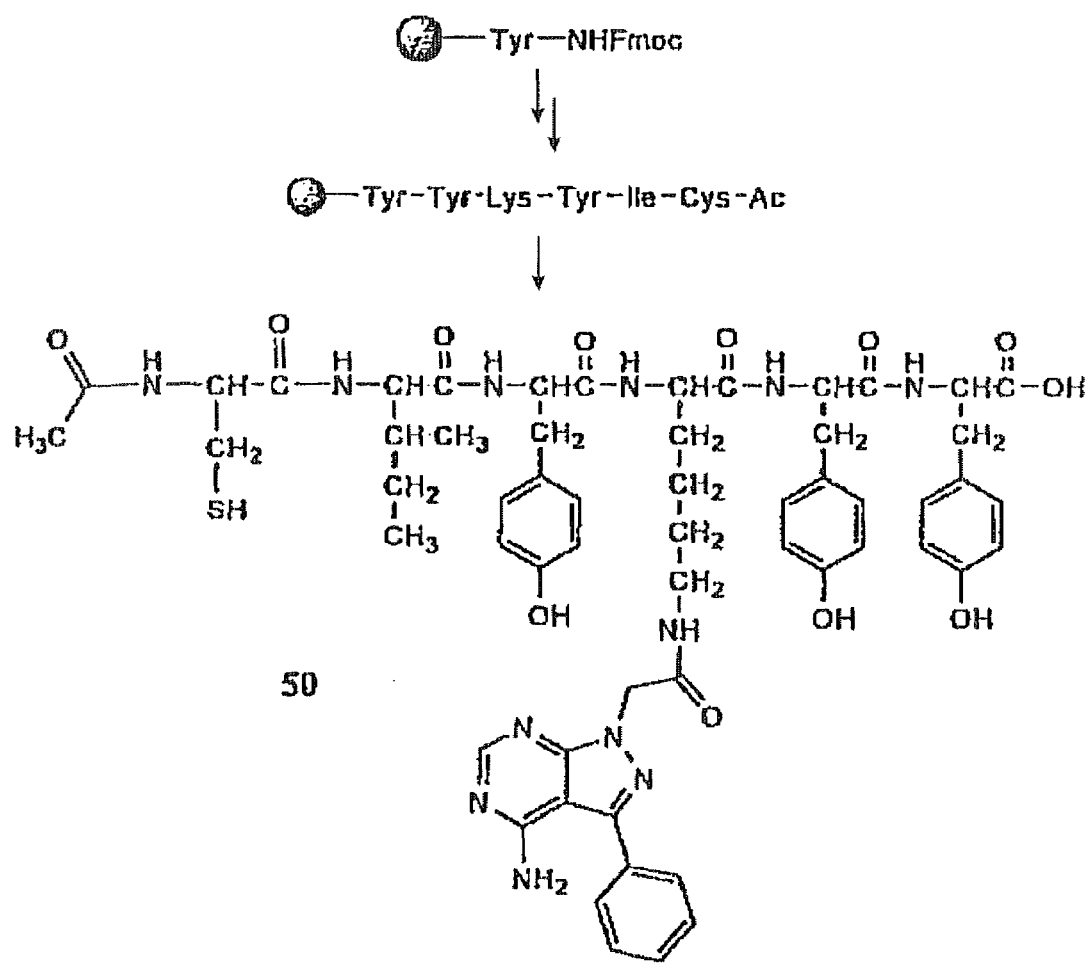
Figure 26:
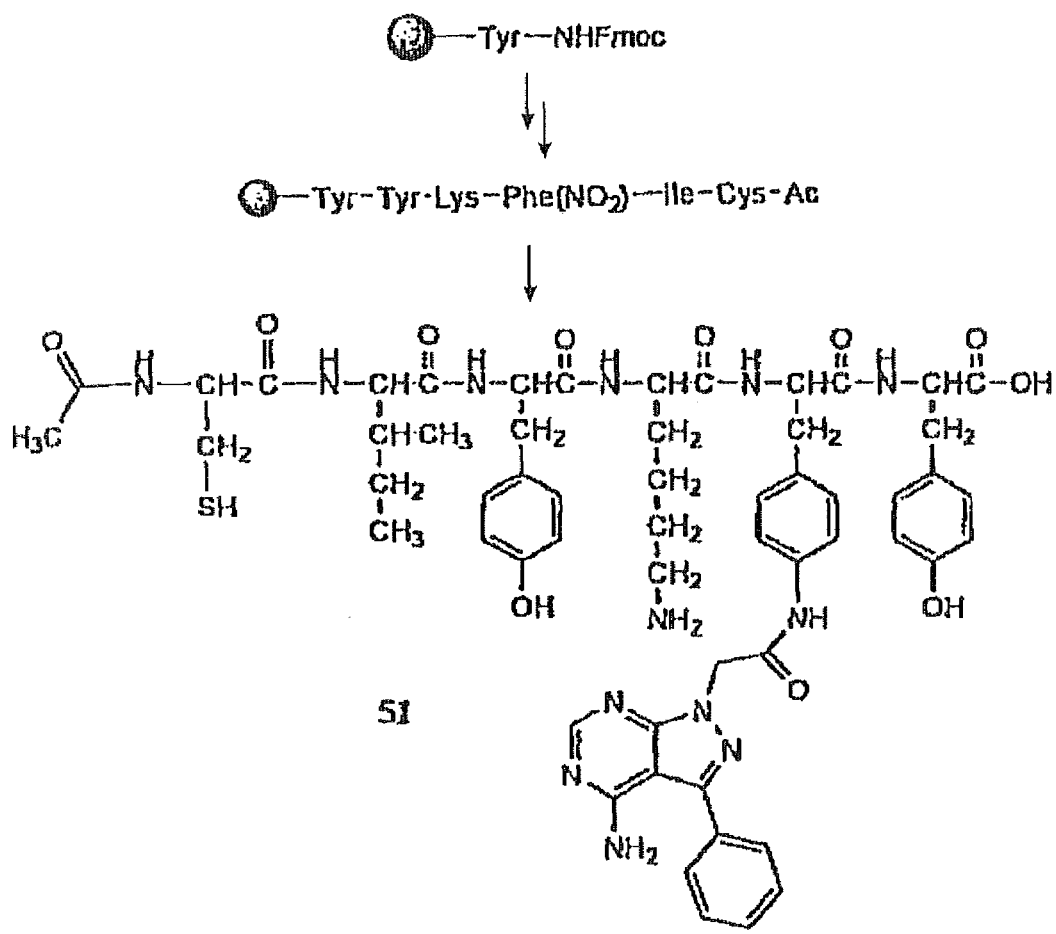
Figure 26:
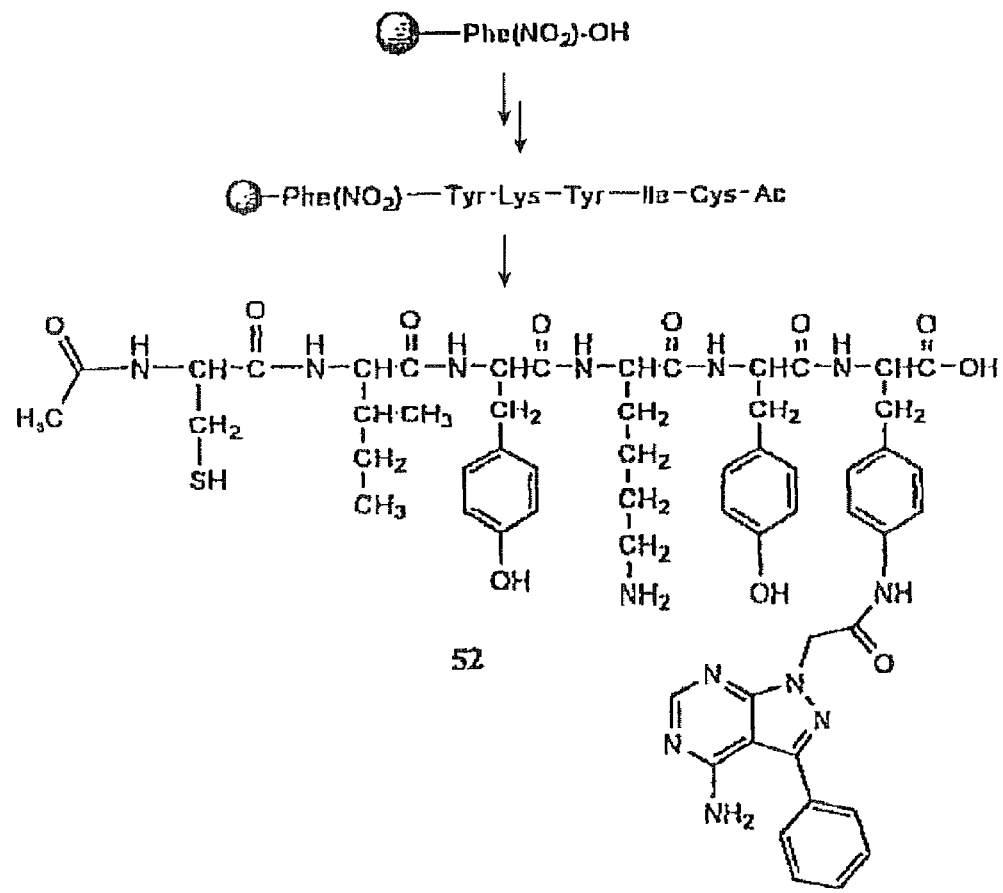

These synthetic strategies for conjugates are straightforward. The peptides were assembled on solid phase (Wang resin) using a standard Fmoc peptide protocol with HBTU/NMM as coupling reagents. Peptides were N-terminally acetylated. Those with nitrophenylalanine residue replacing the tyrosine in the peptide were reduced to aminophenylalanine with stannous chloride under acidic conditions. The resin-linked peptide will be reacted with bicyclic N-heteroaromatics substituted with alkyl- or arylcarboxylic acid functional groups in the presence of HBTU. Compounds were cleaved from solid support, deblocked, and purified by reversed-phase HPLC. As a representative example, the synthesis of peptide 64 and N-heteroaromatic-peptide conjugate 114 is shown in FIG. 24. The synthesis of several other compounds is summarized in FIGS. 25 and 26.

Compounds were characterized by a Bruker NMR DPX400 (400 MHz) and a high-resolution PE Biosystems Mariner API time of flight and API 2000 (LC/MS/MS) mass spectrometers. HPLC purity of crude products was determined. Electrospray ionization-mass spectrometry accommodates on-line chromatographic separation of products in complex mixtures.

Figure 27:
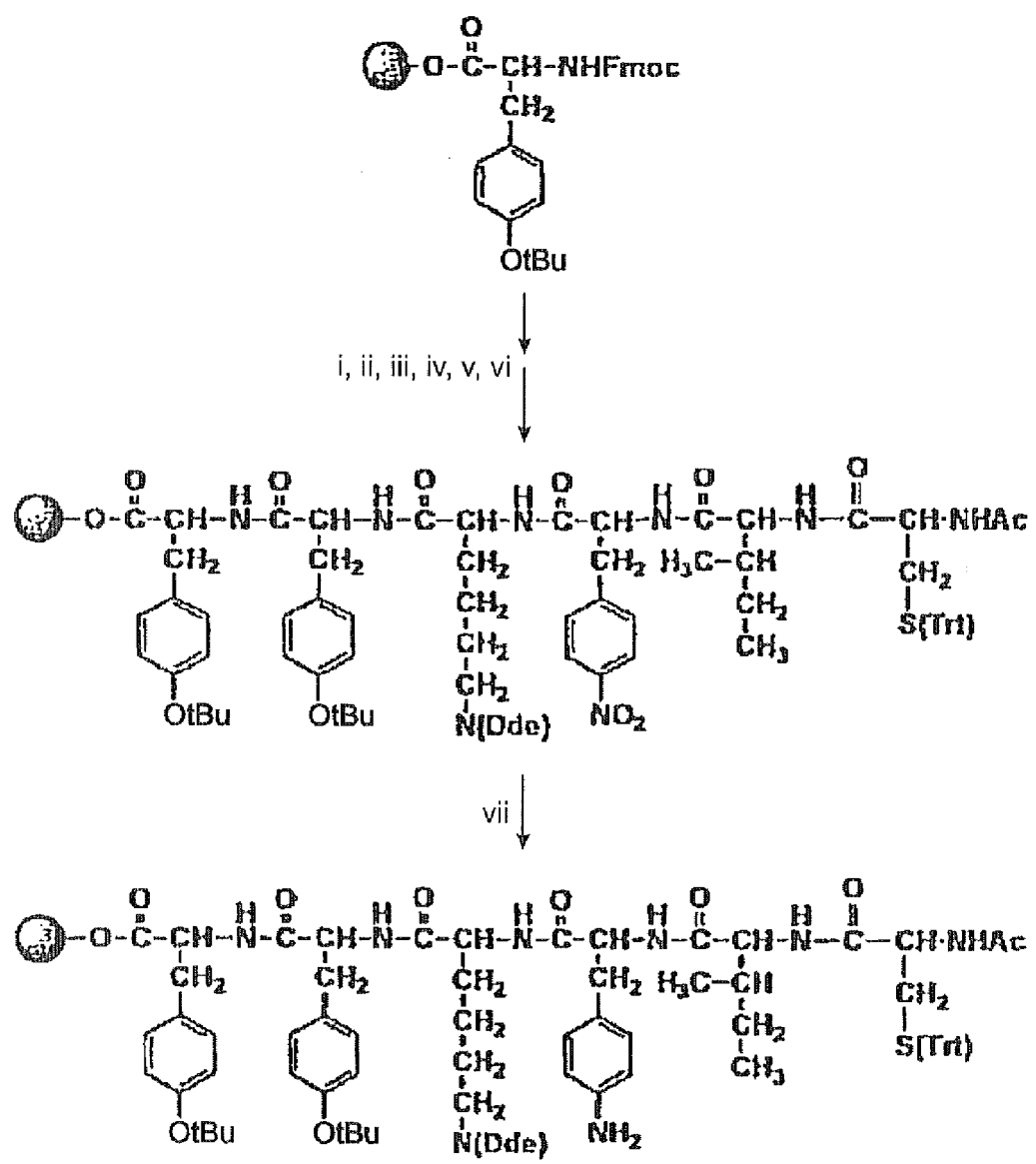
FIG. 27 shows the synthetic procedure for the cyclization of peptides. Reagents: (i) Fmoc-Tyr(OtBu)-OH, HBTU, NMM, piperidine, DMF; (ii) Fmoc-Lys(Dde)-OH,HBTU, NMM, piperidine, DMF; (iii) Fmoc-Phe(4-NO$_2$)—OH, HBTU, NMM, piperidine, DMF; (iv) Fmoc-Ile-OH, HBTU, NMM, piperidine, DMF; (v) Fmoc-Cys(Trt)-OH, HBTU, NMM, piperidine, DMF; (vi) Acetic anhydride, DMF; (vii) SnCl$_2$.2H$_2$O in DMF (2N); (viii) Succinic anhydride, NMM, DMF or diacids, HBTU, NMM, DMF; (ix) 2% Hydrazine hydrate in DMF; (x) HBTU, NMM; (xi) TFA: anisole:water: phenol:EDT (90:2.5:2.5:2.5:2.5)
Figure 27:
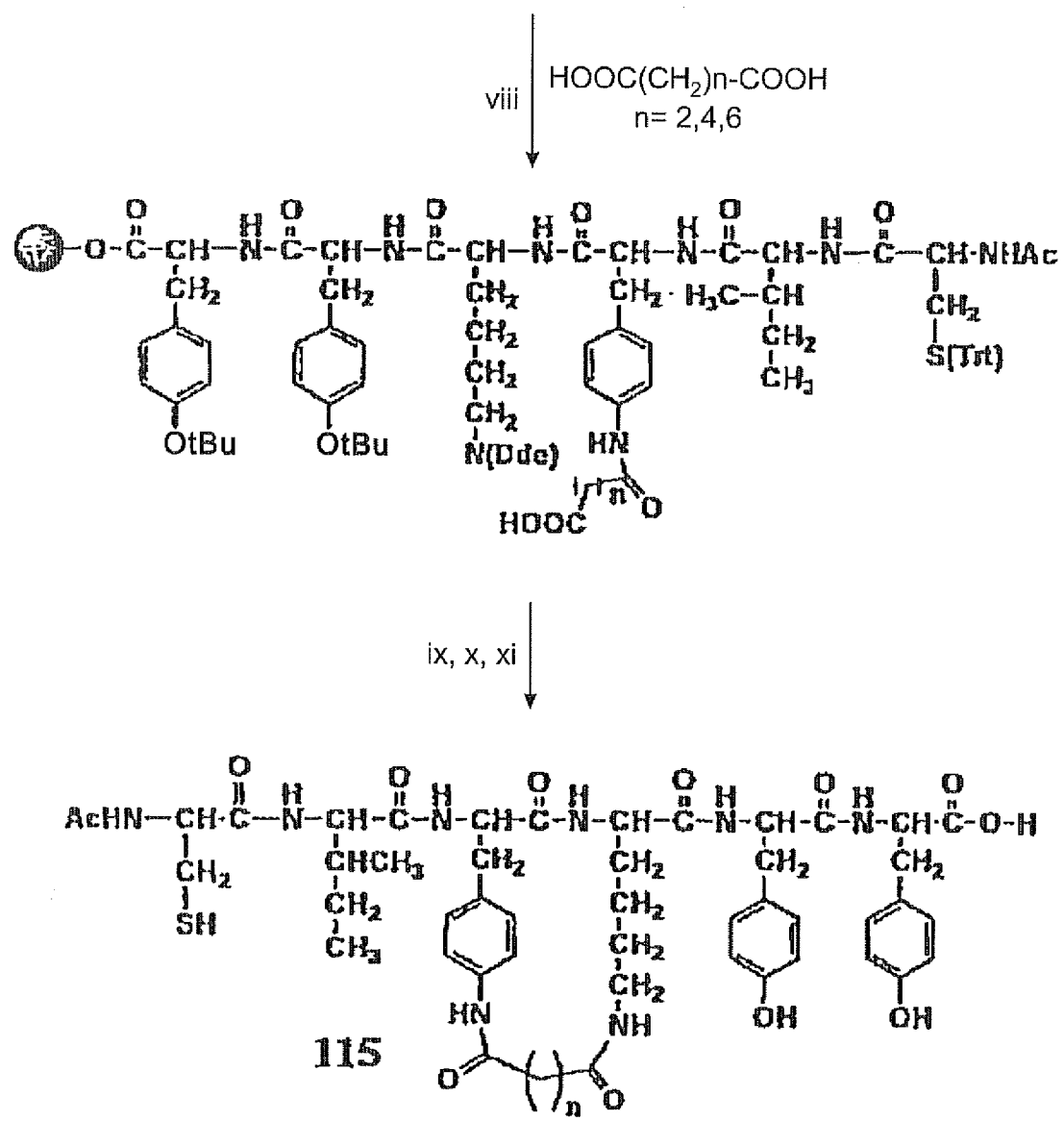

Synthesis of Cyclic Peptides:

In general, cyclic peptides were synthesized by using nitrophenylalanine and lysine (Dde) and sequential deprotection by tin chloride and hydrazine, respectively. For example (FIG. 27), the diacids or anhydrides can be attached to the side chain of phenylalanine after reduction of nitro first, followed by the deprotection of Dde and cyclization. Alternatively, diacids or anhydrides can be attached to the side chain of lysine, followed by cyclization with appropriate reduced nitrophenylalanine. Furthermore, the heteroaromatics can be coupled to the N-terminal or other side chains according to the methods described above.

Steady-State Kinetic Assays:

Steady-state kinetic assays were carried out using a radioactive assay according to the previously reported procedure. This assay contains polyE$_4$Y as the phosphate accepting substrate, [γ-$^{32}$P]-ATP, and MgCl$_2$. Percentage of inhibition will be plotted as a function of the compound concentration and the IC$_{50}$ value (the concentration of a compound that caused 50% inhibition) can be obtained from such a plot.

The pharmaceutical compositions of this invention may be prepared by combining compounds 1-6, 21-23, 42-114 with a solid or liquid pharmaceutically acceptable carrier, and optionally, with pharmaceutically acceptable adjuvants and excipients employing standard and conventional techniques. Solid form compositions include powders, tablets, dispersible granules, capsules and suppositories. A solid carrier may be at least one substance which may also function as a diluent, flavoring agent, solubilizer, lubricant, suspending agent, binder, tablet disintegrating agent, and encapsulating agent. Inert solid carriers include magnesium stearate, talc, sugar, lactose, pectin, dextrin, starch, gelatin, cellulosic materials, low melting wax, cocoa butter, and the like. Liquid form compositions include solutions, suspensions, and emulsions. For example, there may be provided solutions of the compounds of this invention dissolved in water, water-propylene glycol, and water-polyethylene glycol systems, optionally containing conventional coloring agents, flavoring agents, stabilizers and thickening agents.

The pharmaceutical compositions may be administered to human subjects suffering from cancer, bone-related diseases, such as osteoporosis, inflammation-mediated bone loss, rheumatoid arthritis, periodontal disease, Paget's disease, hypercalcaemia of malignancy and metastasis of certain cancers to bone, cardiovascular disorders such as myocardial infarction and injury that results from a VEGF-mediated increase in vascular permeability such as that seen following stroke, e.g. topically or systemically. Systemic routes of administration can include oral, intravenous, intramuscular or subcutaneous injection (including depots for long-term release), intraocular or retrobulbar, intrathecal, intraperitoneal (e.g. by intraperitoneal lavage), transpulmonary using aerosolized or nebulized drug, or transdermal. Topical routes include administration in the form of ointments, gels, salves, ophthalmic drops or ear drops. The therapeutically effective amount of the active component in the administered pharmaceutical composition may be readily determined by good medical practice and the clinical condition of the human subject being treated.

The invention claimed is:

1. A bisubstrate inhibitor of Src kinases selected from the group consisting of:

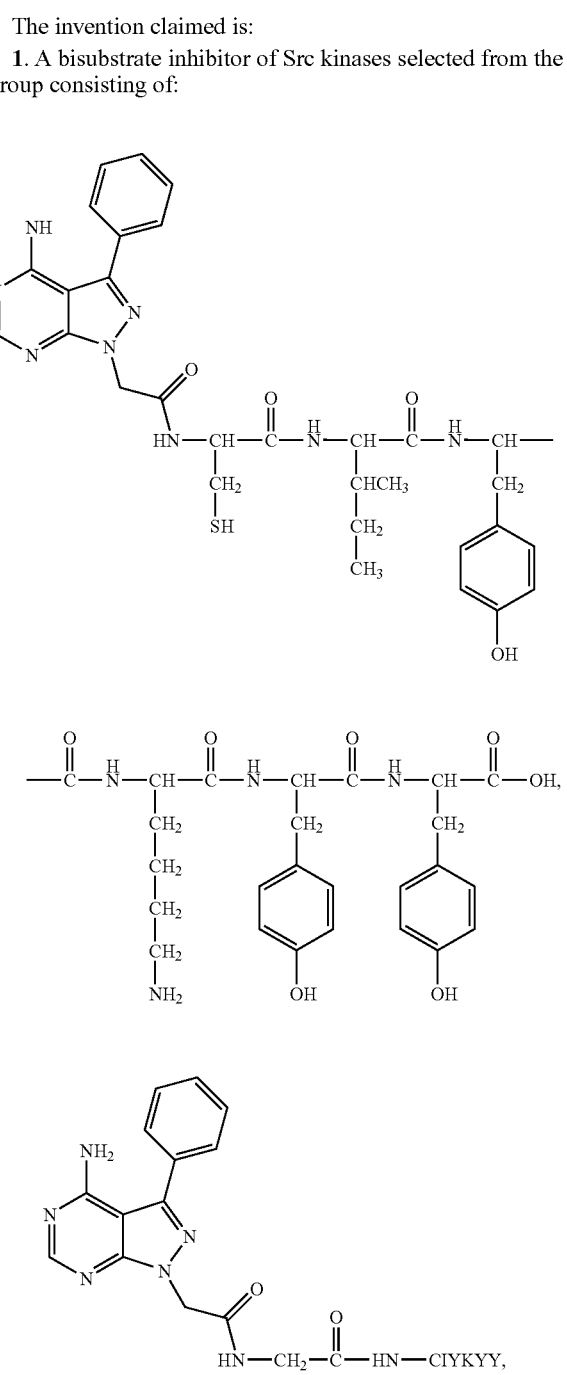

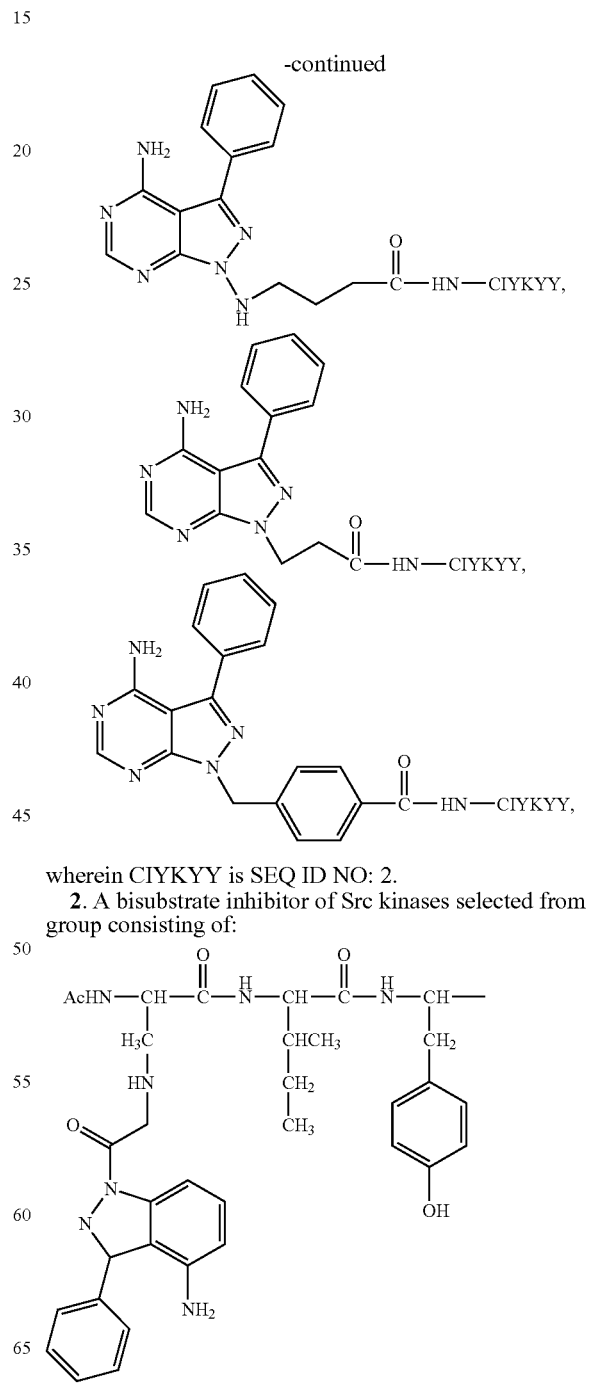

wherein CIYKYY is SEQ ID NO: 2.

2. A bisubstrate inhibitor of Src kinases selected from the group consisting of:

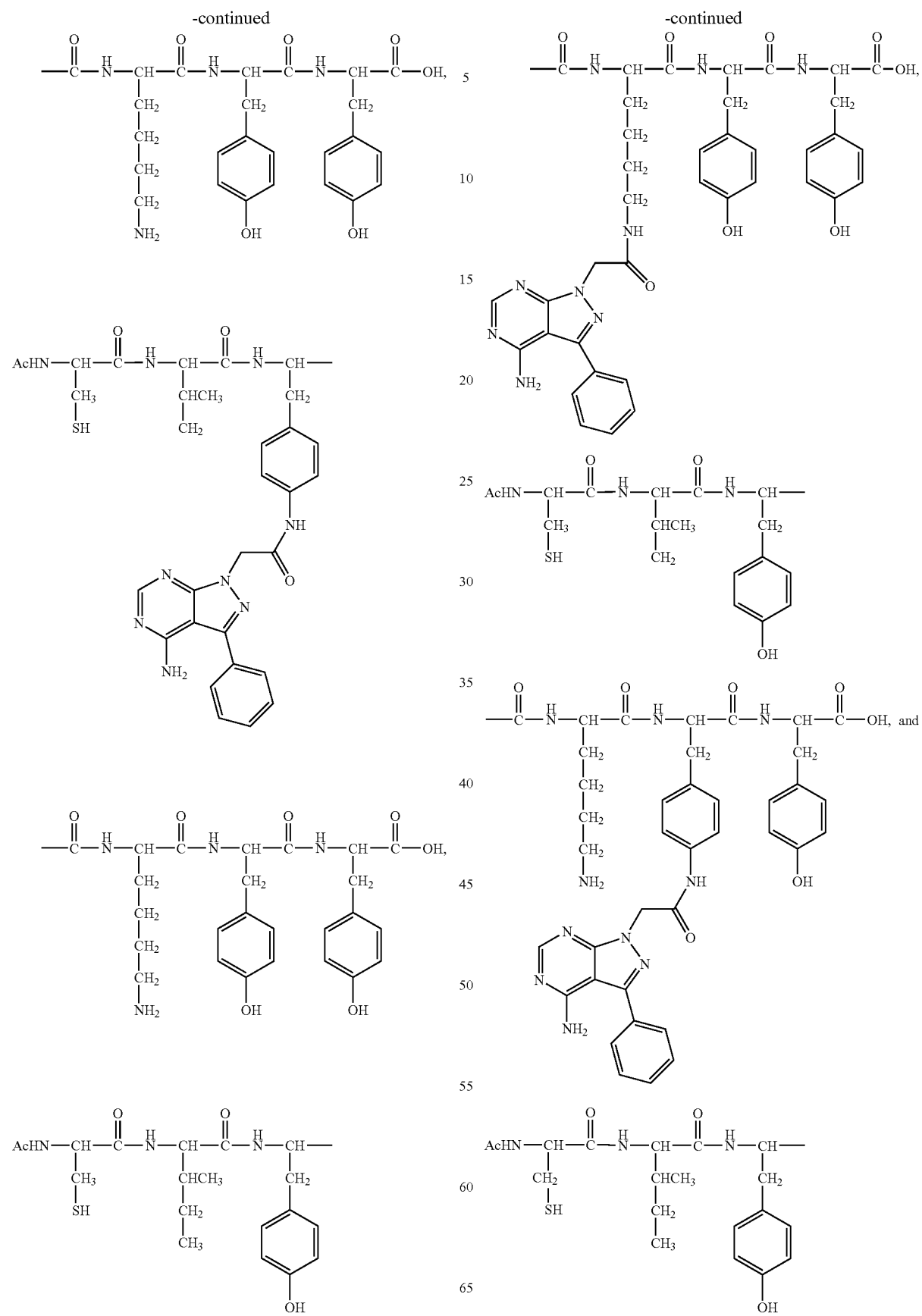

-continued
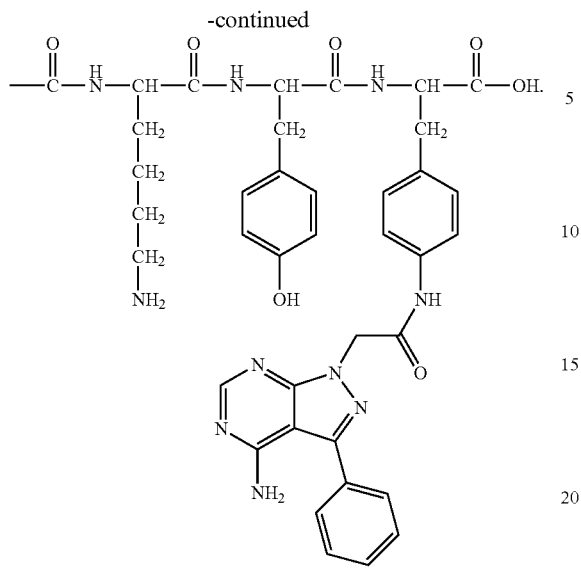
3. A bisubstrate inhibitor of Src kinases selected from the group consisting of:
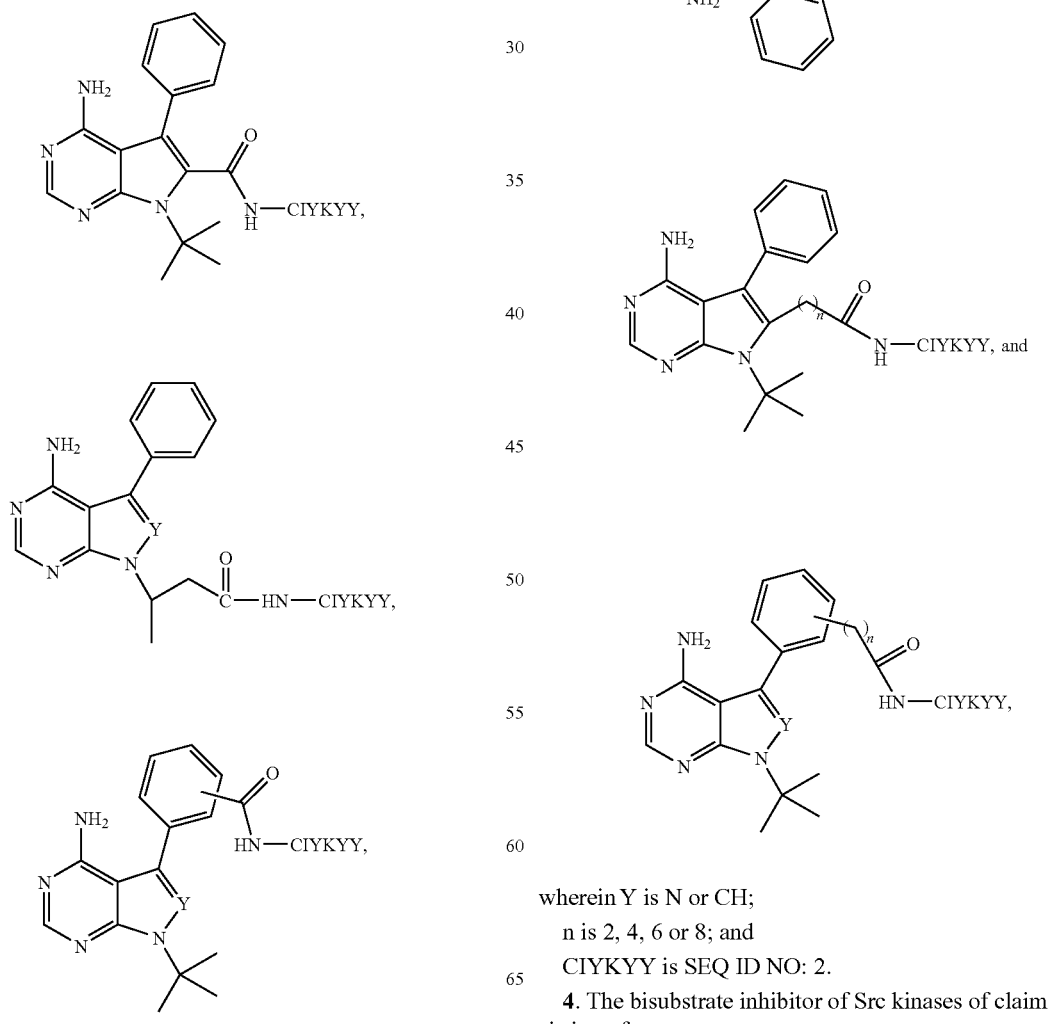
wherein Y is N or CH;
n is 2, 4, 6 or 8; and
CIYKYY is SEQ ID NO: 2.
4. The bisubstrate inhibitor of Src kinases of claim 1 consisting of

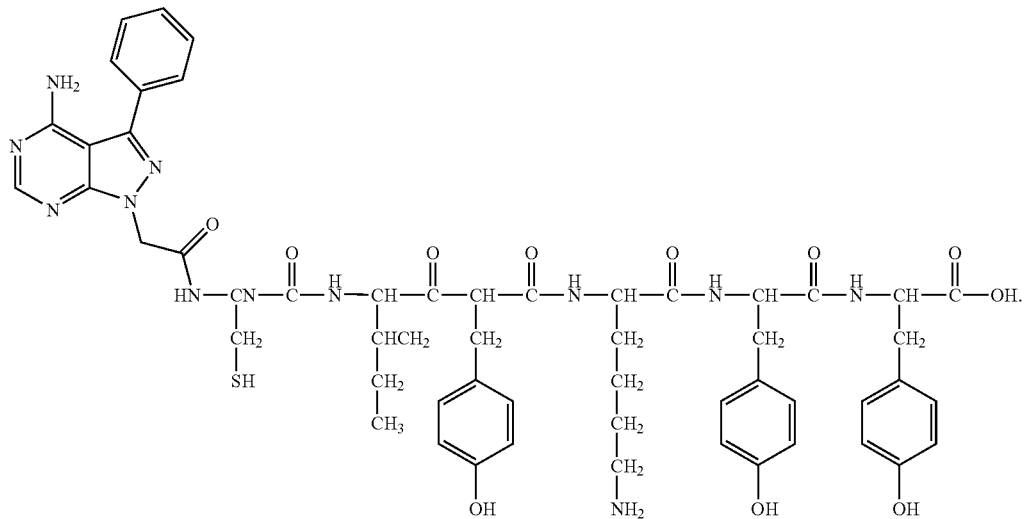

5. The bisubstrate inhibitor of Src kinases of claim 1 consisting of

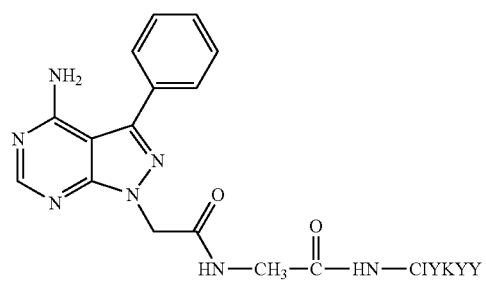

wherein CIYKYY is SEQ ID NO: 2.

6. The bisubstrate inhibitor of Src kinases of claim 1 consisting of

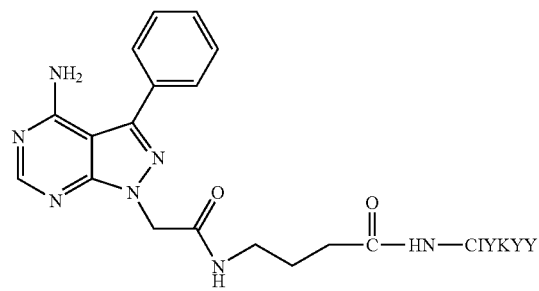

wherein CIYKYY is SEQ ID NO: 2.

7. The bisubstrate inhibitor of Src kinases of claim 1 consisting of

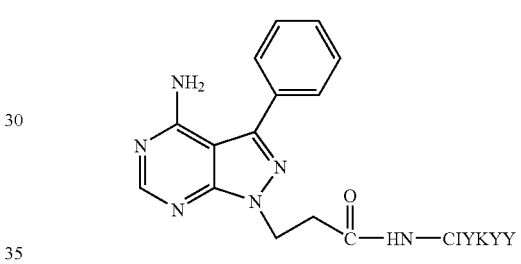

wherein CIYKYY is SEQ ID NO: 2.

8. The bisubstrate inhibitor of Src kinases of claim 1 consisting of

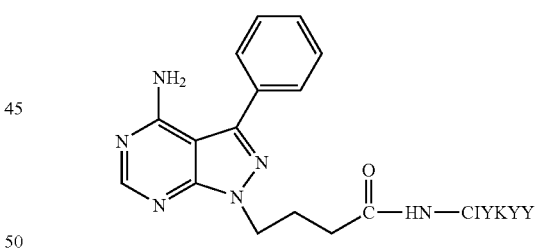

wherein CIYKYY is SEQ ID NO: 2.

9. The bisubstrate inhibitor of Src kinases of claim 1 consisting of

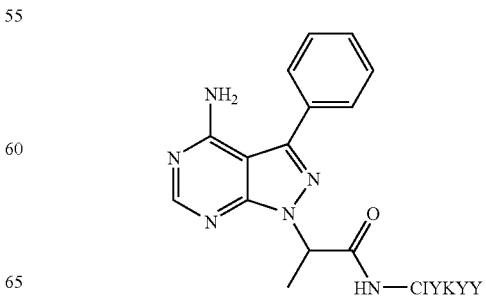

wherein CIYKYY is SEQ ID NO: 2.

10. The bisubstrate inhibitor of Src kinases of claim 1 consisting of
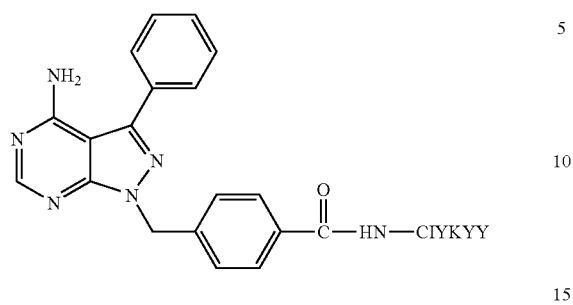
wherein CIYKYY is SEQ ID NO: 2.
11. The bisubstrate inhibitor of Src kinases of claim 2 consisting of
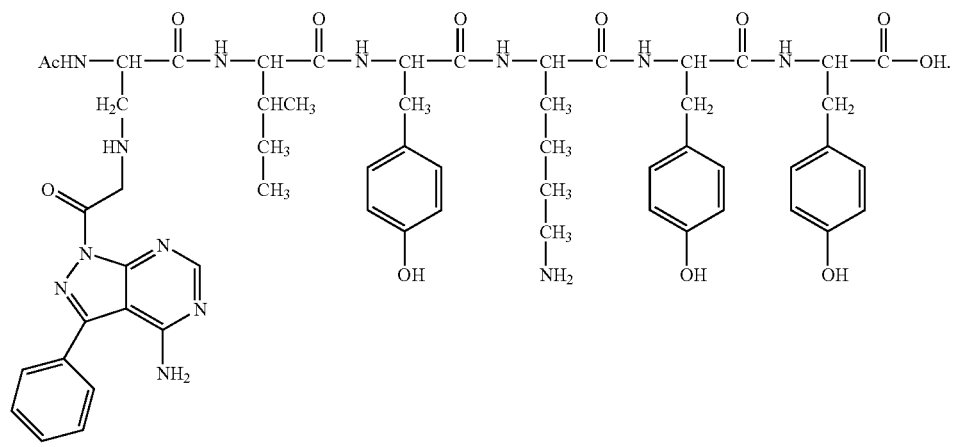
12. The bisubstrate inhibitor of Src kinases of claim 2 consisting of
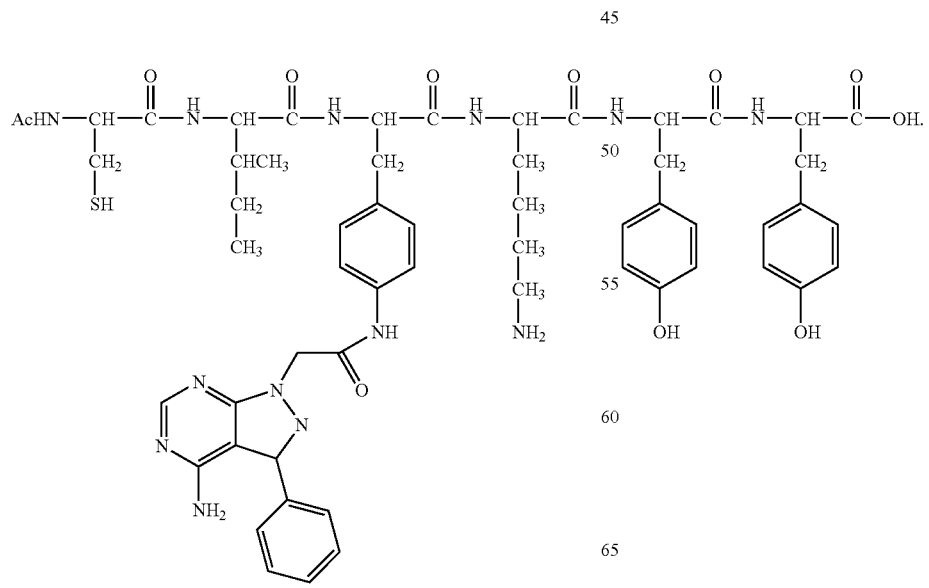

13. The bisubstrate inhibitor of Src kinases of claim 2 consisting of
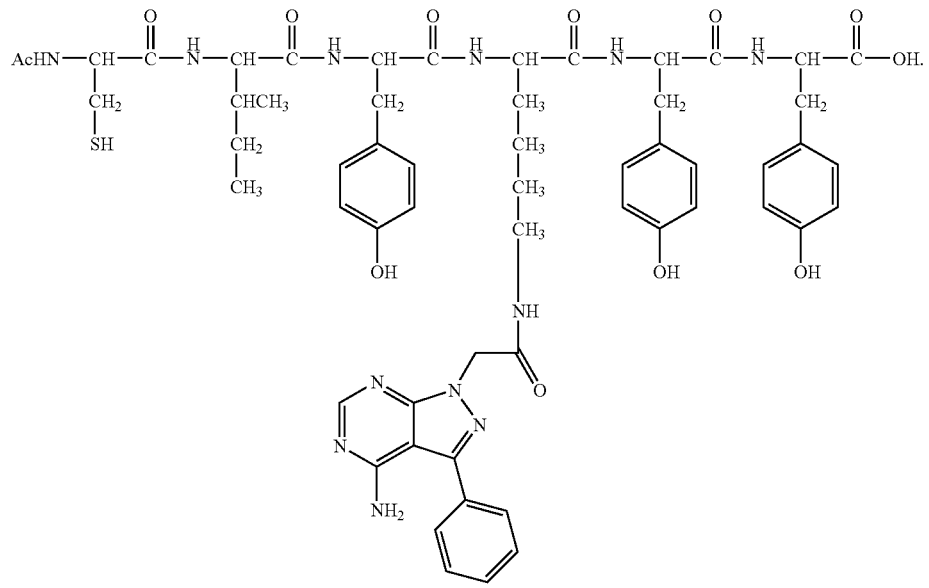
14. The bisubstrate inhibitor of Src kinases of claim 2 consisting of
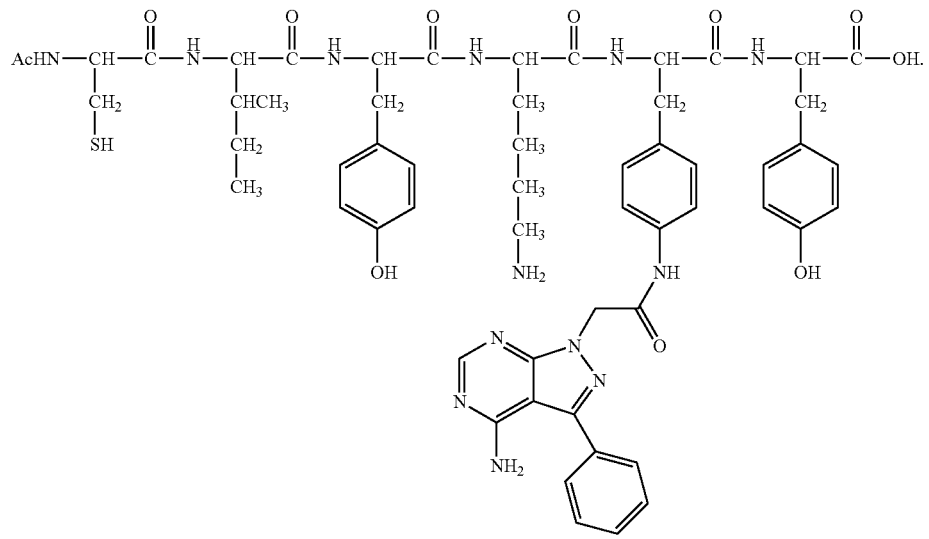
15. The bisubstrate inhibitor of Src kinases of claim 2 consisting of

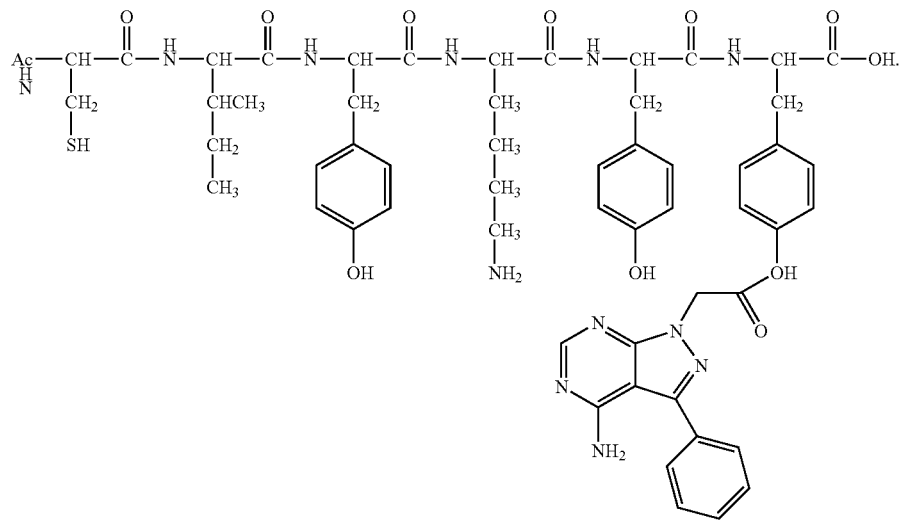

16. The bisubstrate inhibitor of Src kinases of claim 3 consisting of

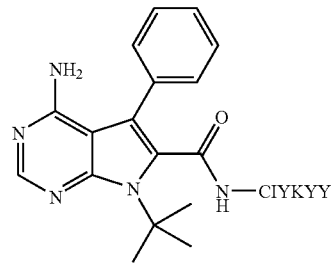

wherein CIYKYY is SEQ ID NO: 2.

17. The bisubstrate inhibitor of Src kinases of claim 3 consisting of

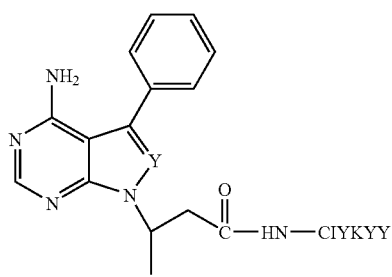

wherein Y is N or CH; and
CIYKYY is SEQ ID NO: 2.

18. The bisubstrate inhibitor of Src kinases of claim 3 consisting of

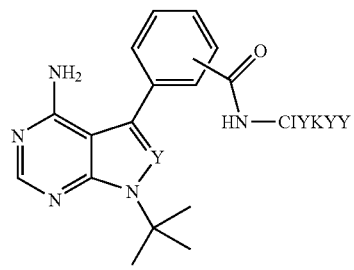

wherein Y is N or CH; and
CIYKYY is SEQ ID NO: 2.

19. The bisubstrate inhibitor of Src kinases of claim 3 consisting of

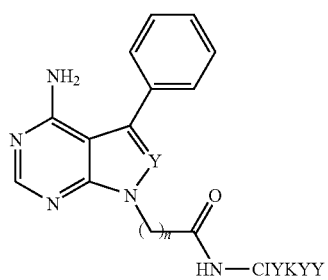

wherein Y is N or CH;
n is 2, 4, 6 or 8; and
CIYKYY is SEQ ID NO: 2.

20. The bisubstrate inhibitor of Src kinases of claim 3 consisting of

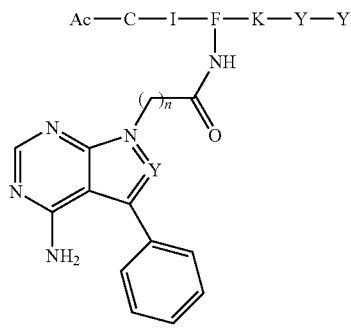

wherein Y is N or CH;
n is 2, 4, 6 or 8; and
CIYKYY is SEQ ID NO: 2.

21. The bisubstrate inhibitor of Src kinases of claim 3 consisting of

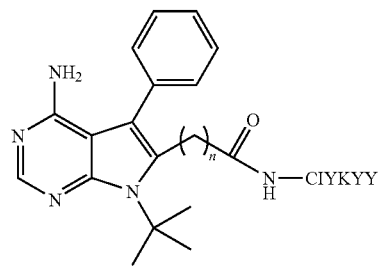

wherein Y is N or CH;
n is 2, 4, 6 or 8; and
CIYKYY is SEQ ID NO: 2.

22. The bisubstrate inhibitor of Src kinases of claim 3 consisting of

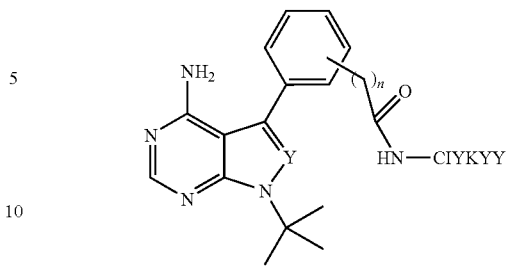

wherein Y is N or CH;
n is 2, 4, 6 or 8; and
CIYKYY is SEQ ID NO: 2.

23. A composition comprising a bisubstrate inhibitor of Src kinases of claim 1, 2, or 3.

24. A method of making a bisubstrate inhibitor of claim 2 comprising:

assembling the peptide CIYKYY (SEQ ID NO: 2) on solid phase resin using N-(9-fluorenyl)methoxycarbonyl (Fmoc)-based chemistry and Fmoc-protected amino acids or resins in the presence of 2(1H-benzotriazole-1-yl)-1,1,3,3-tetramethyluronium hexafluorophosphate (HBTU) and N-methylmorpholine in DMF as coupling and activating agents, respectively;

reacting the resin-linked peptide with 3-phenylpyrazolpyrimidine-substituted with alkyl- or arylcarboxylic acids in the presence of HBTU and N,N-diisopropylethylamine; and deprotecting and cleaving from solid support in the presence of TFA/water/anisole/ethanedithiol to afford N-terminal substituted 3-phenylpyrazolpyrimidine-peptide conjugates.

* * * * *

UNITED STATES PATENT AND TRADEMARK OFFICE
CERTIFICATE OF CORRECTION

PATENT NO. : 7,799,753 B2
APPLICATION NO. : 11/565914
DATED : September 21, 2010
INVENTOR(S) : Parang et al.

It is certified that error appears in the above-identified patent and that said Letters Patent is hereby corrected as shown below:

On the Title page, item (73); please delete "Assignees: Board of Governers for Higher Education, Providence, RI (US); State of Rhode Island and Providence Plantations, Providence, RI (US)" and replace with "Assignee: Board of Governors for Higher Education, State of Rhode Island and Providence Plantations, Providence, RI (US)".

Signed and Sealed this

Sixteenth Day of November, 2010

David J. Kappos
*Director of the United States Patent and Trademark Office*

SEQUENCE LISTING

```
<160> NUMBER OF SEQ ID NOS: 44

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 1

Tyr Ile Tyr Gly Ser Phe Lys
1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Cys Ile Tyr Lys Tyr Tyr
1               5

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phosphorylated-Tyr

<400> SEQUENCE: 3

Tyr Glu Glu Ile
1

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Phosphorylated-Tyr

<400> SEQUENCE: 4

Gly Tyr Glu Glu Ile
1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Ala
<220> FEATURE:
<221> NAME/KEY: MOD_RES
<222> LOCATION: (2)..(2)
<223> OTHER INFORMATION: Phosphorylated-Tyr

<400> SEQUENCE: 5

Ala Tyr Glu Glu Ile
1               5
```

```
<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 6-aminohexanoic acid
<220> FEATURE:
<221> NAME/KEY: MOD_RES
<222> LOCATION: (2)..(2)
<223> OTHER INFORMATION: Phosphorylated-Tyr

<400> SEQUENCE: 6

Xaa Tyr Glu Glu Ile
1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 8-aminooctanoic acid
<220> FEATURE:
<221> NAME/KEY: MOD_RES
<222> LOCATION: (2)..(2)
<223> OTHER INFORMATION: Phosphorylated-Tyr

<400> SEQUENCE: 7

Xaa Tyr Glu Glu Ile
1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 11-aminoundecanoic acid
<220> FEATURE:
<221> NAME/KEY: MOD_RES
<222> LOCATION: (2)..(2)
<223> OTHER INFORMATION: Phosphorylated-Tyr

<400> SEQUENCE: 8

Xaa Tyr Glu Glu Ile
1               5

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4,7,10-trioxa-1,13-tridecanediamine
      succinoyl-phosphorylated-Tyr
```

```
<400> SEQUENCE: 9

Tyr Glu Glu Ile
1

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 1,8-diamino-3,6-dioxaoctane
      succinoyl-phosphorylated-Tyr

<400> SEQUENCE: 10

Tyr Glu Glu Ile
1

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ile Tyr Lys Tyr Tyr
1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Nitrophenylalanine

<400> SEQUENCE: 12

Cys Ile Tyr Lys Phe Tyr
1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Aminophenylalanine

<400> SEQUENCE: 13

Cys Ile Tyr Lys Phe Tyr
1               5

<210> SEQ ID NO 14
<211> LENGTH: 6
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 14

Cys Ile Tyr Lys Phe Tyr
1               5

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Nitrophenylalanine

<400> SEQUENCE: 15

Cys Ile Phe Lys Tyr Tyr
1               5

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Nitrophenylalanine

<400> SEQUENCE: 16

Cys Ile Tyr Lys Tyr Phe
1               5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Aminophenylalanine

<400> SEQUENCE: 17

Cys Ile Phe Lys Tyr Tyr
1               5

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Aminophenylalanine
```

```
<400> SEQUENCE: 18

Cys Ile Tyr Lys Tyr Phe
1               5

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Nitrophenylalanine
<220> FEATURE:
<221> NAME/KEY: MOD_RES
<222> LOCATION: (5)..(5)
<223> OTHER INFORMATION: Nitrophenylalanine

<400> SEQUENCE: 19

Cys Ile Phe Lys Phe Tyr
1               5

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Nitrophenylalanine
<220> FEATURE:
<221> NAME/KEY: MOD_RES
<222> LOCATION: (6)..(6)
<223> OTHER INFORMATION: Nitrophenylalanine

<400> SEQUENCE: 20

Cys Ile Tyr Lys Phe Phe
1               5

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Nitrophenylalanine
<220> FEATURE:
<221> NAME/KEY: MOD_RES
<222> LOCATION: (6)..(6)
<223> OTHER INFORMATION: Nitrophenylalanine

<400> SEQUENCE: 21

Cys Ile Phe Lys Tyr Phe
1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (5)..(5)
<223> OTHER INFORMATION: Nitrophenylalanine

<400> SEQUENCE: 22

Cys Ile Tyr Lys Phe Tyr Phe
1               5

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Phosphorylated-Tyr

<400> SEQUENCE: 23

Cys Ile Tyr Lys Tyr Tyr
1               5

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Phe(4-Guanidine)

<400> SEQUENCE: 24

Cys Ile Tyr Lys Phe Tyr
1               5

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Phe(4-F)

<400> SEQUENCE: 25

Cys Ile Tyr Lys Phe Tyr
1               5

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Phe(4-Cl)
```

```
<400> SEQUENCE: 26

Cys Ile Tyr Lys Phe Tyr
1               5

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Phe(4-I)

<400> SEQUENCE: 27

Cys Ile Tyr Lys Phe Tyr
1               5

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Phe(CN)

<400> SEQUENCE: 28

Cys Ile Tyr Lys Phe Tyr
1               5

<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Phe(N3)

<400> SEQUENCE: 29

Cys Ile Tyr Lys Phe Tyr
1               5

<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Phe(4-NHSO2CH3)

<400> SEQUENCE: 30

Cys Ile Tyr Lys Phe Tyr
1               5
```

```
<210> SEQ ID NO 31
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Cys Ile Tyr Lys Tyr
1               5

<210> SEQ ID NO 32
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phe(4-Cl)

<400> SEQUENCE: 32

Cys Tyr Lys Phe Tyr
1               5

<210> SEQ ID NO 33
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphorylated-Tyr

<400> SEQUENCE: 33

Cys Tyr Lys Tyr Tyr
1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Nitrophenylalanine

<400> SEQUENCE: 34

Tyr Ile Phe Gly Ser Phe Lys
1               5

<210> SEQ ID NO 35
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Iodophenylalanine
```

-continued

```
<400> SEQUENCE: 35

Cys Ile Lys Tyr Phe Tyr
1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Tyr or Phe
<220> FEATURE:
<221> NAME/KEY: MOD_RES
<222> LOCATION: (3)..(3)
<223> OTHER INFORMATION: Tyr or Phe
<220> FEATURE:
<221> NAME/KEY: MOD_RES
<222> LOCATION: (6)..(6)
<223> OTHER INFORMATION: Tyr or Phe

<400> SEQUENCE: 36

Xaa Ile Xaa Gly Ser Xaa Lys
1               5

<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys(PhPPICH2CO)

<400> SEQUENCE: 37

Cys Ile Tyr Lys Tyr Tyr
1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gly(PhPPICH2CO)

<400> SEQUENCE: 38

Gly Cys Ile Tyr Lys Tyr Tyr
1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aminobutyric acid(PhPPICH2CO)
```

```
<400> SEQUENCE: 39

Xaa Cys Ile Tyr Lys Tyr Tyr
1               5

<210> SEQ ID NO 40
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Phe(COCH2PhPPI)

<400> SEQUENCE: 40

Cys Ile Phe Lys Tyr Tyr
1               5

<210> SEQ ID NO 41
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Lys(COCH2PhPPI)

<400> SEQUENCE: 41

Cys Ile Tyr Lys Tyr Tyr
1               5

<210> SEQ ID NO 42
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Phe(COCH2PhPPI)

<400> SEQUENCE: 42

Cys Ile Tyr Lys Phe Tyr
1               5

<210> SEQ ID NO 43
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Phe(COCH2PhPPI)

<400> SEQUENCE: 43

Cys Ile Tyr Lys Tyr Phe
1               5
```

```
<210> SEQ ID NO 44
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Cys Ile Phe Lys Tyr Tyr
1               5
```